(12) United States Patent
Davie et al.

(10) Patent No.: US 10,611,758 B2
(45) Date of Patent: Apr. 7, 2020

(54) N-((HET)ARYLMETHYL)-HETEROARYL-CARBOXAMIDES COMPOUNDS AS KALLIKREIN INHIBITORS

(71) Applicant: KalVista Pharmaceuticals Limited, Wiltshire (GB)

(72) Inventors: Rebecca Louise Davie, Salisbury (GB); Hannah Joy Edwards, Salisbury (GB); David Michael Evans, Salisbury (GB); Simon Teanby Hodgson, Bedfordshire (GB)

(73) Assignee: Kalvista Pharmaceuticals Limited, Porton Down, Wiltshire (GB)

( * ) Notice: Subject to any disclaimer, the term of this patent is extended or adjusted under 35 U.S.C. 154(b) by 0 days.

(21) Appl. No.: 16/460,630

(22) Filed: Jul. 2, 2019

(65) Prior Publication Data

US 2019/0330200 A1 Oct. 31, 2019

Related U.S. Application Data

(62) Division of application No. 15/527,923, filed as application No. PCT/GB2015/053615 on Nov. 26, 2015, now Pat. No. 10,364,238.

(30) Foreign Application Priority Data

Nov. 27, 2014 (GB) .................................. 1421083.5

(51) Int. Cl.
| | | |
|---|---|---|
| A61K 31/4439 | (2006.01) | |
| C07D 413/14 | (2006.01) | |
| A61P 43/00 | (2006.01) | |
| C07D 409/14 | (2006.01) | |
| C07D 401/10 | (2006.01) | |
| C07D 401/14 | (2006.01) | |
| C07D 401/06 | (2006.01) | |
| C07D 231/14 | (2006.01) | |
| C07D 403/10 | (2006.01) | |
| A61K 31/496 | (2006.01) | |
| A61K 31/445 | (2006.01) | |

(52) U.S. Cl.
CPC .......... *C07D 413/14* (2013.01); *A61K 31/445* (2013.01); *A61K 31/4439* (2013.01); *A61K 31/496* (2013.01); *A61P 43/00* (2018.01); *C07D 231/14* (2013.01); *C07D 401/06* (2013.01); *C07D 401/10* (2013.01); *C07D 401/14* (2013.01); *C07D 403/10* (2013.01); *C07D 409/14* (2013.01)

(58) Field of Classification Search
None
See application file for complete search history.

(56) References Cited

U.S. PATENT DOCUMENTS

| | | |
|---|---|---|
| 5,187,157 A | 2/1993 | Kettner et al. |
| 7,101,878 B1 | 9/2006 | Anderson et al. |
| 8,207,378 B2 | 6/2012 | Steinmetzer et al. |
| 9,382,219 B2 | 7/2016 | Das et al. |
| 9,512,065 B2 | 12/2016 | Northen et al. |
| 9,533,987 B2 | 1/2017 | Davie et al. |
| 9,670,157 B2 | 6/2017 | Allan et al. |
| 9,738,641 B2 | 8/2017 | Edwards et al. |
| 10,221,161 B2 | 3/2019 | Edwards et al. |
| 2007/0254894 A1 | 11/2007 | Kane et al. |
| 2008/0221091 A1 | 9/2008 | Gege et al. |
| 2009/0163545 A1 | 6/2009 | Goldfarb |
| 2010/0113782 A1 | 5/2010 | Bolin et al. |
| 2011/0152533 A1 | 6/2011 | Sinha et al. |
| 2012/0298326 A1 | 11/2012 | Born |
| 2014/0213611 A1 | 7/2014 | Evans et al. |
| 2014/0378474 A1 | 12/2014 | Flohr et al. |
| 2015/0191421 A1 | 7/2015 | Northen et al. |
| 2015/0315198 A1 | 11/2015 | Li et al. |
| 2017/0305863 A1 | 10/2017 | Evans et al. |
| 2018/0319782 A1 | 11/2018 | Davie et al. |

FOREIGN PATENT DOCUMENTS

| | | |
|---|---|---|
| EA | 201200917 | 12/2012 |
| EP | 1426364 A1 | 6/2004 |
| EP | 1568698 A1 | 8/2005 |
| EP | 2281885 A1 | 2/2011 |
| JP | 2010-520294 A | 6/2010 |
| RU | 2485114 C2 | 6/2013 |
| WO | 9204371 A1 | 3/1992 |
| WO | 9429335 A1 | 12/1994 |
| WO | 9507921 A1 | 3/1995 |
| WO | 03/35076 A1 | 5/2003 |
| WO | 03/37274 A2 | 5/2003 |
| WO | 03076458 A2 | 9/2003 |
| WO | 03091226 A1 | 11/2003 |

(Continued)

OTHER PUBLICATIONS

Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2 Supp), Abstract AB40, p. 1.

(Continued)

*Primary Examiner* — Samantha L Shterengarts
(74) *Attorney, Agent, or Firm* — BakerHostetler

(57) ABSTRACT

The present invention provides compounds of formula (I):

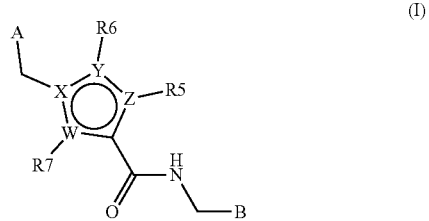

compositions comprising such compounds; the use of such compounds in therapy (for example in the treatment or prevention of a disease or condition in which plasma kallikrein activity is implicated); and methods of treating patients with such compounds; wherein R5, R6, R7, A, B, W, X, Y and Z are as defined herein.

1 Claim, No Drawings

(56) References Cited

FOREIGN PATENT DOCUMENTS

| | | |
|---|---|---|
| WO | 2004/062657 A1 | 7/2004 |
| WO | 2004/069792 A2 | 8/2004 |
| WO | 2005049578 A1 | 6/2005 |
| WO | 2005/079800 A1 | 9/2005 |
| WO | 2005123680 A1 | 12/2005 |
| WO | 2006091459 A2 | 8/2006 |
| WO | 2006/114313 A1 | 11/2006 |
| WO | 2007/011626 A2 | 1/2007 |
| WO | 2007113289 A1 | 10/2007 |
| WO | 2008016883 A2 | 2/2008 |
| WO | 2008049595 A1 | 5/2008 |
| WO | 2008091692 A2 | 7/2008 |
| WO | 2008/121670 A1 | 10/2008 |
| WO | 2009/012998 A1 | 1/2009 |
| WO | 2009026407 A1 | 2/2009 |
| WO | 2009/083553 A1 | 7/2009 |
| WO | 2009097141 A1 | 8/2009 |
| WO | 2009/106980 A2 | 9/2009 |
| WO | 2009/114677 A1 | 9/2009 |
| WO | 2010142801 A1 | 12/2010 |
| WO | 2011/075684 A1 | 6/2011 |
| WO | 2011/094496 A2 | 8/2011 |
| WO | 2011118672 A1 | 9/2011 |
| WO | 2012/009009 A2 | 1/2012 |
| WO | 2012004678 A2 | 1/2012 |
| WO | 2012017020 A1 | 2/2012 |
| WO | 2012/142308 A1 | 10/2012 |
| WO | 2012/174362 A1 | 12/2012 |
| WO | 2013/048982 A1 | 4/2013 |
| WO | 2013/049096 A1 | 4/2013 |
| WO | 2013111107 A1 | 8/2013 |
| WO | 2013111108 A1 | 8/2013 |
| WO | 2013120104 A2 | 8/2013 |
| WO | 2013/130603 A1 | 9/2013 |
| WO | 2014/108406 A1 | 7/2014 |
| WO | 2014108679 A1 | 7/2014 |
| WO | 2014145986 A1 | 9/2014 |
| WO | 2014188211 A1 | 11/2014 |
| WO | 2015022546 A1 | 2/2015 |
| WO | 2015022547 A1 | 2/2015 |
| WO | 2015103317 A1 | 7/2015 |
| WO | 2015134998 A1 | 9/2015 |
| WO | 2015171526 A2 | 11/2015 |
| WO | 2015171527 A1 | 11/2015 |
| WO | 2016011209 A1 | 1/2016 |
| WO | 2016029214 A1 | 2/2016 |
| WO | 2016044662 A1 | 3/2016 |
| WO | 2016/083820 A1 | 6/2016 |
| WO | 2016083816 A1 | 6/2016 |
| WO | 2016083818 A1 | 6/2016 |
| WO | 2016138532 A1 | 9/2016 |
| WO | 2017/001924 | 1/2017 |
| WO | 2017001926 A2 | 1/2017 |
| WO | 2017001936 A2 | 1/2017 |
| WO | 2017072020 A1 | 5/2017 |
| WO | 2017072021 A1 | 5/2017 |
| WO | 2017/207983 A1 | 12/2017 |
| WO | 2017/207985 A1 | 12/2017 |
| WO | 2017/208005 A1 | 12/2017 |
| WO | 2018/011628 A1 | 1/2018 |
| WO | 2019/106359 A1 | 6/2019 |
| WO | 2019/106375 A1 | 6/2019 |
| WO | 2019/106377 A1 | 6/2019 |

OTHER PUBLICATIONS

Bhoola et al., "Bioregulation of Kinins: Kallikreins, Kininogens and Kininases", Pharmacological Rev., Mar. 1992, 44 (1), pp. 1-80.

Bhoola et al., "Kallikrein-Kinin Cascade" Encyclopedia of Respiratory Medicine, 2006, pp. 483-493.

Bryant et al., "Human Plasma Kallikrein-Kinin System: Physiological and Biochemical Parameters", Cardiovascular and Haematological Agents in Medicinal Chemistry, Jul. 2009, pp. 234-250.

Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.

Campbell, "Towards Understanding the Kallikrein-Kinin System: Insights from the Measurement of Kinin Peptides", Brazilian Journal of Medical and Biological Research, Jun. 2000, 33(6), pp. 665-677.

Chilcote et al., "ASP-634: An Oral Drug Candidate for Diabetic Macular Edema", ARVO Mar. 2012, Presentation 2240, Abstract, p. 1.

Clermont et al., "Plasma Kallikrein Mediates Retinal Vascular Dysfunction and Induces Retinal Thickening in Diabetic Rats", Diabetes, May 2011, 60(5), pp. 1590-1598.

Collis et al., "BCX4161, An Oral Kallikrein Inhibitor: Safety and Pharmacokinetic Results of a Phase 1 Study in Healthy Volunteers", Journal of Allergy and Clinical Immunology, vol. 133, Issue 2, Supplement, Feb. 2014, p. AB39.

CAS Extract for Compound 1086603-52-2, dated Dec. 18, 2008, 2 pages.

CAS Extract for Compound 1094996-93-6, dated Jan. 22, 2009, 1 page.

CAS Extract for Compound 1171693-25-6, dated Aug. 2, 2017, 1 page.

CAS Extract for Compound 1386189-59-8, dated Aug. 3, 2012, 1 page.

Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, pp. 1064-1077.

Evans et al., "Selective Inhibitors of Plasma Kallikrein", Immunopharmacology, May 1996, 32(1-3), pp. 115-116.

Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), pp. 60-71.

Griesbacher et al., "Involvement of Tissue Kallikrein But Not Plasma Kallikrein in the Development of Symptoms Mediated by Endogenous Kinins in Acute Pancreatitis in Rats", British Journal of Pharmacology, 2002, 137, pp. 692-700.

Johansen et al., "Assay of Kallikrein Inhibitors and Levels of Acetone-Activated Kallikrein in Plasma Specimens from Reactors to Dextran or to Contrast Media", International Journal Tissue Reactions, 1986, 8, pp. 185-192.

Kolte et al., "Biochemical Characterization of a Novel High-Affinity and Specific Kallikrein Inhibitor", British Journal of Pharmacology, Apr. 2011, 162(7), pp. 1639-1649.

Lehmann, "Ecallantide (DX-88), a Plasma Kallikrein Inhibitor for the Treatment of Hereditary Angioedema and the Prevention of Blood Loss in On-Pump Cardiothoracic Surgery", Expert Opinion Biol. Ther., Jul. 2008, 8(8), pp. 1187-1199.

Leinweber et al, "Possible Physiological Roles of Carboxylic Ester Hydrolases", Drug Metabolism Reviews, Jan. 1987, 18(4), pp. 379-439.

Liang et al. "Fast-Dissolving Intraoral Drug Delivery Systems", Expert Opinion in Therapeutic Patients, Jun. 2001, 11(6), pp. 981-986.

Lieberman et al., Pharmaceutical Dosage Forms: Tablets, vol. 1, 1980, pp. 145-157.

Marceau et al., "Bradykinin Receptor Ligands: Therapeutic Perspectives", Nature Reviews Drug Discovery, Oct. 2004, 3, pp. 845-852.

Okada et al., "Development of Potent and Selective Plasmin and Plasma Kallikrein Inhibitors and Studies on the Structure-Activity Relationship", Chem. Pharm. Bull., Sep. 2000, 48, pp. 1964-1972.

Patel, "Combination Therapy for Age-Related Macular Degeneration", Retina, Jun. 2009, 29(6), pp. S45-S48.

Remington: Practice of the Science and Pharmacy; 19th Edition; Mack Publishing Company, 1995, 5 pages.

(56) References Cited

OTHER PUBLICATIONS

Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), pp. 1209-1217.
Sturzebecher et al., "Inhibition of Human Mast Cell Tryptase by Benzamidine Derivatives", Biological Chemistry Hoppe-Seyler, Oct. 1992, 373(2), p. 1025.
Sturzebecher et al., "Novel Plasma Kallikrein Inhibitors of the Benzamidine Type", Brazilian J. Med. Biol. Res, Aug. 1994, 27(8), pp. 1929-1934.
Tang et al., "Expression, Crystallization, and Three-Dimensional Structure of the Catalytic Domain of Human Plasma Kallikrein", The Journal of Biological Chemistry vol. 280, No. 49, Dec. 2005, pp. 41077-41089.
Teno et al., "Development of Active Center-Directed Plasmin and Plasma Kallikrein Inhibitors and Studies on the Structure-Inhibitory Activity Relationship", Chemical and Pharmaceutical Bulletin, Jun. 1993, 41(6), pp. 1079-1090.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Young et al., "Small Molecule Inhibitors of Plasma Kallikrein", Bioorg. Med. Chem. Letts., Apr. 2006, 16(7), pp. 2034-2036.
Zhang et al. "Discovery of Highly Potent Small Molecule Kallikrein Inhibitors", Medicinal Chemistry, 2006, 2, pp. 545-553.
Pace, et al., "4-Hydroxy-5-pyrrolinone-3-carboxamide HIV-1 integrase inhibitors", Bioorganic Medicinal Chemistry Letters., Jun. 18, 2008, pp. 3865-3869.
Registry No. 1086603-42-0, Chemical Library-AKos Consulting and Solutions GmbH, CHEMCATS, dated Dec. 18, 2008, 1 page.
Registry No. 1318167-86-0, Chemical Library—Fch Group, CHEMCATS, dated Aug. 15, 2011, 1 page.
Registry No. 1570266-44-2, Chemical Library—FCH Group, dated Mar. 19, 2014, 1 page.
Registry No. 1572436-72-6, Chemical Library—FCH Group, dated Mar. 24, 2014, 1 page.
Registry No. 1573976-69-8, Chemical Library—FCH Group, dated Mar. 26, 2014, 1 page.
Registry No. 1575214-30-0, Chemical Library—FCH Group, dated Mar. 28, 2014, 1 page.
Registry No. 1580327-09-8, Chemical Library—FCH Group, dated Apr. 4, 2014, 1 page.
Registry No. 1572946-10-1, Chemical Library—FCH Group, Mar. 25, 2014, 1 page.
Registry No. 1569406-35-4, Chemical Library—FCH Group, Mar. 18, 2014, 1 page.
Registry No. 1320653-15-3, Chemical Library—FCH Group, Aug. 21, 2011, 1 page.
Registry No. 1086603-37-3, Chemical Library-AKos Consulting and Solutions GmbH, CHEMCATS, dated Dec. 18, 2008, 1 page.
Ambinter Sari: "1 H-Pyrazole-4-carboxamides" In: Chemical Catalog, Sep. 11, 2011 (Sep. 11, 2011), Ambinter SARL, XP055601375.
Babu, "Drug Discovery at BioCryst Pharmaceuticals Inc.", Presentation, http://files.shareholder.com/downloads/BCRX/OxOx403076/97a18d6e-1621-4fc6--8f5fd0828bddab4f/, Sep. 16, 2010, 18 pages.
Bird et al. Thrombosis and Haemostasis, Effects of plasma kallikrein deficiency on haemostasis and thrombosis in mice: Murine Ortholog of the Fletcher Trait, 2012, 107, 1141-50.
Bjorkqvist et al., "Plasma kallikrein: the bradykinin-producing enzyme", Thrombosis and Haemotasis, 2013, 110, 399-407.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channe Activators. XII" European Journal of Medicinal Chemistry 43, 2008, pp. 2618-2626.
Cannon, Chapter Nineteen in Burger's Medicinal Chemistry and Drug Discovery, Fifth Edition, vol. I: Principles and Practice, Wiley-Interscience 1995, pp. 783-802.
CAS abstract accession No. 1990:515202, corresponding to Ried et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages.
CAS abstract accession Nos. 2009:769551 and 2009:846114, corresponding to U.S. Publication 2009-0163545A1, 5 pages.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-4-4, dated Apr. 18, 2011, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS Extract for Compound 1626023-22-0, dated Sep. 25, 2014, 1 page.
CAS Structures cited in WO201683818 Written Opinion dated Jun. 2, 2016, 290 pages.
Chemical Abstract Service, CHEMCATS, RN 1424383-07-2, Mar. 15, 2013.
Chemical Abstracts Registry No. 1147797-44-1, indexed in the Registry file on STN CAS Online May 20, 2009.
Chemical Abstracts Registry No. 1217027-87-6, indexed in the Registry file on STN CAS Online Apr. 5, 2010.
Chemical Abstracts Registry No. 1241137-33-6, indexed in the Registry file on STN CAS Online Sep. 15, 2010.
Chemical Abstracts Registry No. 1295467-87-6, indexed in the Registry file on STN CAS Online May 16, 2011.
Chemical Abstracts Registry No. 1296846-83-7, indexed in the Registry file on STN CAS Online May 18, 2011.
Chemical Abstracts Registry No. 1297526-11-4, indexed in the Registry file on STN CAS Online May 19, 2011.
Chemical Abstracts Registry No. 1389653-06-8, indexed in the Registry file on STN CAS Online Aug. 12, 2012.
Chemical Abstracts Registry No. 1575116-26-5, indexed in the Registry file on STN CAS Online Mar. 28, 2014.
Chemical Abstracts Registry No. 942731-43-3, indexed in the Registry file on STN CAS Online Jul. 19, 2007.
Chemical Abstracts Registry No. 955899-78-2, indexed in the Registry file on STN CAS Online on Nov. 25, 2007.
Colman, "Plasma and tissue kallikrein in arthritis and inflammatory bowel disease", Immunopharmacology, 1999, 43, 103-108.
Davis III et al., "Biological activities of C1 inhibitor", Molecular Immunology, 2008, 45, 4057-4063.
Enamine website on Jul. 25, 2013 from the Internet Archive Way Back Machine {https://web.archive.org/web/20130725053127/http://www.enamine.net/index.php?option=com_content&task=view&id=22.
Feener at al., "Role of plasma kallikrein in diabetes and metabolism", Thrombosis and Haemostasis, Sep. 2013, 110(3), 434-441.
Ikeda et al., "Host Stromal Bradykinin B.sub.2 Receptor Signaling Facilitates Tumor-Associated Angiogenesis and Tumor Growth", Cancer Research, Aug. 2004, 64, 5178-5185.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
International Search Report for PCT/GB2014/051592 completed Jul. 23, 2014.

(56) References Cited

OTHER PUBLICATIONS

Jaffa et al., "Plasma Prekallikrein a Risk Marker for Hypertension and Nephropathy in Type 1 Diabetes", Diabetes, May 2003, vol. 52, 1215-1221.
Katsuura et al., "Effects of a Highly Selective Synthetic Inhibitor of Plasma Kallikrein on Disseminated Intravascular Coagulation in Rats" Thrombosis Research, 1996, 82, 361-368.
Kenniston, J Bio Chem, "Inhibition of Plasma Kallikrein by a Highly Specific Active Site Blocking Antibody", vol. 289 (34), 2014, 23596-23608.
Liu et al., Nat Med., Hyperglycemia Induced Cerebral Hematoma Expansion is Mediated by Plasma Kallikrein, 2011, 17, 206-210.
Lussis et al.; "A single synthetic small molecule that generates force against a load"; Nature Nanotechnology; vol. 6; 2011; p. 553-557.
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Pace, et al., "4-Hydroxy-5-pynolinone-3-carboxamide HIV-1 integrase inhibitors", Bioorganic & Medicinal Chemistry Letters., Jun. 18, 2008, pp. 3865-3869.
Prassas, "Unleashing the therapeutic potential of human kallikrein—related serine proteases", Nature Reviews Drug Discovery, vol. 14, 183-202, 2015.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028094-50-9, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1094996-93-6, Chemical Library—AKos Consulting and Solutions GmbH, CHEMCATS, dated Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library-Ambinter, CHEMCATS, dated Aug. 2, 2017, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318604-27-1, Chemical Library—FCG Group, Aug. 16, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—Ukrorgsyntez Ltd., CHEMCATS, dated Aug. 3, 2012, 1 page.
Registry No. 1390613-03-2, Chemical Library—FCG Group, Aug. 13, 2012, 1 page.
Registry No. 1575116-26-5, Chemical Library—FCG Group, Mar. 28, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 955899-78-2, Chemical Library—FCG Group, Nov. 25, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Registry No. 956444-80-7, Chemical Library—FCG Group, Dec. 2, 2007, 1 page.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.
Registry No. 1015534-45-8, Chemical Library—FCG Group, Apr. 18, 2008, 1 page.
Revenko et al., Blood Journal, "Selective depletion of plasma prekallikrein or coagulation factor XII inhibits thrombosis in mice without increased risk of bleeding", 2011, 118, 5302-5311.
Siebeck et al., "Inhibition of Plasma Kallikrein With Aprotinin in Porcine Endotoxin Shock", The Journal of Trauma, 1993, vol. 34, No. 2, 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, 1,6-dihydro-N-[1-(6-methyl-1 H-benzimidazol-2-yl)ethyl]-2-oxo-2-(1H-1,2,4-triazol-1-ylmethyl)", CAS No. 1422635-37-7, Mar. 8, 2013.
STN Registry, "5-Pyrimidinecarboxamide, N-[1-(1 H-benzimidazol-2-yl)ethyl]-1,6-dihydro-6-oxo-2-(phenoxymethyl)", CAS No. 1434334-41-4, Jun. 5, 2013.
Tanaka et al., Thrombosis Research, Evaluation of a novel kallikrein inhibitor on hemostatic activation in vitro; 2004, 113, 333-339.
Tombran-Tink et al., "Opthamology Research", Visual Dysfunction in Diabetes the Science of Patient Impairment and Health Care, 2012, 4 pages.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.

N-((HET)ARYLMETHYL)-HETEROARYL-CARBOXAMIDES COMPOUNDS AS KALLIKREIN INHIBITORS

CROSS-REFERENCE TO RELATED APPLICATIONS

This application is a divisional of U.S. patent application Ser. No. 15/527,923, filed May 18, 2017, which is the U.S. national stage of International Patent Application No. PCT/GB2015/053615, filed Nov. 26, 2015, which claims the benefit of Great Britain Patent Application No. 1421083.5, filed Nov. 27, 2014, the disclosures of which are incorporated by reference herein.

This invention relates to enzyme inhibitors that are inhibitors of plasma kallikrein and to pharmaceutical compositions containing and the uses of, such inhibitors.

BACKGROUND TO THE INVENTION

The heterocyclic derivatives of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunopharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic Macular Edema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010, 142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandl et al. ("N-((6-amino-pyridin-3-yl) methyl)-heteroaryl-carboxamides as inhibitors of plasma kallikrein" WO2012/017020), which describes compounds that feature an amino-pyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandl et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic. Another example is Allen et al. "Benzylamine derivatives" WO2014/108679.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of heterocyclic derivatives that are inhibitors of plasma kallikrein. These compounds demonstrate good selectivity for plasma kallikrein and are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In a first aspect, the present invention provides compounds of formula I

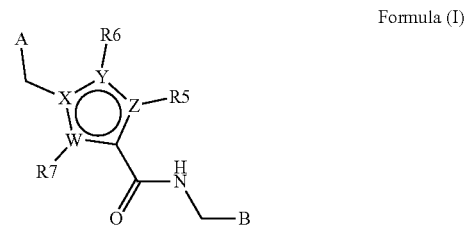

Formula (I)

wherein

B is phenyl substituted with 1 to 4 substituents selected from alkyl$^b$, alkoxy, OH, halo, CN, heteroaryl, COOR8, NHCOR8, CONR8R9, OCF$_3$, and CF$_3$;

B is selected from benzothiophenyl, benzofuranyl, benzomorpholinyl, and a 5 or 6 membered heterocyclic ring containing one or two heteroatoms selected from N, O and S; wherein said 5 or 6 membered heterocyclic ring may be aromatic or non-aromatic; and wherein said benzothiophenyl, said benzofuranyl, said benzomorpholinyl or said 5 or 6 membered heterocyclic ring is substituted with 1 to 3 substituents selected from alkyl$^b$, alkoxy, OH, oxo, halo, CN, heteroaryl, COOR8, NHCOR8, CONR8R9, OCF$_3$ and CF$_3$;

W is C and X, Y and Z are independently selected from C, N, O and S, such that the ring containing W, X, Y and Z is a five membered aromatic heterocycle;

R5 and R6 are independently absent or independently selected from H, alkyl, cycloalkyl, alkoxy, halo, OH, aryl, heteroaryl, N-linked pyrrolidinyl, N-linked piperidinyl, N-linked morpholinyl, N-linked piperazinyl, —NR8R9, CN, COOR8, CONR8R9, —NR8COR9 and CF$_3$; wherein at least one of R5 and R6 is present and is not H;

R7 is H;

A is selected from aryl and heteroaryl; wherein aryl is substituted with 1, 2 or 3 substituents independently selected from alkyl, alkoxy, methylenedioxy, ethylenedioxy, OH, halo, CN, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{0-3}$—NR10R11, OCF$_3$ and CF$_3$; and heteroaryl is substituted with 1, 2 or 3 substituents independently selected from alkyl, alkoxy, OH, OCF$_3$, halo, CN, aryl, —(CH$_2$)$_{1-3}$-aryl, —(CH$_2$)$_{0-3}$—NR10R11, heteroaryl$^b$, —COOR10, —CONR10R11 and CF$_3$;

R8 and R9 are independently selected from H and alkyl;

alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, CF$_3$, COOR10, CONR10R11, fluoro and NR10R11;

alkyl$^b$ is a linear saturated hydrocarbon having up to 6 carbon atoms or a branched saturated hydrocarbon of between 3 and 6 carbon atoms ($C_{3-6}$); alkyl$^b$ may optionally be substituted with 1 or 2 substituents independently selected from $(C_1-C_6)$alkoxy, OH, CN, $CF_3$, COOR10, CONR10R11 and fluoro;

cycloalkyl is a monocyclic saturated hydrocarbon of between 3 and 6 carbon atoms;

alkoxy is a linear O-linked hydrocarbon of between 1 and 6 carbon atoms $(C_1-C_6)$ or a branched O-linked hydrocarbon of between 3 and 6 carbon atoms $(C_3-C_6)$; alkoxy may optionally be substituted with 1 or 2 substituents independently selected from OH, CN, $CF_3$, COOR10, CONR10R11, fluoro and NR10R11;

aryl is phenyl, biphenyl or naphthyl; aryl may be optionally substituted with 1, 2 or 3 substituents independently selected from alkyl, alkoxy, methylenedioxy, ethylenedioxy, OH, halo, CN, heteroaryl, —$(CH_2)_{0-3}$—O-heteroaryl, $aryl^b$, —O-$aryl^b$, —$(CH_2)_{1-3}$-$aryl^b$, —$(CH_2)_{1-3}$-heteroaryl, —COOR10, —CONR10R11, —$(CH_2)_{0-3}$—NR10R11, $OCF_3$ and $CF_3$;

$aryl^b$ is phenyl, biphenyl or naphthyl, which may be optionally substituted with 1, 2 or 3 substituents independently selected from alkyl, alkoxy, OH, halo, CN, —COOR10, —CONR10R11, $CF_3$ and NR10R11;

heteroaryl is a 5, 6, 9 or 10 membered mono- or bi-cyclic aromatic ring, containing, where possible, 1, 2, 3 or 4 ring members independently selected from N, NR8, S and O; heteroaryl may be optionally substituted with 1, 2 or 3 substituents independently selected from alkyl, alkoxy, OH, $OCF_3$, halo, CN, aryl, —$(CH_2)_{1-3}$-aryl, —$(CH_2)_{0-3}$—NR10R11, $heteroaryl^b$, —COOR10, —CONR10R11 and $CF_3$;

$heteroaryl^b$ is a 5, 6, 9 or 10 membered mono- or bi-cyclic aromatic ring, containing, where possible, 1, 2 or 3 ring members independently selected from N, NR8, S and O; wherein $heteroaryl^b$ may be optionally substituted with 1, 2 or 3 substituents independently selected from alkyl, alkoxy, OH, halo, CN, aryl, —$(CH_2)_{1-3}$-aryl, —COOR10, —CONR10R11, $CF_3$ and NR10R11;

R10 and R11 are independently selected from H, alkyl, $aryl^b$ and $heteroaryl^b$ or R10 and R11 together with the nitrogen atom to which they are attached form a carbon-containing 4-, 5-, 6- or 7-membered heterocyclic ring, optionally containing an additional heteroatom selected from N, S and O, which may be saturated or unsaturated with 1 or 2 double bonds and which may be optionally mono- or di-substituted with substituents selected from oxo, alkyl, alkoxy, OH, halo and $CF_3$;

and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In a further aspect, also provided are compounds of formula (I), wherein:

B is selected from phenyl, thiophenyl, benzothiophenyl and pyridyl, each substituted with 1 to 3 substituents selected from $alkyl^b$, alkoxy, halo, CN, COOR8, CONR8R9, $OCF_3$ and $CF_3$; wherein $alkyl^b$, alkoxy, R8 and R9 are as defined above;

W is C and X, Y and Z are independently selected from C and N, such that the ring containing W, X, Y and Z is a five membered aromatic heterocycle;

R5 and R6 are independently absent or independently selected from H, $CH_2OCH_3$, cycloalkyl, —NR8R9, —NR8COR9 and $CF_3$; wherein at least one of R5 and R6 is present and is not H;

R7 is H;

A is selected from:

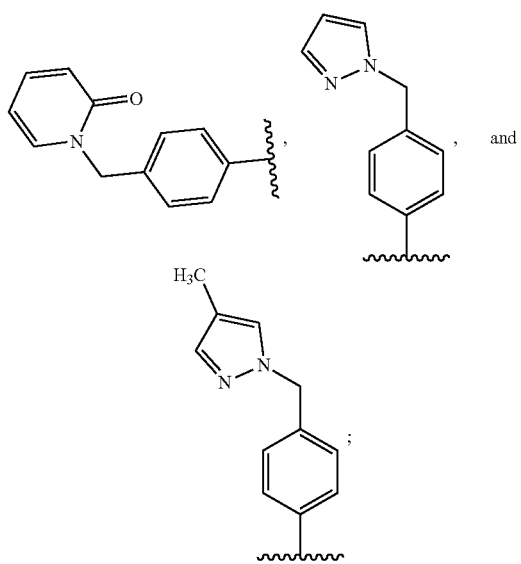

wherein alkyl, cycloalkyl, alkoxy, R8 and R9 are as defined above;

and tautomers, isomers, stereoisomers (including enantiomers, diastereoisomers and racemic and scalemic mixtures thereof), pharmaceutically acceptable salts and solvates thereof.

In a further aspect, also provided are compounds of formula (I), wherein:

B is selected from phenyl and pyridyl, each substituted with 1 to 3 substituents selected from methyl, ethyl, methoxy, ethoxy, $CF_3$, CN and F;

W is C, X is N and Y and Z are selected from C and N;

R7 is H and R5 and R6 are independently absent or independently selected from H, $CH_2OCH_3$, cyclopropyl, $NH_2$ and $CF_3$; wherein at least one of R5 and R6 is present and is not H;

A is selected from:

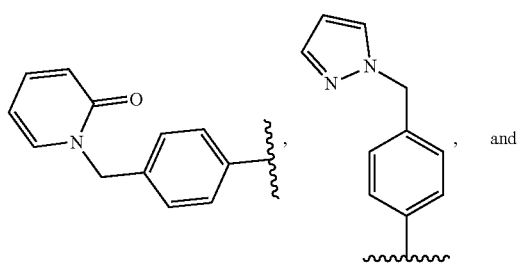

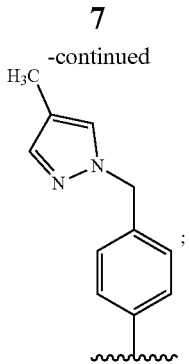

and tautomers, isomers, stereoisomers (including enantiomers, diastereoisomers and racemic and scalemic mixtures thereof), pharmaceutically acceptable salts and solvates thereof.

The aspects of the invention described above may also comprise the following features:

- B is phenyl substituted with 1 to 4 substituents selected from alkyl$^b$, alkoxy, OH, halo, CN, heteroaryl, COOR8, NHCOR8, CONR8R9, OCF$_3$, and CF$_3$; or B is selected from benzothiophenyl, benzofuranyl, benzomorpholinyl, and a 5 or 6 membered heterocyclic ring containing one or two heteroatoms selected from N, O and S; wherein said 5 or 6 membered heterocyclic ring may be aromatic or non-aromatic; and wherein said benzothiophenyl, said benzofuranyl, said benzomorpholinyl or said 5 or 6 membered heterocyclic ring is substituted with 1 to 3 substituents selected from alkyl$^b$, alkoxy, OH, oxo, halo, CN, heteroaryl, COOR8, NHCOR8, CONR8R9, OCF$_3$ and CF$_3$;
- B is phenyl substituted with 1 to 4 substituents selected from alkyl$^b$, alkoxy, OH, halo, CN, heteroaryl, COOR8, NHCOR8, CONR8R9, OCF$_3$, and CF$_3$; or B is selected from benzothiophenyl, benzofuranyl, and a 5 or 6 membered heterocyclic ring containing one or two heteroatoms selected from N, O and S; wherein said 5 or 6 membered heterocyclic ring may be aromatic or non-aromatic; and wherein said benzothiophenyl, said benzofuranyl or said 5 or 6 membered heterocyclic ring is substituted with 1 to 3 substituents selected from alkyl$^b$, alkoxy, OH, oxo, halo, CN, heteroaryl, COOR8, NHCOR8, CONR8R9, OCF$_3$ and CF$_3$; wherein alkyl$^b$, alkoxy, R8 and R9 are as defined above.
- B is selected from phenyl, pyridyl, pyrimidone, pyrimidine, thiazolyl, isothiazolyl, pyrazolyl, imidazolyl, isoxazolyl, oxazolyl, thiophenyl, benzothiophenyl and furanyl, each substituted, when possible, with 1 to 3 substituents selected from alkyl$^b$, alkoxy, OH, oxo, halo, CN, COOR8, CONR8R9, OCF$_3$ and CF$_3$; wherein alkyl$^b$, alkoxy, R8 and R9 are as defined above.
- B is selected from phenyl, pyridyl, pyrimidone, thiazolyl, pyrazolyl, isoxazolyl, thiophenyl, benzothiophenyl and furanyl, each substituted, when possible, with 1 to 3 substituents selected from alkyl$^b$, alkoxy, OH, oxo, halo, CN, COOR8, CONR8R9, OCF$_3$ and CF$_3$; wherein alkyl$^b$, alkoxy, R8 and R9 are as defined above.
- B is selected from phenyl, thiophenyl, benzothiphenyl and pyridyl, each substituted with 1 to 3 substituents selected from alkyl$^b$, alkoxy, halo, CN, COOR8, CONR8R9, OCF$_3$ and CF$_3$; wherein alkyl$^b$, alkoxy, R8 and R9 are as defined above.
- B is selected from phenyl and pyridyl, each substituted with 1 to 3 substituents selected from alkyl$^b$, alkoxy, CN, CF$_3$ and halo; wherein alkyl$^b$ and alkoxy are as defined above.
- B is selected from phenyl and pyridyl, each substituted with 1 to 3 substituents selected from alkyl$^b$, alkoxy, CF$_3$ and halo; wherein alkyl$^b$ and alkoxy are as defined above.
- B is selected from phenyl and pyridyl, each substituted with 1 to 3 substituents selected from methyl, ethyl, methoxy, ethoxy, CF$_3$, CN and F.
- B is selected from phenyl and pyridyl, each substituted with 1 to 3 substituents selected from methyl, ethyl, methoxy, ethoxy, CF$_3$, Cl, CHF$_2$ and F.
- B is selected from phenyl substituted with 1 to 3 substituents selected from methyl, ethyl, methoxy, ethoxy, CN, CF$_3$, Cl, CHF$_2$ and F.
- B is selected from phenyl substituted with 1 to 3 substituents selected from methyl, ethyl, methoxy, ethoxy, CF$_3$, Cl, CHF$_2$ and F.
- W is C and X, Y and Z are independently selected from C and N, such that the ring containing W, X, Y and Z is a five membered aromatic heterocycle.
- W is C and X, Y and Z are independently selected from C and N, such that the ring containing W, X, Y and Z is selected from pyrrole, pyrazole, imidazole and 1, 2, 3-triazole.
- W is C and X, Y and Z are independently selected from C and N, such that the ring containing W, X, Y and Z is selected from pyrazole and imidazole.
- W is C.
- X is N.
- W is C, X is N and Y and Z are selected from C and N.
- W is C, X is N, Y is N and Z is C.
- W is C, X is N, Y is C and Z is N.
- R5 and R6 are independently absent or independently selected from H, alkyl, cycloalkyl, alkoxy, halo, OH, aryl, heteroaryl, N-linked pyrrolidinyl, N-linked piperidinyl, N-linked morpholinyl, N-linked piperazinyl, —NR8R9, CN, COOR8, CONR8R9, —NR8COR9 and CF$_3$; wherein at least one of R5 and R6 is present and is not H; wherein alkyl, cycloalkyl, alkoxy, aryl, heteroaryl, R8 and R9 are as defined above.
- R5 and R6 are independently absent or independently selected from H, alkyl, cycloalkyl, —NR8R9, CN, —NR8COR9 and CF$_3$; wherein at least one of R5 and R6 is present and is not H; wherein alkyl, cycloalkyl, R8 and R9 are as defined above.
- R5 and R6 are independently absent or independently selected from H, CH$_2$OCH$_3$, cycloalkyl, CN, —NR8R9, —NR8COR9 and CF$_3$; wherein at least one of R5 and R6 is present and is not H; wherein cycloalkyl, R8 and R9 are as defined above.
- R5 and R6 are independently absent or independently selected from H, cycloalkyl, CN, —NR8R9, —NR8COR9 and CF$_3$; wherein at least one of R5 and R6 is present and is not H; wherein cycloalkyl, R8 and R9 are as defined above.
- R5 and R6 are independently absent or independently selected from H, CH$_2$OCH$_3$, cycloalkyl, CN, NR8R9 and CF$_3$; wherein R8 and R9 are H and cycloalkyl is as defined above; and, wherein at least one of R5 and R6 is present and is not H.
- R7 is H.
- R7 is H and R5 and R6 are independently absent or independently selected from H, CH$_2$OCH$_3$, cyclopropyl, CN, NH₂ and CF₃; wherein at least one of R5 and R6 is present and is not H.

R7 is H and R5 and R6 are independently absent or independently selected from H, CH₂OCH₃, cyclopropyl, NH₂, CN and CF₃; wherein at least one of R5 and R6 is present and is not H.

R7 is H and R5 and R6 are independently absent or independently selected from H, CH₂OCH₃, cyclopropyl, NH₂ and CF₃; wherein at least one of R5 and R6 is present and is not H.

R7 is H, R6 is absent and R5 is selected from CH₂OCH₃, cyclopropyl, NH₂ and CF₃.

R7 is H, R6 is absent and R5 is CH₂OCH₃.

W is C, X is N, Y and Z are selected from C and N, R7 is H and R5 and R6 are independently absent or independently selected from H, CH₂OCH₃, cycloalkyl, NR8R9 and CF₃; wherein R8 and R9 are H and cycloalkyl is as defined above.

W is C, X is N, Y is N, Z is C, R7 is H, R6 is absent and R5 is selected from CH₂OCH₃, cyclopropyl, NH₂ and CF₃.

A is selected from aryl and heteroaryl, each substituted as specified above.

A is phenyl, pyridyl, thiophenyl or quinolinyl, each substituted with 1, 2 or 3 substituents independently selected from alkyl, alkoxy, halo, CN, aryl$^b$, —(CH₂)₁₋₃-aryl$^b$, —(CH₂)₁₋₃-heteroaryl, —(CH₂)₀₋₃—NR10R11 and CF₃; wherein alkyl, alkoxy, heteroaryl, aryl$^b$, R10 and R11 are as defined above.

A is phenyl or pyridyl, each substituted with 1, 2 or 3 substituents independently selected from alkyl, alkoxy, halo, —(CH₂)₁₋₃-aryl$^b$, —(CH₂)₁₋₃-heteroaryl, CF₃ and —(CH₂)₀₋₃—NR10R11; wherein alkyl, alkoxy, heteroaryl, aryl$^b$, R10 and R11 are as defined above.

A is pyridyl substituted with 1, 2 or 3 substituents independently selected from alkyl, halo, heteroaryl$^b$, CF₃ and —NR10R11; wherein alkyl, heteroaryl$^b$, R10 and R11 are as defined above.

A is pyridyl substituted with heteroaryl$^b$ or —NR10R11 and, optionally, 1 or 2 additional substituents independently selected from alkyl, halo and CF₃; wherein alkyl, heteroaryl$^b$, R10 and R11 are as defined above.

A is phenyl substituted with 1, 2 or 3 substituents independently selected from alkyl, halo, —(CH₂)₁₋₃-heteroaryl, CF₃ and —(CH₂)₁₋₃—NR10R11; wherein alkyl, heteroaryl, R10 and R11 are as defined above.

A is phenyl substituted with —(CH₂)₁₋₃-heteroaryl or —(CH₂)₁₋₃—NR10R11 and, optionally, 1 or 2 additional substituents independently selected from alkyl, halo and CF₃; wherein alkyl, heteroaryl, R10 and R11 are as defined above.

A is selected from

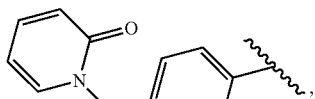

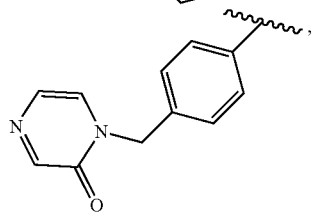

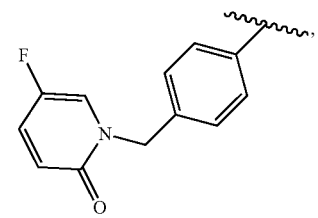

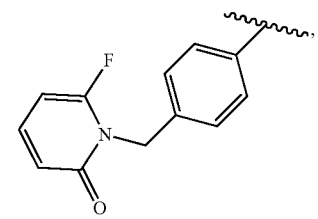

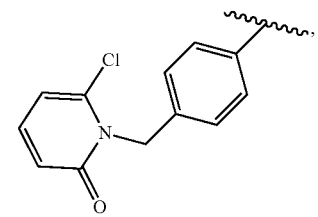

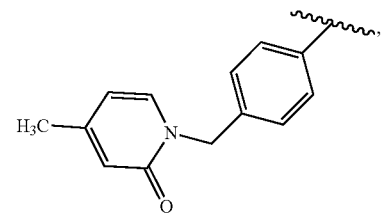

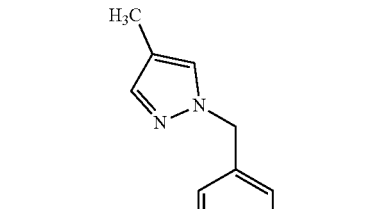

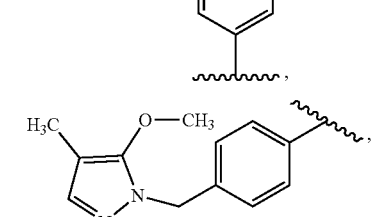

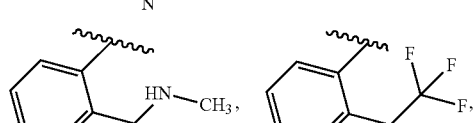

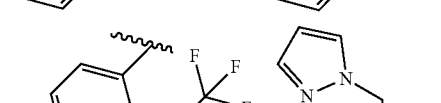

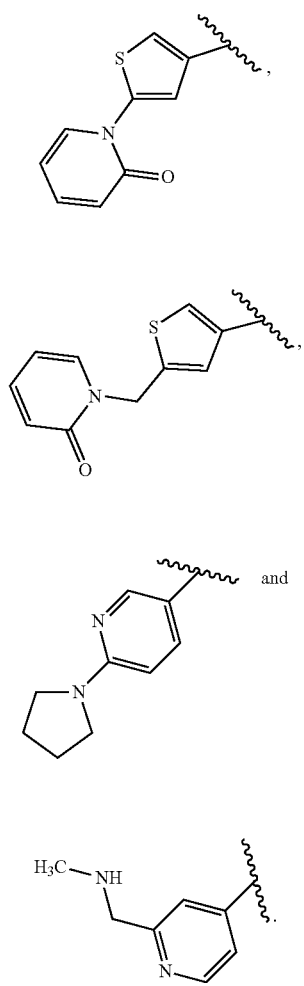
A is selected from:
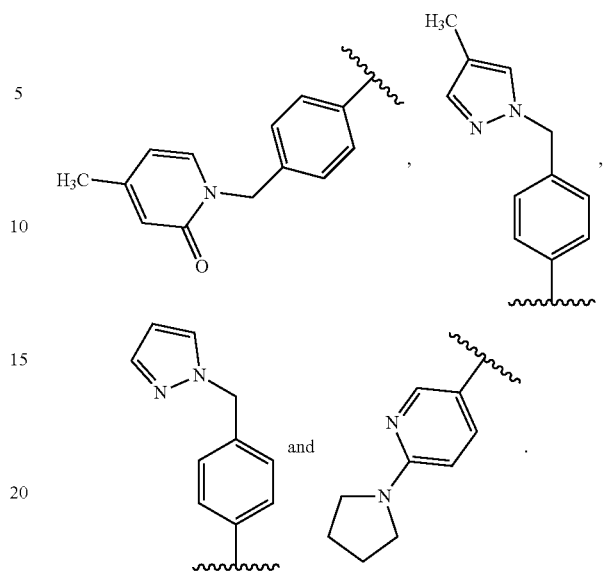
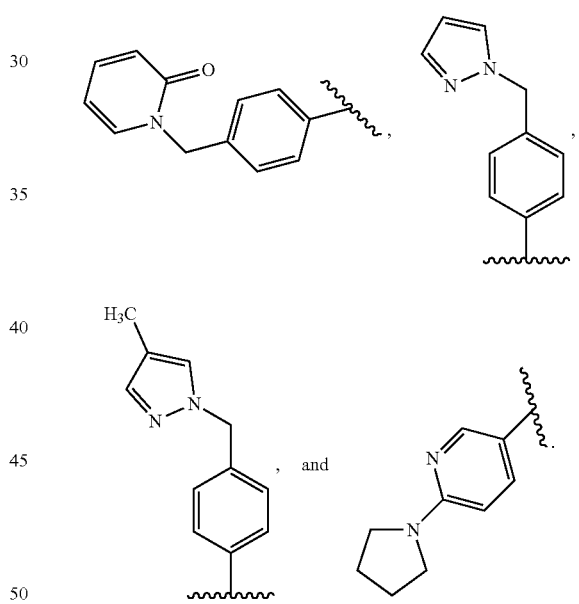
A is selected from:
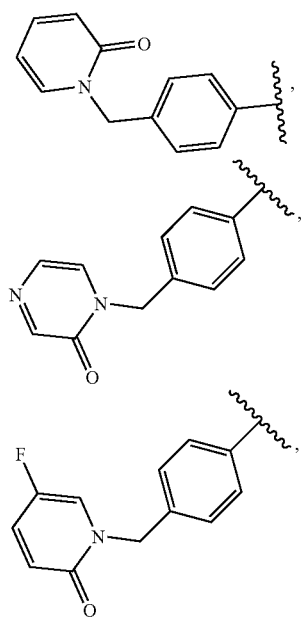
A is selected from:
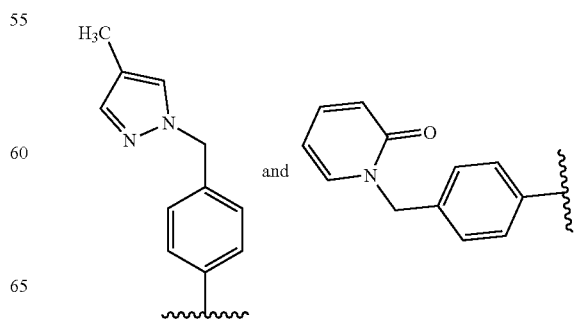

A is:

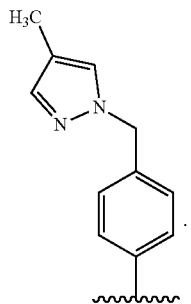 [SMILES: *c1ccc(Cn2cc(C)cn2)cc1]

A is:

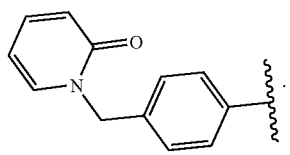 [SMILES: *c1ccc(Cn2ccccc2=O)cc1]

R8 and R9 are independently selected from H and alkyl; wherein alkyl is defined above.

R8 and R9 are independently selected from H and methyl, ethyl, n-propyl and isopropyl.

R8 and R9 are independently selected from H and methyl.

R10 and R11 are independently selected from H, alkyl, aryl$^b$ and heteroaryl$^b$ or R10 and R11 together with the nitrogen atom to which they are attached form a carbon-containing 4-, 5-, 6- or 7-membered heterocylic ring, optionally containing an additional heteroatom selected from N, S and O, which may be saturated or unsaturated with 1 or 2 double bonds and which may be optionally mono- or di-substituted with substituents selected from oxo, alkyl, alkoxy, OH, halo and CF$_3$; wherein alkyl, alkoxy, aryl$^b$ and heteroaryl$^b$ are as defined above.

R10 and R11 are independently selected from H and alkyl or R10 and R11 together with the nitrogen atom to which they are attached form a carbon-containing 5- or 6-membered heterocylic ring, optionally containing an addition N atom, which may be saturated or unsaturated with 1 or 2 double bonds and which may be optionally mono- or di-substituted with substituents selected from oxo, alkyl, alkoxy, OH, Cl, F and CF$_3$; wherein alkyl and alkoxy are as defined above.

R10 and R11 are independently selected from H and alkyl or R10 and R11 together with the nitrogen atom to which they are attached form a 5- or 6-membered carbon containing heterocylic ring, optionally containing an addition N atom, which may be saturated or unsaturated with 1 or 2 double bonds, and optionally mono- or di-substituted with substituents selected from oxo, methyl, Cl and F; wherein alkyl is as defined above.

R10 and R11 together with the nitrogen atom to which they are attached form a 5- or 6-membered carbon containing heterocylic ring, optionally containing an addition N atom, which may be saturated or unsaturated with 1 or 2 double bonds, and optionally mono- or di-substituted with substituents selected from oxo, methyl, Cl and F.

R10 and R11 together with the nitrogen atom to which they are attached form a 6-membered carbon containing heterocylic ring, optionally containing an addition N atom, which may be saturated or unsaturated with 1 or 2 double bonds, and optionally may be oxo substituted.

R10 and R11 together with the nitrogen atom to which they are attached form a carbon-containing 5- or 6-membered saturated heterocylic ring.

R10 and R11 are independently selected from H and alkyl$^b$; wherein alkyl$^b$ is as defined above.

The present invention also encompasses, but is not limited to, the compounds listed below:

N-(3,5-Dimethoxybenzyl)-3-(methoxymethyl)-1-(4-((2-oxopyridin-1(2H)-yl)methyl)benzyl)-1H-pyrazole-4-carboxamide;

3-Amino-1-[4-(2-oxo-2H-pyridin-1-ylmethyl)-benzyl]-1H-pyrazole-4-carboxylic acid 2-fluoro-3-methoxy-benzylamide;

1-(7-Chloro-quinolin-3-ylmethyl)-3-methoxymethyl-1H-pyrazole-4-carboxylic acid 2-fluoro-3-methoxy-benzylamide;

N-[(2-fluoro-3-methoxyphenyl)methyl]-1-({4-[(4-methylpyrazol-1-yl)methyl]phenyl}methyl)-3-(trifluoromethyl)pyrazole-4-carboxamide;

N-[(3-methoxyphenyl)methyl]-1-({4-[(4-methylpyrazol-1-yl)methyl]phenyl}methyl)-3-(trifluoromethyl)pyrazole-4-carboxamide;

N-[(3-ethoxyphenyl)methyl]-1-({4-[(4-methylpyrazol-1-yl)methyl]phenyl}methyl)-3-(trifluoromethyl)pyrazole-4-carboxamide;

1-({4-[(4-methylpyrazol-1-yl)methyl]phenyl}methyl)-N-{[3-(trifluoromethoxy)phenyl]methyl}-3-(trifluoromethyl)pyrazole-4-carboxamide;

N-[(4-methylphenyl)methyl]-1-({4-[(4-methylpyrazol-1-yl)methyl]phenyl}methyl)-3-(trifluoromethyl)pyrazole-4-carboxamide;

N-[(2-fluoro-5-methoxyphenyl)methyl]-1-({4-[(4-methylpyrazol-1-yl)methyl]phenyl}methyl)-3-(trifluoromethyl)pyrazole-4-carboxamide;

N-[(2,4-dimethoxyphenyl)methyl]-1-({4-[(4-methylpyrazol-1-yl)methyl]phenyl}methyl)-3-(trifluoromethyl)pyrazole-4-carboxamide;

N-[(2,6-difluoro-4-methoxyphenyl)methyl]-1-({4-[(4-methylpyrazol-1-yl)methyl]phenyl}methyl)-3-(trifluoromethyl)pyrazole-4-carboxamide;

N-{[4-methoxy-2-(trifluoromethyl)phenyl]methyl}-1-({4-[(4-methylpyrazol-1-yl)methyl]phenyl}methyl)-3-(trifluoromethyl)pyrazole-4-carboxamide;

N-[(2,6-difluorophenyl)methyl]-1-({4-[(4-methylpyrazol-1-yl)methyl]phenyl}methyl)-3-(trifluoromethyl)pyrazole-4-carboxamide;

N-[(2-chloro-6-fluorophenyl)methyl]-1-({4-[(4-methylpyrazol-1-yl)methyl]phenyl}methyl)-3-(trifluoromethyl)pyrazole-4-carboxamide;

N-{[2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide;

N-[(4-chloro-2,6-difluorophenyl)methyl]-1-({4-[(4-methylpyrazol-1-yl)methyl]phenyl}methyl)-3-(trifluoromethyl)pyrazole-4-carboxamide;

N-[(4-chloro-2-fluorophenyl)methyl]-1-({4-[(4-methylpyrazol-1-yl)methyl]phenyl}methyl)-3-(trifluoromethyl)pyrazole-4-carboxamide;

N-[(3-chloro-2,6-difluorophenyl)methyl]-1-({4-[(4-methylpyrazol-1-yl)methyl]phenyl}methyl)-3-(trifluoromethyl)pyrazole-4-carboxamide;

N-[(3-chloro-2-fluorophenyl)methyl]-1-({4-[(4-methyl-pyrazol-1-yl)methyl]phenyl}methyl)-3-(trifluoromethyl)pyrazole-4-carboxamide;

N-[(5-chloro-2-fluorophenyl)methyl]-1-({4-[(4-methyl-pyrazol-1-yl)methyl]phenyl}methyl)-3-(trifluoromethyl)pyrazole-4-carboxamide;

N-{[3-chloro-2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide;

N-[(2,6-dichlorophenyl)methyl]-1-({4-[(4-methylpyrazol-1-yl)methyl]phenyl}methyl)-3-(trifluoromethyl)pyrazole-4-carboxamide;

N-{[5-chloro-2-(trifluoromethyl)phenyl]methyl}-1-({4-[(4-methylpyrazol-1-yl)methyl]phenyl}methyl)-3-(trifluoromethyl)pyrazole-4-carboxamide;

N-[(2,4-dimethyl phenyl)methyl]-1-({4-[(4-methylpyrazol-1-yl)methyl]phenyl}methyl)-3-(trifluoromethyl)pyrazole-4-carboxamide;

N-[(2,6-dimethyl phenyl)methyl]-1-({4-[(4-methylpyrazol-1-yl)methyl]phenyl}methyl)-3-(trifluoromethyl)pyrazole-4-carboxamide;

1-({4-[(4-methylpyrazol-1-yl)methyl]phenyl}methyl)-3-(trifluoromethyl)-N-[(2,4,6-trimethyl phenyl)methyl]pyrazole-4-carboxamide;

N-[(3-fluoro-2-methyl phenyl)methyl]-1-({4-[(4-methyl-pyrazol-1-yl)methyl]phenyl}methyl)-3-(trifluoromethyl)pyrazole-4-carboxamide;

N-[(2-fluoro-4-methyl phenyl)methyl]-1-({4-[(4-methyl-pyrazol-1-yl)methyl]phenyl}methyl)-3-(trifluoromethyl)pyrazole-4-carboxamide;

N-[(3-fluoropyridin-2-yl)methyl]-1-({4-[(4-methylpyrazol-1-yl)methyl]phenyl}methyl)-3-(trifluoromethyl)pyrazole-4-carboxamide;

N-[(4-chloropyridin-2-yl)methyl]-1-({4-[(4-methylpyrazol-1-yl)methyl]phenyl}methyl)-3-(trifluoromethyl)pyrazole-4-carboxamide;

3-(methoxymethyl)-1-({4-[(2-oxopyridin-1-yl)methyl]phenyl}methyl)-N-{[4-(trifluoromethyl)pyridin-3-yl]methyl}pyrazole-4-carboxamide;

3-(methoxymethyl)-N-[(6-methyl pyridin-3-yl)methyl]-1-({4-[(2-oxopyridin-1-yl)methyl]phenyl}methyl)pyrazole-4-carboxamide;

N-[(4-fluoro-5-methoxypyridin-3-yl)methyl]-3-(methoxymethyl)-1-({4-[(2-oxopyridin-1-yl)methyl]phenyl}methyl)pyrazole-4-carboxamide;

N-[(4-acetamidopyridin-3-yl)methyl]-3-(methoxymethyl)-1-({4-[(2-oxopyridin-1-yl)methyl]phenyl}methyl)pyrazole-4-carboxamide;

N-{[4-fluoro-2-(trifluoromethyl)pyridin-3-yl]methyl}-3-(methoxymethyl)-1-({4-[(2-oxopyridin-1-yl)methyl]phenyl}methyl)pyrazole-4-carboxamide;

3-(methoxymethyl)-1-({4-[(2-oxopyridin-1-yl)methyl]phenyl}methyl)-N-{[2-(trifluoromethyl)pyridin-3-yl]methyl}pyrazole-4-carboxamide;

3-(methoxymethyl)-1-({4-[(2-oxopyridin-1-yl)methyl]phenyl}methyl)-N-{[4-(trifluoromethyl)pyridin-3-yl]methyl}pyrazole-4-carboxamide;

N-[(4-fluoropyridin-3-yl)methyl]-3-(methoxymethyl)-1-({4-[(2-oxopyridin-1-yl)methyl]phenyl}methyl)pyrazole-4-carboxamide;

3-(methoxymethyl)-N-[(6-methyl pyridin-3-yl)methyl]-1-({4-[(2-oxopyridin-1-yl)methyl]phenyl}methyl)pyrazole-4-carboxamide;

3-(methoxymethyl)-N-[(6-methoxypyridin-2-yl)methyl]-1-({4-[(2-oxopyridin-1-yl)methyl]phenyl}methyl)pyrazole-4-carboxamide;

N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide;

N-[(3-fluoro-6-methoxypyridin-2-yl)methyl]-3-(methoxymethyl)-1-({4-[(2-oxopyridin-1-yl)methyl]phenyl}methyl)pyrazole-4-carboxamide;

N-[(3-chlorothiophen-2-yl)methyl]-3-(methoxymethyl)-1-({4-[(2-oxopyridin-1-yl)methyl]phenyl}methyl)pyrazole-4-carboxamide;

N-[(3-chloro-5-methylthiophen-2-yl)methyl]-3-(methoxymethyl)-1-({4-[(2-oxopyridin-1-yl)methyl]phenyl}methyl)pyrazole-4-carboxamide;

N-[(5-chloro-1-benzothiophen-3-yl)methyl]-3-(methoxymethyl)-1-({4-[(2-oxopyridin-1-yl)methyl]phenyl}methyl)pyrazole-4-carboxamide;

N-[(5-chloro-1-benzothiophen-3-yl)methyl]-3-(methoxymethyl)-1-{[6-(pyrrolidin-1-yl)pyridin-3-yl]methyl}pyrazole-4-carboxamide;

N-[(5-chloro-1-benzothiophen-3-yl)methyl]-3-(methoxymethyl)-1-({4-[(4-methylpyrazol-1-yl)methyl]phenyl}methyl)pyrazole-4-carboxamide;

N-[(2-carbamoylphenyl)methyl]-3-cyclopropyl-1-({4-[(2-oxopyridin-1-yl)methyl]phenyl}methyl)pyrazole-4-carboxamide;

N-[(3-carbamoylphenyl)methyl]-3-cyclopropyl-1-({4-[(2-oxopyridin-1-yl)methyl]phenyl}methyl)pyrazole-4-carboxamide;

N-[(4-carbamoylphenyl)methyl]-3-cyclopropyl-1-({4-[(2-oxopyridin-1-yl)methyl]phenyl}methyl)pyrazole-4-carboxamide;

N-{[2-fluoro-6-(trifluoromethyl)phenyl]methyl}-1-({4-[(2-oxopyridin-1-yl)methyl]phenyl}methyl)-3-(trifluoromethyl)pyrazole-4-carboxamide;

3-cyclopropyl-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(methoxymethyl)-1-({4-[(2-oxopyridin-1-yl)methyl]phenyl}methyl)pyrazole-4-carboxamide;

N-[(2-fluoro-3,6-dimethoxyphenyl)methyl]-3-(methoxymethyl)-1-({4-[(2-oxopyridin-1-yl)methyl]phenyl}methyl)pyrazole-4-carboxamide;

N-[(2-fluoro-3-methoxyphenyl)methyl]-3-(methylamino)-1-({4-[(2-oxopyridin-1-yl)methyl]phenyl}methyl)pyrazole-4-carboxamide;

3-(ethylamino)-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(isopropylamino)-1-({4-[(2-oxopyridin-1-yl)methyl]phenyl}methyl)pyrazole-4-carboxamide;

3-amino-1-({4-[(2-oxopyridin-1-yl)methyl]phenyl}methyl)-N-{[4-(trifluoromethoxy)phenyl]methyl}pyrazole-4-carboxamide;

3-(dimethylamino)-N-[(2-fluoro-3-methoxyphenyl)methyl]-1-({4-[(2-oxopyridin-1-yl)methyl]phenyl}methyl)pyrazole-4-carboxamide;

3-amino-N-[(2,6-difluoro-3-methoxyphenyl)methyl]-1-({4-[(2-oxopyridin-1-yl)methyl]phenyl}methyl)pyrazole-4-carboxamide;

N-[(2,6-difluoro-3-methoxyphenyl)methyl]-3-(methylamino)-1-({4-[(2-oxopyridin-1-yl)methyl]phenyl}methyl)pyrazole-4-carboxamide;

N-[(2-fluorophenyl)methyl]-3-(methoxymethyl)-1-({4-[(2-oxopyridin-1-yl)methyl]phenyl}methyl)pyrazole-4-carboxamide;

3-(methoxymethyl)-1-({4-[(2-oxopyridin-1-yl)methyl]phenyl}methyl)-N-{[2-(trifluoromethyl)phenyl]methyl}pyrazole-4-carboxamide;

N-[(2-fluoro-5-methoxyphenyl)methyl]-3-(methoxymethyl)-1-({4-[(2-oxopyridin-1-yl)methyl]phenyl}methyl)pyrazole-4-carboxamide;

N-[(2-fluoro-4-methylphenyl)methyl]-3-(methoxymethyl)-1-({4-[(2-oxopyridin-1-yl)methyl]phenyl}methyl)pyrazole-4-carboxamide;

N-[(2,6-difluoro-3-methoxyphenyl)methyl]-3-(methoxymethyl)-1-({4-[(2-oxopyridin-1-yl)methyl]phenyl}methyl)pyrazole-4-carboxamide;

N-[(3-chloro-5-methoxyphenyl)methyl]-3-(methoxymethyl)-1-({4-[(2-oxopyridin-1-yl)methyl]phenyl}methyl)pyrazole-4-carboxamide;

N-{[2-(difluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-3-methoxyphenyl]methyl}-3-(methoxymethyl)-1-({4-[(2-oxopyridin-1-yl)methyl]phenyl}methyl)pyrazole-4-carboxamide;

3-amino-N-{[2-fluoro-6-(trifluoromethyl)phenyl]methyl}-1-({4-[(2-oxopyridin-1-yl)methyl]phenyl}methyl)pyrazole-4-carboxamide;

3-acetamido-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(N-methylacetamido)-1-({4-[(2-oxopyridin-1-yl)methyl]phenyl}methyl)pyrazole-4-carboxamide;

N-[(3-chloro-2,6-difluorophenyl)methyl]-3-(methoxymethyl)-1-({4-[(2-oxopyridin-1-yl)methyl]phenyl}methyl)pyrazole-4-carboxamide;

N-[(2-fluoro-3-methoxy-4-methylphenyl)methyl]-3-(methoxymethyl)-1-({4-[(2-oxopyridin-1-yl)methyl]phenyl}methyl)pyrazole-4-carboxamide;

N-[(2-cyano-5-methoxyphenyl)methyl]-3-(methoxymethyl)-1-({4-[(2-oxopyridin-1-yl)methyl]phenyl}methyl)pyrazole-4-carboxamide;

N-[(5-chloro-2-cyanophenyl)methyl]-3-(methoxymethyl)-1-({4-[(2-oxopyridin-1-yl)methyl]phenyl}methyl)pyrazole-4-carboxamide;

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide;

N-{[3-methoxy-2-(trifluoromethyl)phenyl]methyl}-3-(methoxymethyl)-1-({4-[(2-oxopyridin-1-yl)methyl]phenyl}methyl)pyrazole-4-carboxamide;

N-{[5-methoxy-2-(trifluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluorophenyl]methyl}-3-(methoxymethyl)-1-({4-[(2-oxopyridin-1-yl)methyl]phenyl}methyl)pyrazole-4-carboxamide;

N-{[2-(difluoromethyl)-5-methoxyphenyl]methyl}-3-(methoxymethyl)-1-({4-[(2-oxopyridin-1-yl)methyl]phenyl}methyl)pyrazole-4-carboxamide;

N-{[6-(difluoromethyl)-2-fluoro-3-methoxyphenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluoro-3-methoxyphenyl]methyl}-3-(methoxymethyl)-1-({4-[(2-oxopyridin-1-yl)methyl]phenyl}methyl)pyrazole-4-carboxamide;

N-[(2-chloro-5-methoxyphenyl)methyl]-3-(methoxymethyl)-1-({4-[(2-oxopyridin-1-yl)methyl]phenyl}methyl)pyrazole-4-carboxamide;

N-[(2-carbamoyl-6-fluorophenyl)methyl]-3-(methoxymethyl)-1-({4-[(2-oxopyridin-1-yl)methyl]phenyl}methyl)pyrazole-4-carboxamide;

N-[(2-carbamoyl-5-methoxyphenyl)methyl]-3-(methoxymethyl)-1-({4-[(2-oxopyridin-1-yl)methyl]phenyl}methyl)pyrazole-4-carboxamide;

2-({[3-(methoxymethyl)-1-({4-[(2-oxopyridin-1-yl)methyl]phenyl}methyl)pyrazol-4-yl]formamido}methyl)benzoic acid N-{[2-fluoro-6-(1,2,3,4-tetrazol-1-yl)phenyl]methyl}-3-(methoxymethyl)-1-({4-[(2-oxopyridin-1-yl)methyl]phenyl}methyl)pyrazole-4-carboxamide;

N-{[2-fluoro-5-(1,2,3,4-tetrazol-1-yl)phenyl]methyl}-3-(methoxymethyl)-1-({4-[(2-oxopyridin-1-yl)methyl]phenyl}methyl)pyrazole-4-carboxamide;

N-{[3-(difluoromethoxy)-2-fluorophenyl]methyl}-3-(methoxymethyl)-1-({4-[(2-oxopyridin-1-yl)methyl]phenyl}methyl)pyrazole-4-carboxamide;

N-{[3-(difluoromethoxy)phenyl]methyl}-3-(methoxymethyl)-1-({4-[(2-oxopyridin-1-yl)methyl]phenyl}methyl)pyrazole-4-carboxamide;

N-{[2-(difluoromethoxy)-6-fluorophenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluoro-4-methylphenyl]methyl}-3-(methoxymethyl)-1-({4-[(2-oxopyridin-1-yl)methyl]phenyl}methyl)pyrazole-4-carboxamide;

N-[(2,5-difluorophenyl)methyl]-3-(methoxymethyl)-1-({4-[(2-oxopyridin-1-yl)methyl]phenyl}methyl)pyrazole-4-carboxamide;

N-[(3-fluoro-5-methoxyphenyl)methyl]-3-(methoxymethyl)-1-({4-[(2-oxopyridin-1-yl)methyl]phenyl}methyl)pyrazole-4-carboxamide;

N-[(2,5-difluoro-3-methoxyphenyl)methyl]-3-(methoxymethyl)-1-({4-[(2-oxopyridin-1-yl)methyl]phenyl}methyl)pyrazole-4-carboxamide;

N-[(2-fluoro-6-methylphenyl)methyl]-3-(methoxymethyl)-1-({4-[(2-oxopyridin-1-yl)methyl]phenyl}methyl)pyrazole-4-carboxamide;

N-[(5-chloro-2-fluoro-3-methoxyphenyl)methyl]-3-(methoxymethyl)-1-({4-[(2-oxopyridin-1-yl)methyl]phenyl}methyl)pyrazole-4-carboxamide;

N-[(6-chloro-2-fluoro-3-methoxyphenyl)methyl]-3-(methoxymethyl)-1-({4-[(2-oxopyridin-1-yl)methyl]phenyl}methyl)pyrazole-4-carboxamide;

N-{[2-fluoro-3-methoxy-6-(trifluoromethyl)phenyl]methyl}-3-(methoxymethyl)-1-({4-[(2-oxopyridin-1-yl)methyl]phenyl}methyl)pyrazole-4-carboxamide;

N-{[2-fluoro-4-methyl-6-(trifluoromethyl)phenyl]methyl}-3-(methoxymethyl)-1-({4-[(2-oxopyridin-1-yl)methyl]phenyl}methyl)pyrazole-4-carboxamide;

N-{[4-chloro-2-fluoro-6-(trifluoromethyl)phenyl]methyl}-3-(methoxymethyl)-1-({4-[(2-oxopyridin-1-yl)methyl]phenyl}methyl)pyrazole-4-carboxamide;

3-cyano-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-hydroxyphenyl)methyl]-3-(methoxymethyl)-1-({4-[(2-oxopyridin-1-yl)methyl]phenyl}methyl)pyrazole-4-carboxamide;

3-amino-N-[(2-fluoro-3-hydroxyphenyl)methyl]-1-({4-[(2-oxopyridin-1-yl)methyl]phenyl}methyl)pyrazole-4-carboxamide;

methyl 2-({[3-(methoxymethyl)-1-({4-[(2-oxopyridin-1-yl)methyl]phenyl}methyl)pyrazol-4-yl]formamido}methyl)benzoate N-[(3-ethyl-2-fluorophenyl)methyl]-3-(methoxymethyl)-1-({4-[(2-oxopyridin-1-yl)methyl]phenyl}methyl)pyrazole-4-carboxamide;

3-(methoxymethyl)-N-[(3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(methoxymethyl)-1-({4-[(2-oxopyrazin-1-yl)methyl]phenyl}methyl)pyrazole-4-carboxamide;

N-[(2,6-difluoro-3-methoxyphenyl)methyl]-1-({4-[(4-fluoro-2-oxopyridin-1-yl)methyl]phenyl}methyl)-3-(methoxymethyl)pyrazole-4-carboxamide;

N-[(2,6-difluoro-3-methoxyphenyl)methyl]-3-(methoxymethyl)-1-({4-[(4-methyl-2-oxopyridin-1-yl)methyl]phenyl}methyl)pyrazole-4-carboxamide;

1-({4-[(5-fluoro-2-oxopyridin-1-yl)methyl]phenyl}methyl)-N-[(2-fluoro-3-methoxyphenyl)methyl]-3-(methoxymethyl)pyrazole-4-carboxamide;

N-[(2,6-difluoro-3-methoxyphenyl)methyl]-1-({4-[(5-fluoro-2-oxopyridin-1-yl)methyl]phenyl}methyl)-3-(methoxymethyl)pyrazole-4-carboxamide;

N-[(2,6-difluoro-3-methoxyphenyl)methyl]-1-({4-[(4-ethoxy-2-oxopyridin-1-yl)methyl]phenyl}methyl)-3-(methoxymethyl)pyrazole-4-carboxamide;

N-[(2-fluoro-3-methoxyphenyl)methyl]-1-({4-[(5-methoxy-4-methylpyrazol-1-yl)methyl]phenyl}methyl)-3-(methoxymethyl)pyrazole-4-carboxamide;

N-[(2-fluoro-3-methoxyphenyl)methyl]-3-(methoxymethyl)-1-{[5-(2-oxopyridin-1-yl)thiophen-3-yl]methyl}pyrazole-4-carboxamide;

N-[(2-fluoro-3-methoxyphenyl)methyl]-3-(methoxymethyl)-1-({5-[(2-oxopyridin-1-yl)methyl]thiophen-3-yl}methyl)pyrazole-4-carboxamide;

3-amino-N-[(2-fluoro-3-methoxyphenyl)methyl]-1-({4-[(4-methylpyrazol-1-yl)methyl]phenyl}methyl)pyrazole-4-carboxamide;

3-methoxymethyl-1-[4-(4-methyl-pyrazol-1-ylmethyl)-benzyl]-1H-pyrazole-4-carboxylic acid 6-cyano-2-fluoro-3-methoxy-benzylamide;

3-methoxymethyl-1-(2-pyrrolidin-1-yl-pyrimidin-5-ylmethyl)-1H-pyrazole-4-carboxylic acid 6-cyano-2-fluoro-3-methoxy-benzylamide;

1-(2-pyrrolidin-1-yl-pyrimidin-5-ylmethyl)-3-trifluoromethyl-1H-pyrazole-4-carboxylic acid 6-cyano-2-fluoro-3-methoxy-benzylamide;

N-[(2-fluoro-3-methoxyphenyl)methyl]-1-({4-[(2-fluoro-6-oxopyridin-1-yl)methyl]phenyl}methyl)-3-(methoxymethyl)pyrazole-4-carboxamide;

1-({4-[(2-chloro-6-oxopyridin-1-yl)methyl]phenyl}methyl)-N-[(2-fluoro-3-methoxyphenyl)methyl]-3-(methoxymethyl)pyrazole-4-carboxamide;

N-[(2,6-difluoro-3-methoxyphenyl)methyl]-3-(methoxymethyl)-1-({2-[(methylamino)methyl]phenyl}methyl)pyrazole-4-carboxamide;

N-[(2,6-difluoro-3-methoxyphenyl)methyl]-3-(methoxymethyl)-1-{[2-(methylamino)pyridin-4-yl]methyl}pyrazole-4-carboxamide;

N-[(2-fluoro-3-methoxyphenyl)methyl]-3-(methoxymethyl)-1-{[2-(2,2,2-trifluoroethyl)phenyl]methyl}pyrazole-4-carboxamide;

N-[(2-fluoro-3-methoxyphenyl)methyl]-3-(methoxymethyl)-1-{[2-(trifluoromethoxy)phenyl]methyl}pyrazole-4-carboxamide;

N-[(2-fluoro-3-methoxyphenyl)methyl]-2-methyl-1-({4-[(2-oxopyridin-1-yl)methyl]phenyl}methyl)imidazole-4-carboxamide;

2-amino-N-[(2-fluoro-3-methoxyphenyl)methyl]-1-({4-[(2-oxopyridin-1-yl)methyl]phenyl}methyl)imidazole-4-carboxamide;

2-cyclopropyl-N-[(2-fluoro-3-methoxyphenyl)methyl]-1-({4-[(2-oxopyridin-1-yl)methyl]phenyl}methyl)imidazole-4-carboxamide;

N-[(2-fluoro-3-methoxyphenyl)methyl]-1-({4-[(2-oxopyridin-1-yl)methyl]phenyl}methyl)-2-(trifluoromethyl)imidazole-4-carboxamide;

N-[(2-fluoro-3-methoxyphenyl)methyl]-2-(methoxymethyl)-1-({4-[(2-oxopyridin-2-yl)methyl]phenyl}methyl)imidazole-4-carboxamide;

N-[(2-fluoro-3-methoxyphenyl)methyl]-1-{[6-(pyrrolidin-1-yl)pyridin-3-yl]methyl}-3-(trifluoromethyl)pyrazole-4-carboxamide;

3-amino-N-[(2-fluoro-3-methoxyphenyl)methyl]-1-{[6-(pyrrolidin-1-yl)pyridin-3-yl]methyl}pyrazole-4-carboxamide;

N-[(2-fluoro-3-methoxyphenyl)methyl]-3-(methoxymethyl)-1-{[6-(pyrrolidin-1-yl)pyridin-3-yl]methyl}pyrazole-4-carboxamide;

3-methoxymethyl-1-(6-pyrrolidin-1-yl-pyridin-3-ylmethyl)-1H-pyrazole-4-carboxylic acid 6-cyano-2-fluoro-3-methoxy-benzylamide;

1-(6-pyrrolidin-1-yl-pyridin-3-ylmethyl)-3-trifluoromethyl-1H-pyrazole-4-carboxylic acid 6-cyano-2-fluoro-3-methoxy-benzylamide;

3-amino-N-[(7-chloro-4-methyl-2,3-dihydro-1,4-benzoxazin-2-yl)methyl]-1-({4-[(2-oxopyridin-1-yl)methyl]phenyl}methyl)pyrazole-4-carboxamide;

3-amino-N-[(7-chloro-3,4-dihydro-2H-1,4-benzoxazin-2-yl)methyl]-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-Amino-1-[4-(2-oxo-2H-pyridin-1-ylmethyl)-benzyl]-1H-pyrazole-4-carboxylic acid 2-fluoro-3-methoxy-benzylamide;

N-[(2-fluoro-3-methoxyphenyl)methyl]-1-({4-[(4-methylpyrazol-1-yl)methyl]phenyl}methyl)-3-(trifluoromethyl)pyrazole-4-carboxamide;

N-[(2-fluoro-5-methoxyphenyl)methyl]-1-({4-[(4-methylpyrazol-1-yl)methyl]phenyl}methyl)-3-(trifluoromethyl)pyrazole-4-carboxamide;

N-{[2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide;

N-[(4-chloro-2,6-difluorophenyl)methyl]-1-({4-[(4-methylpyrazol-1-yl)methyl]phenyl}methyl)-3-(trifluoromethyl)pyrazole-4-carboxamide;

N-{[3-chloro-2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide;

N-[(2-fluoro-4-methyl phenyl)methyl]-1-({4-[(4-methylpyrazol-1-yl)methyl]phenyl}methyl)-3-(trifluoromethyl)pyrazole-4-carboxamide;

N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide;

N-[(5-chloro-1-benzothiophen-3-yl)methyl]-3-(methoxymethyl)-1-({4-[(2-oxopyridin-1-yl)methyl]phenyl}methyl)pyrazole-4-carboxamide;

N-{[2-fluoro-6-(trifluoromethyl)phenyl]methyl}-1-({4-[(2-oxopyridin-1-yl)methyl]phenyl}methyl)-3-(trifluoromethyl)pyrazole-4-carboxamide;

3-cyclopropyl-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(methoxymethyl)-1-({4-[(2-oxopyridin-1-yl)methyl]phenyl}methyl)pyrazole-4-carboxamide;

N-[(2-fluoro-3,6-dimethoxyphenyl)methyl]-3-(methoxymethyl)-1-({4-[(2-oxopyridin-1-yl)methyl]phenyl}methyl)pyrazole-4-carboxamide;

3-(dimethylamino)-N-[(2-fluoro-3-methoxyphenyl)methyl]-1-({4-[(2-oxopyridin-1-yl)methyl]phenyl}methyl)pyrazole-4-carboxamide;

N-[(2-fluoro-5-methoxyphenyl)methyl]-3-(methoxymethyl)-1-({4-[(2-oxopyridin-1-yl)methyl]phenyl}methyl)pyrazole-4-carboxamide;

N-[(2-fluoro-4-methyl phenyl)methyl]-3-(methoxymethyl)-1-({4-[(2-oxopyridin-1-yl)methyl]phenyl}methyl)pyrazole-4-carboxamide;

N-[(2,6-difluoro-3-methoxyphenyl)methyl]-3-(methoxymethyl)-1-({4-[(2-oxopyridin-1-yl)methyl]phenyl}methyl)pyrazole-4-carboxamide;

N-{[2-(difluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-3-methoxyphenyl]methyl}-3-(methoxymethyl)-1-({4-[(2-oxopyridin-1-yl)methyl]phenyl}methyl)pyrazole-4-carboxamide;

3-amino-N-{[2-fluoro-6-(trifluoromethyl)phenyl]methyl}-1-({4-[(2-oxopyridin-1-yl)methyl]phenyl}methyl)pyrazole-4-carboxamide;

3-acetamido-N-[(2-fluoro-3-methoxyphenyl)methyl]-1-({4-[(2-oxopyridin-1-yl)methyl]phenyl}methyl)pyrazole-4-carboxamide;

N-[(3-chloro-2,6-difluorophenyl)methyl]-3-(methoxymethyl)-1-({4-[(2-oxopyridin-1-yl)methyl]phenyl}methyl)pyrazole-4-carboxamide;

N-[(5-chloro-2-cyanophenyl)methyl]-3-(methoxymethyl)-1-({4-[(2-oxopyridin-1-yl)methyl]phenyl}methyl)pyrazole-4-carboxamide;

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide;

N-{[5-methoxy-2-(trifluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluorophenyl]methyl}-3-(methoxymethyl)-1-({4-[(2-oxopyridin-1-yl)methyl]phenyl}methyl)pyrazole-4-carboxamide;

N-{[2-(difluoromethyl)-5-methoxyphenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluoro-3-methoxyphenyl]methyl}-3-(methoxymethyl)-1-({4-[(2-oxopyridin-1-yl)methyl]phenyl}methyl)pyrazole-4-carboxamide;

N-[(2-carbamoyl-6-fluorophenyl)methyl]-3-(methoxymethyl)-1-({4-[(2-oxopyridin-1-yl)methyl]phenyl}methyl)pyrazole-4-carboxamide;

N-[(2-carbamoyl-5-methoxyphenyl)methyl]-3-(methoxymethyl)-1-({4-[(2-oxopyridin-1-yl)methyl]phenyl}methyl)pyrazole-4-carboxamide;

N-{[3-(difluoromethoxy)-2-fluorophenyl]methyl}-3-(methoxymethyl)-1-({4-[(2-oxopyridin-1-yl)methyl]phenyl}methyl)pyrazole-4-carboxamide;

N-{[2-(difluoromethoxy)-6-fluorophenyl]methyl}-3-(methoxymethyl)-1-({4-[(2-oxopyridin-1-yl)methyl]phenyl}methyl)pyrazole-4-carboxamide;

N-[(2,5-difluoro-3-methoxyphenyl)methyl]-3-(methoxymethyl)-1-({4-[(2-oxopyridin-1-yl)methyl]phenyl}methyl)pyrazole-4-carboxamide;

N-[(2-fluoro-6-methylphenyl)methyl]-3-(methoxymethyl)-1-({4-[(2-oxopyridin-1-yl)methyl]phenyl}methyl)pyrazole-4-carboxamide;

N-[(6-chloro-2-fluoro-3-methoxyphenyl)methyl]-3-(methoxymethyl)-1-({4-[(2-oxopyridin-1-yl)methyl]phenyl}methyl)pyrazole-4-carboxamide;

3-amino-N-[(2-fluoro-3-hydroxyphenyl)methyl]-1-({4-[(2-oxopyridin-1-yl)methyl]phenyl}methyl)pyrazole-4-carboxamide;

N-[(3-ethyl-2-fluorophenyl)methyl]-3-(methoxymethyl)-1-({4-[(2-oxopyridin-1-yl)methyl]phenyl}methyl)pyrazole-4-carboxamide;

3-(methoxymethyl)-N-[(3-methoxyphenyl)methyl]-1-({4-[(2-oxopyridin-1-yl)methyl]phenyl}methyl)pyrazole-4-carboxamide;

N-[(2,6-difluoro-3-methoxyphenyl)methyl]-3-(methoxymethyl)-1-({4-[(4-methyl-2-oxopyridin-1-yl)methyl]phenyl}methyl)pyrazole-4-carboxamide;

N-[(2,6-difluoro-3-methoxyphenyl)methyl]-1-({4-[(5-fluoro-2-oxopyridin-1-yl)methyl]phenyl}methyl)-3-(methoxymethyl)pyrazole-4-carboxamide;

N-[(2-fluoro-3-methoxyphenyl)methyl]-2-methyl-1-({4-[(2-oxopyridin-1-yl)methyl]phenyl}methyl)imidazole-4-carboxamide;

N-[(2-fluoro-3-methoxyphenyl)methyl]-1-({4-[(2-oxopyridin-1-yl)methyl]phenyl}methyl)-2-(trifluoromethyl)imidazole-4-carboxamide;

3-amino-N-[(7-chloro-4-methyl-2,3-dihydro-1,4-benzoxazin-2-yl)methyl]-1-({4-[(2-oxopyridin-1-yl)methyl]phenyl}methyl)pyrazole-4-carboxamide;

3-amino-N-[(7-chloro-3,4-dihydro-2H-1,4-benzoxazin-2-yl)methyl]-1-({4-[(2-oxopyridin-1-yl)methyl]phenyl}methyl)pyrazole-4-carboxamide;

and pharmaceutically acceptable salts and solvates thereof.

The present invention also encompasses, but is not limited to, the compounds listed below:

3-Amino-1-[4-(2-oxo-2H-pyridin-1-ylmethyl)-benzyl]-1H-pyrazole-4-carboxylic acid 2-fluoro-3-methoxy-benzylamide;

N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide;

N-{[2-fluoro-6-(trifluoromethyl)phenyl]methyl}-1-({4-[(2-oxopyridin-1-yl)methyl]phenyl}methyl)-3-(trifluoromethyl)pyrazole-4-carboxamide;

3-cyclopropyl-N-[(2-fluoro-3-methoxyphenyl)methyl]-1-({4-[(2-oxopyridin-1-yl)methyl]phenyl}methyl)pyrazole-4-carboxamide;

N-[(2-fluoro-3-methoxyphenyl)methyl]-3-(methoxymethyl)-1-({4-[(2-oxopyridin-1-yl)methyl]phenyl}methyl)pyrazole-4-carboxamide;

N-[(2-fluoro-3,6-dimethoxyphenyl)methyl]-3-(methoxymethyl)-1-({4-[(2-oxopyridin-1-yl)methyl]phenyl}methyl)pyrazole-4-carboxamide;

3-(dimethylamino)-N-[(2-fluoro-3-methoxyphenyl)methyl]-1-({4-[(2-oxopyridin-1-yl)methyl]phenyl}methyl)pyrazole-4-carboxamide;

N-[(2-fluoro-5-methoxyphenyl)methyl]-3-(methoxymethyl)-1-({4-[(2-oxopyridin-1-yl)methyl]phenyl}methyl)pyrazole-4-carboxamide;

N-[(2-fluoro-4-methyl phenyl)methyl]-3-(methoxymethyl)-1-({4-[(2-oxopyridin-1-yl)methyl]phenyl}methyl)pyrazole-4-carboxamide;

N-[(2,6-difluoro-3-methoxyphenyl)methyl]-3-(methoxymethyl)-1-({4-[(2-oxopyridin-1-yl)methyl]phenyl}methyl)pyrazole-4-carboxamide;

N-{[2-(difluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-3-methoxyphenyl]methyl}-3-(methoxymethyl)-1-({4-[(2-oxopyridin-1-yl)methyl]phenyl}methyl)pyrazole-4-carboxamide;

3-amino-N-{[2-fluoro-6-(trifluoromethyl)phenyl]methyl}-1-({4-[(2-oxopyridin-1-yl)methyl]phenyl}methyl)pyrazole-4-carboxamide;

N-[(5-chloro-2-cyanophenyl)methyl]-3-(methoxymethyl)-1-({4-[(2-oxopyridin-1-yl)methyl]phenyl}methyl)pyrazole-4-carboxamide;

N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide;

N-{[5-methoxy-2-(trifluoromethyl)phenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluorophenyl]methyl}-3-(methoxymethyl)-1-({4-[(2-oxopyridin-1-yl)methyl]phenyl}methyl)pyrazole-4-carboxamide;

N-{[2-(difluoromethyl)-5-methoxyphenyl]methyl}-3-(methoxymethyl)-1-({4-[(2-oxopyridin-1-yl)methyl]phenyl}methyl)pyrazole-4-carboxamide;

N-{[2-(difluoromethyl)-6-fluoro-3-methoxyphenyl]methyl}-3-(methoxymethyl)-1-({4-[(2-oxopyridin-1-yl)methyl]phenyl}methyl)pyrazole-4-carboxamide;

N-[(2-carbamoyl-6-fluorophenyl)methyl]-3-(methoxymethyl)-1-({4-[(2-oxopyridin-1-yl)methyl]phenyl}methyl)pyrazole-4-carboxamide;

N-[(2-carbamoyl-5-methoxyphenyl)methyl]-3-(methoxymethyl)-1-({4-[(2-oxopyridin-1-yl)methyl]phenyl}methyl)pyrazole-4-carboxamide;

N-{[2-(difluoromethoxy)-6-fluorophenyl]methyl}-3-(methoxymethyl)-1-({4-[(2-oxopyridin-1-yl)methyl]phenyl}methyl)pyrazole-4-carboxamide;

N-[(2,5-difluoro-3-methoxyphenyl)methyl]-3-(methoxymethyl)-1-({4-[(2-oxopyridin-1-yl)methyl]phenyl}methyl)pyrazole-4-carboxamide;

N-[(6-chloro-2-fluoro-3-methoxyphenyl)methyl]-3-(methoxymethyl)-1-({4-[(2-oxopyridin-1-yl)methyl]phenyl}methyl)pyrazole-4-carboxamide;

3-(methoxymethyl)-N-[(3-methoxyphenyl)methyl]-1-({4-[(2-oxopyridin-1-yl)methyl]phenyl}methyl)pyrazole-4-carboxamide;

N-[(2,6-difluoro-3-methoxyphenyl)methyl]-1-({4-[(5-fluoro-2-oxopyridin-1-yl)methyl]phenyl}methyl)-3-(methoxymethyl)pyrazole-4-carboxamide;

N-[(2-fluoro-3-methoxyphenyl)methyl]-2-methyl-1-({4-[(2-oxopyridin-1-yl)methyl]phenyl}methyl)imidazole-4-carboxamide;

3-amino-N-[(7-chloro-4-methyl-2,3-dihydro-1,4-benzoxazin-2-yl)methyl]-1-({4-[(2-oxopyridin-1-yl)methyl]phenyl}methyl)pyrazole-4-carboxamide;

3-amino-N-[(7-chloro-3,4-dihydro-2H-1,4-benzoxazin-2-yl)methyl]-1-({4-[(2-oxopyridin-1-yl)methyl]phenyl}methyl)pyrazole-4-carboxamide and pharmaceutically acceptable salts and solvates thereof.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, the disease or condition in which plasma kallikrein activity is implicated is selected from impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In a preferred aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in Retina, 2009 June; 29(6 Suppl): S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Definitions

The term "alkyl" includes saturated hydrocarbon residues including:

linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.

branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

each optionally substituted as stated above.

Cycloalkyl is a monocyclic saturated hydrocarbon of between 3 and 7 carbon atoms, or between 3 and 6 carbon atoms, or between 3 and 5 carbon atoms. Optionally, cycloalkyl may be substituted with a substituent selected from alkyl, alkoxy and NR12R13; wherein R12 and R13 are independently selected from H and alkyl or R12 and R13 together with the nitrogen to which they are attached form a 4-, 5-, 6- or 7-membered heterocylic ring which may be saturated or unsaturated with 1 or 2 double bonds and which may be optionally mono- or di-substituted with substituents selected from oxo, alkyl, alkoxy, OH, F and $CF_3$. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

The term "alkoxy" includes O-linked hydrocarbon residues including:

linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.

each optionally substituted as stated above.

Unless otherwise stated, halo is selected from Cl, F, Br and I.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (wherein said substituents are selected from those stated above) and naphthyl.

Heteroaryl is as defined above. Typically, heteroaryl will be optionally substituted with 1, 2 or 3 substituents. Optional substituents are selected from those stated above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

The term "N-linked", such as in "N-linked pyrrolidinyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —$(CH_2)_{1-3}$-aryl, "-" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and transforms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

Unless otherwise stated, the compounds of the invention include compounds that differ only in the presence of one or more isotopically enriched atoms. For example, compounds wherein hydrogen is replaced by deuterium or tritium, or wherein carbon is replaced by $^{13}C$ or $^{14}C$, are within the scope of the present invention. Such compounds are useful, for example, as analytical tools or probes in biological assays.

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intra-vitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvent. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

Examples of synthetic methods that may be used to prepare 4-carboxyimidazoles are described in EP 1426364 A1 ("Imidazole-derivatives as factor Xa inhibitors", p 27-28).

The compounds according to general formula I can be prepared using conventional synthetic methods for example but not limited to, the route outlined in Scheme 1. The amine 2 is coupled to an acid 1 to give the compound 3. This coupling is typically carried out using standard coupling conditions such as hydroxybenzotriazole and a carbodiimide, such as water soluble carbodiimide, in the presence of an organic base. Other standard coupling methods include the reaction of acids with amines in the presence of 2-(1H-benzotriazole-1-yl)-1,1,3,3-tetramethylaminium hexafluorophosphate, 2-(3H-[1,2,3]triazolo[4,5-b]pyridin-3-yl)-1,1,3,3-tetramethylisouronium hexafluorophosphate(V), benzotriazole-1-yl-oxy-tris-pyrrolidino-phosphoium hexafluorophosphate or bromo-trispyrolidino-phosphoium hexafluorophosphate in the presence of organic bases such as triethylamine, diisopropylethylamine or N-methylmorpholine. Alternatively the amide formation can take place via an acid chloride in the presence of an organic base. Such acid chlorides can be formed by methods well known in the literature, for example reaction of the acid with oxalyl chloride or thionyl chloride.

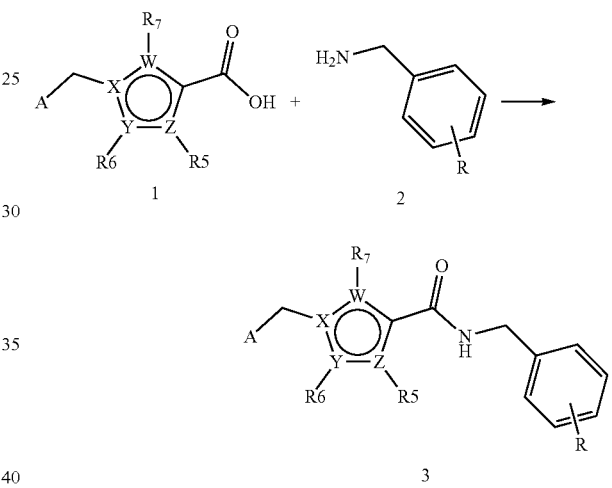

Scheme 1

Alternatively compounds according to general formula I can be prepared using the route outlined in Scheme 2a. The acid 4 can be coupled to an amine 2 using suitable coupling methods as previously described to give compound 5. In a typical second step the nitrogen of the heterocyclic ring is alkylated with compound 6 to give compound 7. The alkylation can be carried out in the presence of a base such as potassium carbonate, cesium carbonate, sodium carbonate or sodium hydride in which case the leaving group is a halide or sulphonate. Alternatively the alkylation may be carried out using an alcohol under Mitsunobu conditions in the presence of triphenylphosphine.

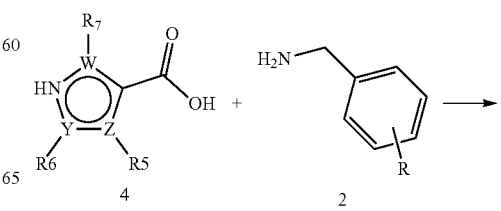

Scheme 2a

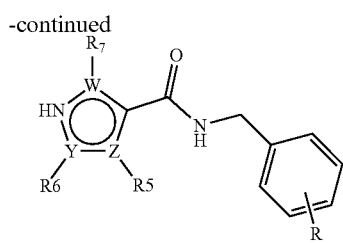

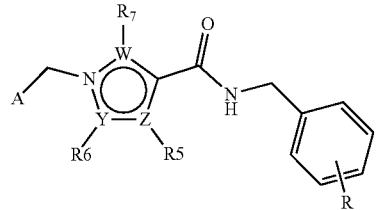

In a variation of Scheme 2a compounds according to general formula I can be prepared using the route outlined in Scheme 2b. Scheme 2b differs from Scheme 2a in that the moiety Y is equal to N therefore a protecting group strategy may be employed and the synthetic steps carried out in a different order. The pyrazole carboxylic acid, protected as an ester (PG) as described previously, compound 8, is alkylated with compound 6. The alkylation can be carried out in the presence of a base such as potassium carbonate, cesium carbonate, sodium carbonate or sodium hydride in which case the leaving group is a halide or sulphonate. Alternatively the alkylation may be carried out using an alcohol under Mitsunobu conditions in the presence of triphenylphosphine. In this case there are two possible nitrogens for the alkylation to occur at therefore there is the possibility of two regioisomers 9 and 10 being formed. Compounds 9 and 10 may be separated at this stage or at a subsequent stage in the synthesis using separation methods well known to those skilled in the art, for example by chromatography or by fractional crystallisation. The protecting group of compound 9 is removed by hydrolysis to give the corresponding acid 11 using standard methods as described previously. Compound 11 can be coupled to an amine 2 using suitable coupling methods as previously described to give compound 12.

Scheme 2b

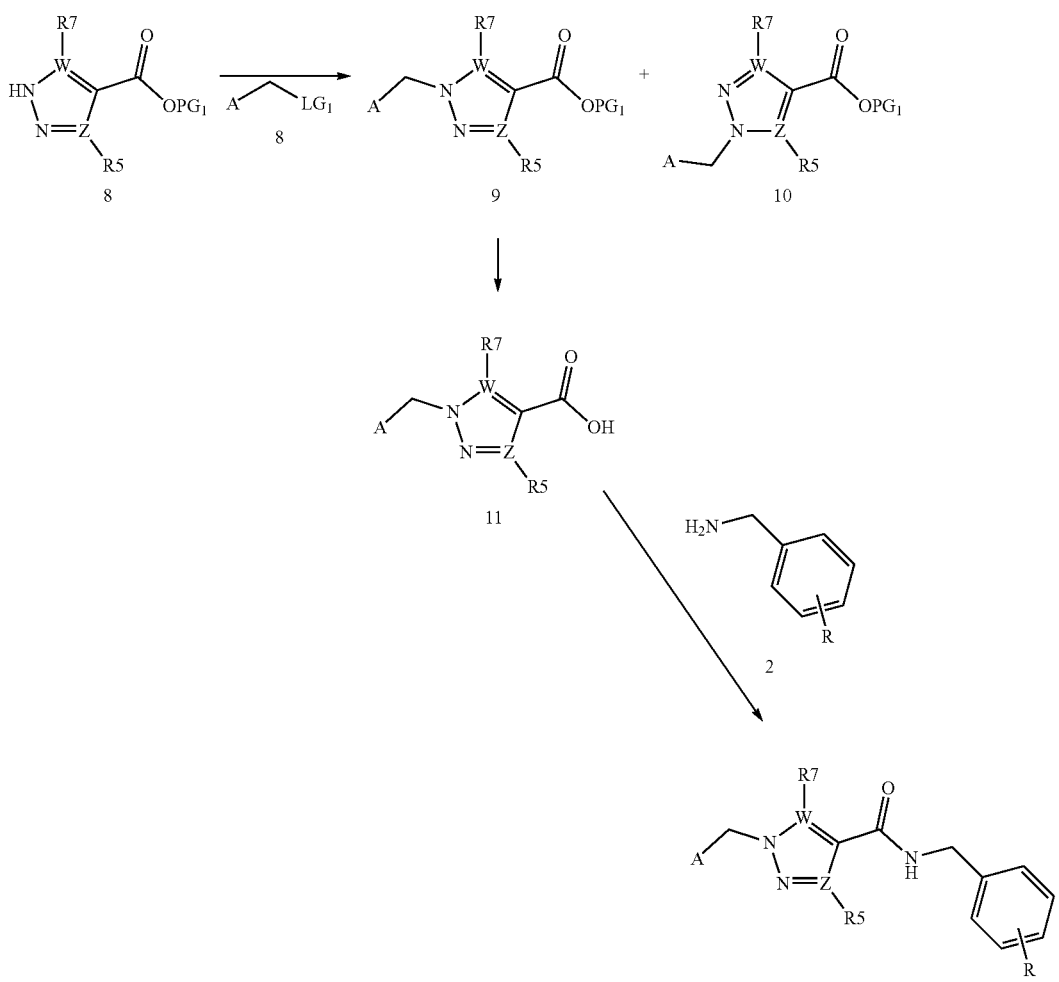

Alternatively compounds according to general formula I can be prepared using the route outlined in Scheme 3. The pyrrole 17 can be formed in two steps the first of which involves reaction of the sodium salt of an alkyl ketoacetate 13, typically protected with a protecting group (PG) as described previously, with a chloroketone 14 in the presence of a base such as potassium carbonate to give compound 15 which in a typical second step is reacted with the amine 16 in the presence of an acid such as but not limited to sulphonic acid derivatives e.g. p-toluenesulphonic acid to yield compound 17 which in a typical third step is subsequently hydrolysed to the corresponding acid 18 using standard methods as described previously. In a typical fourth step the acid 18 can be coupled to an amine 2 using suitable coupling methods as previously described to give compound 19.

The amine, compound 2 can be prepared using conventional synthetic methods for example, but not limited to, the routes outlined in Scheme 4. The nitrile of compound 20 is reduced by standard reducing agents including but not limited to lithium aluminium hydride, sodium borohydride, sodium borohydride and nickel chloride, sodium borohydride and cobalt chloride, borane, and catalytic hydrogenation over a catalyst such as palladium, platinum or Raney nickel. In some cases, for example when the reducing agent is sodium borohydride or catalytic hydrogenation is employed, it is possible to carry out in situ protection of the resulting amino group, for example resulting in the carbamate 21, for example tert-butoxy carbamate. This may be helpful to enable for example purification by chromatography of the intermediate compound 21. The protecting group is subsequently removed using standard conditions as described previously to give compound 2.

Scheme 3

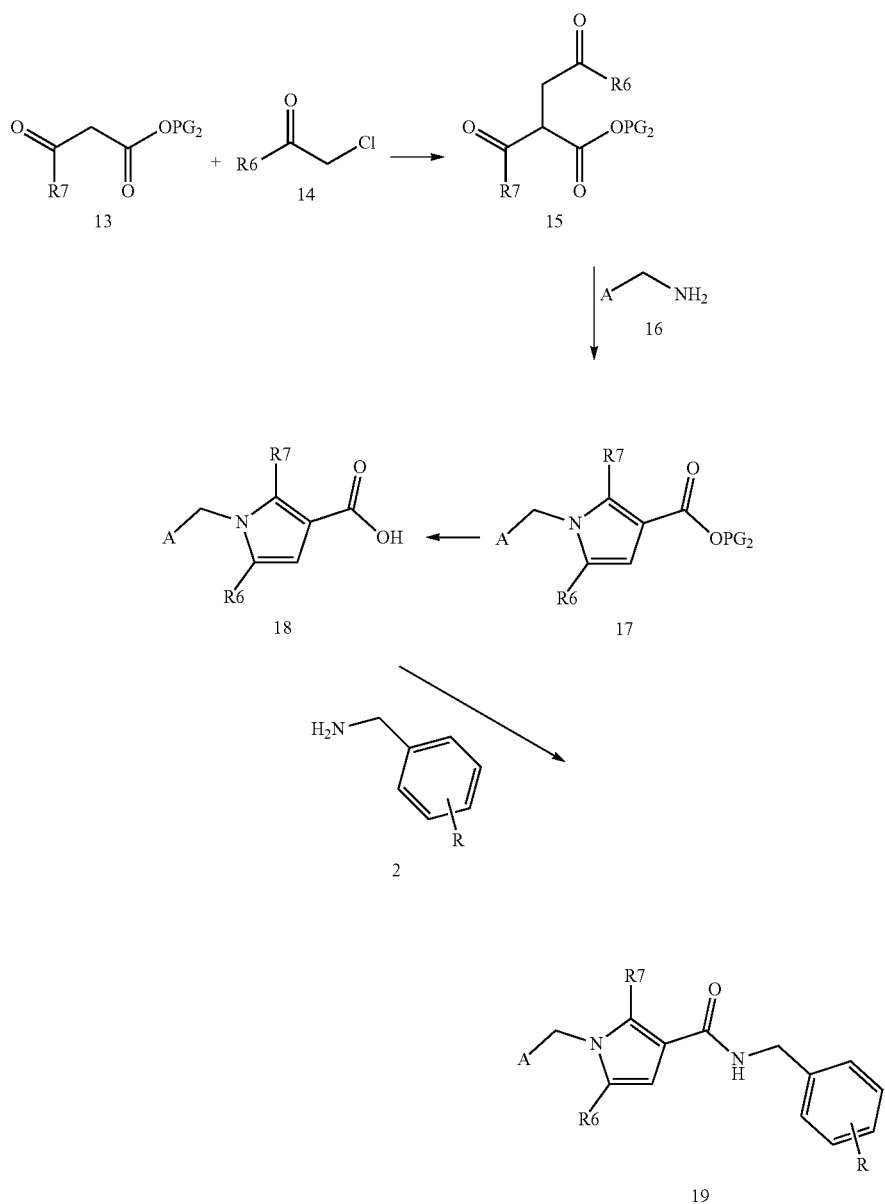

Scheme 4

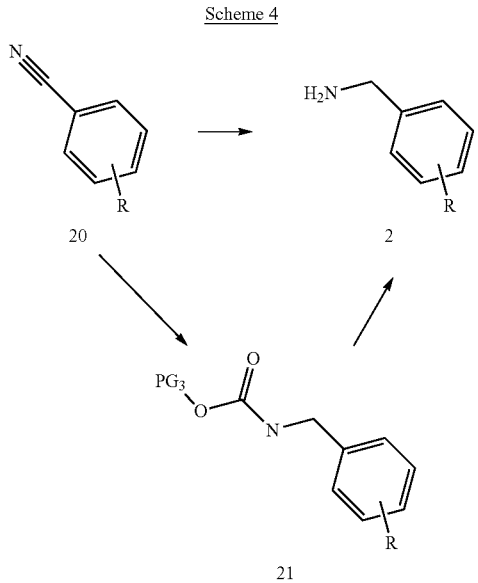

EXAMPLES

The invention is illustrated by the following non-limiting examples in which the following abbreviations and definitions are used:

| | |
|---|---|
| aq | Aqueous solution |
| DCM | Dichloromethane |
| DMF | N,N-Dimethylformamide |
| DMSO | Dimethyl sulfoxide |
| EtOAc | Ethyl Acetate |
| HATU | 2-(3H-[1,2,3]triazolo[4,5-b]pyridin-3-yl)-1,1,3,3-tetra-methylisouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| SWFI | Sterile water for injection |
| rt | room temperature |
| THF | Tetrahydrofuran |
| TFA | Trifluoroacetic acid |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% HCO$_2$H/MeCN into 0.1% HCO$_2$H/H$_2$O over 13 min, flow rate 1.5 mL/min, or using Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of Marvin-Sketch or as a component of the IDBS E-WorkBook.

A. 1-(4-Hydroxymethyl-benzyl)-1H-pyridin-2-one 4-(Chloromethyl)benzylalcohol (5.0 g, 31.93 mmol) was dissolved in acetone (150 mL). 2-hydroxypyridine (3.64 g, 38.3 mmol) and potassium carbonate (13.24 g, 95.78 mmol) were added and the reaction mixture was stirred at 50° C. for 3 hrs after which time the solvent was removed in vacuo and the residue taken up in chloroform (100 mL). This solution was washed with water (30 mL), brine (30 mL), dried (Na$_2$SO$_4$) and evaporated in vacuo. The residue was purified by flash chromatography (silica), eluent 3% MeOH/97% CHCl$_3$, to give a white solid identified as 1-(4-hydroxymethyl-benzyl)-1H-pyridin-2-one (5.30 g, 24.62 mmol, 77% yield).

[M+Na]$^+$=238

B1. 1-(4-Chloromethyl-benzyl)-1H-pyridin-2-one 1-(4-Hydroxymethyl-benzyl)-1H-pyridin-2-one (8.45 g, 39.3 mmol), dry DCM (80 mL) and triethylamine (7.66 ml, 55.0 mmol) were cooled in an ice bath. Methanesulfonyl chloride (3.95 ml, 51.0 mmol) was added and stirred in ice bath for 15 min. The ice bath was removed and stirring continued at rt temperature overnight. The reaction mixture was partitioned between DCM (100 mL) and saturated aqueous NH$_4$Cl solution (100 mL). The aqueous layer was extracted with further DCM (2×50 mL) and the combined organics washed with brine (50 mL), dried over Na$_2$SO$_4$, filtered and concentrated to give 1-(4-chloromethyl-benzyl)-1H-pyridin-2-one (8.65 g, 36.6 mmol, 93% yield) as a pale yellow solid.

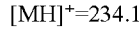
[MH]$^+$=234.1

B2. 1-(4-Bromomethyl-benzyl)-1H-pyridin-2-one 1-(4-Hydroxymethyl-benzyl)-1H-pyridin-2-one (2.30 g, 6.97 mmol) was dissolved in DCM (250 mL). To this solution was added phosphorous tribromide (5.78 g, 21.37 mmol). The reaction mixture was stirred at rt for 18 hrs and diluted with CHCl$_3$ (250 mL). The filtrate was washed with sat. NaHCO$_3$ (aq) (30 mL), water (30 mL), brine (30 mL), dried (Na$_2$SO$_4$) and evaporated in vacuo to give a white solid which was identified as 1-(4-bromomethyl-benzyl)-1H-pyridin-2-one (2.90 g, 10.43 mmol, 98%).

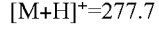
[M+H]$^+$=277.7

C. Methyl 3-(methoxymethyl)-1-(4-((2-oxopyridin-1 (2H)-yl)methyl)benzyl)-1H-pyrazole-4-carboxylate Potassium carbonate (519 mg, 3.76 mmol) was added to a solution of methyl 3-(methoxymethyl)-1H-pyrazole-4-carboxylate (320 mg, 1.88 mmol; CAS no. 318496-66-1 (synthesised according to the method described in WO 2012/009009)) and 1-(4-(chloromethyl)benzyl)pyridin-2(1H)-one (527 mg, 2.26 mmol) in DMF (5 mL) and heated at 60° C. overnight. The reaction mixture was diluted with EtOAc (50 mL) and washed with brine (2×100 mL), dried over magnesium sulfate, filtered and reduced in vacuo. The crude product was purified by flash chromatography (40 g column, 0-100% EtOAc in isohexanes) to afford two regioisomers. The second isomer off the column was collected to afford methyl 3-(methoxymethyl)-1-(4-((2-oxopyridin-1(2H)-yl)methyl)benzyl)-1H-pyrazole-4-carboxylate (378 mg, 1.01 mmol, 53.7% yield) as a colourless gum.

[MH]$^+$=368.2

D. 3-(Methoxymethyl)-1-(4-((2-oxopyridin-1(2H)-yl)methyl)benzyl)-1H-pyrazole-4-carboxylic Acid To methyl 3-(methoxymethyl)-1-(4-((2-oxopyridin-1(2H)-yl)methyl)benzyl)-1H-pyrazole-4-carboxylate (3.77 g, 10.26 mmol) in THF (5 mL) and MeOH (5 mL) was added 2M NaOH solution (15.39 ml, 30.8 mmol) and stirred at rt overnight. 1M HCl (50 mL) was added and extracted with EtOAc (50 mL). The organic layer was washed with brine (50 mL), dried over magnesium sulfate, filtered and reduced in vacuo to give 3-(methoxymethyl)-1-(4-((2-oxopyridin-1(2H)-yl)methyl)benzyl)-1H-pyrazole-4-carboxylic acid (1.22 g, 3.45 mmol, 33.6% yield) as a white powder.

[MH]$^+$=354.2

G. [4-(4-Methyl-pyrazol-1-ylmethyl)-phenyl]-methanol 4-(Chloromethyl)benzylalcohol (5.47 g, 34.9 mmol) was dissolved in acetone (50 mL). 4-Methylpyrazole (2.86 g, 34.9 mmol) and potassium carbonate (5.07 g, 36.7 mmol) were added and the reaction mixture was stirred at rt for 18 hrs and at 60° C. for 30 hrs after which time the solvent was removed in vacuo and the residue taken up in EtOAc (100 mL). This solution was washed with water (30 mL), brine (30 mL), dried (MgSO$_4$) and evaporated in vacuo. The residue was purified by flash chromatography (silica), eluent gradient of 10 to 80% EtOAc in iso-Hexane, fractions combined and evaporated in vacuo to give a white solid identified as [4-(4-methyl-pyrazol-1-ylmethyl)-phenyl]-methanol (3.94 g, 18.90 mmol, 54% yield).

[MH]$^+$=203

H. 1-(4-Chloromethyl-benzyl)-4-methyl-1H-pyrazole

[4-(4-Methyl-pyrazol-1-ylmethyl)-phenyl]-methanol (2.03 g, 10.04 mmol) and triethylamine (1.13 g, 11.54 mmol) was dissolved in DCM (40 mL). To this solution was added methanesulphonyl chloride (1.26 g, 11.04 mmol) dropwise. The reaction mixture was stirred at rt for 18 hrs and diluted with CHCl$_3$ (250 mL). The mixture was washed with saturated NH$_4$Cl (30 mL), water (30 mL), brine (30 mL), dried (Na$_2$SO$_4$) and evaporated in vacuo. The residue was purified by flash chromatography (silica), eluent gradient of 0 to 60% EtOAc in iso-Hexane, fractions combined and evaporated in vacuo to give a white solid identified as 1-(4-chloromethyl-benzyl)-4-methyl-1H-pyrazole (1.49 g, 6.62 mmol, 60% yield).

[MH]$^+$=221, 223

M. 3-Amino-1-[4-(2-oxo-2H-pyridin-1-ylmethyl)-benzyl]-1H-pyrazole-4-carboxylic Acid Ethyl Ester 1-(4-Bromomethyl-benzyl)-1H-pyridin-2-one (850 mg, 3.06 mmol) was dissolved in DMF (10 mL). 5-Amino-1H-pyrazole-4-carboxylic acid ethyl ester (522 mg, 3.36 mmol) and cesium carbonate (1.99 g, 6.11 mmol) were added and the reaction mixture was stirred at 50° C. for 18 hrs after which time the reaction mixture was diluted with EtOAc (100 mL). This solution was washed with water (30 mL), brine (30 mL), dried (Na$_2$SO$_4$) and evaporated in vacuo. The residue was purified by flash chromatography (silica), eluent gradient from 30% Pet Ether/70% EtOAc to 100% EtOAc, to afford two regioisomers. The second isomer off the column was collected to afford 3-amino-1-[4-(2-oxo-2H-pyridin-1-ylmethyl)-benzyl]-1H-pyrazole-4-carboxylic acid ethyl ester (480 mg, 1.36 mmol, 45% yield) as a white solid.

[MH]$^+$=353.1

N. 3-Amino-1-[4-(2-oxo-2H-pyridin-1-ylmethyl)-benzyl]-1H-pyrazole-4-carboxylic Acid 3-Amino-1-[4-(2-oxo-2H-pyridin-1-ylmethyl)-benzyl]-1H-pyrazole-4-carboxylic acid ethyl ester (480 mg, 1.36 mmol) was dissolved in THF (50 mL) and water (5 mL). Lithium hydroxide (16 3 mg, 6.81 mmol) was added. The reaction mixture was stirred at 50° C. for 18 hrs after which time the volatiles were removed in vacuo and the aqueous residue washed with CHCl$_3$ (150 mL). The aqueous layer was acidified with 1M HCl to pH7 and extracted with CHCl$_3$ (3×50 mL). The combined extracts were washed with water (30 mL), brine (30 mL), dried (Na$_2$SO$_4$) and evaporated in vacuo to give a white solid identified as 3-amino-1-[4-(2-oxo-2H-pyridin-1-ylmethyl)-benzyl]-1H-pyrazole-4-carboxylic acid (370 mg, 1.14 mmol, 84% yield).

[MH]$^+$=325.2

P. (2-Fluoro-3-methoxy-benzyl)-carbamic Acid Tert-Butyl Ester

2-Fluoro-3-methoxybenzonitrile (500 mg, 3.31 mmol) was dissolved in methanol (40 mL). This solution was cooled to 0° C. Nickel (II) chloride hexahydrate (79 mg, 0.33 mmol) and di-tertbutyl dicarbonate (1.44 g, 6.62 mmol) were added followed by sodium borohydride (876 mg, 23.16 mmol) portionwise. The reaction mixture was stirred, allowed to warm to rt and stirred for 3 days. The MeOH was removed in vacuo. The residue was dissolved in CHCl$_3$ (150 mL), washed with sat NaHCO$_3$ (aq) (50 mL), water (50 mL), brine (50 mL), dried (Na$_2$SO$_4$) and evaporated in vacuo. The residue was purified by chromatography (silica), eluent 20% EtOAc/80% Pet. Ether, to give a white solid identified as (2-fluoro-3-methoxy-benzyl)-carbamic acid tert-butyl ester (540 mg, 0.2 mmol, 64% yield).

[MH]$^+$=255.8

Q. 2-Fluoro-3-methoxy-benzylamine Hydrochloride (2-Fluoro-3-methoxy-benzyl)-carbamic acid tert-butyl ester (600 mg, 2.35 mmol) was dissolved in 4M HCl in dioxan (40 mL). After 2 hrs at rt the solvent was removed in vacuo to give a pale yellow solid identified as 2-fluoro-3-methoxy-benzylamine hydrochloride (414 mg, 2.17 mmol, 92% yield).

[MH]$^+$=155.9

T. 1-tert-Butyl 4-ethyl 3-aminopyrazole-1,4-dicarboxylate

To 5-amino-1H-pyrazole-4-carboxylic acid ethyl ester (250 mg, 1.61 mmol) in DCM (10 mL) was added di-tert-butyl dicarbonate (352 mg, 1.61 mmol) and diisopropylethylamine (702 μL, 521 mg, 4.03 mmol) and the reaction stirred at rt overnight. Reaction mixture was diluted with DCM, water added, separated, washed with brine, dried (MgSO$_4$), filtered and concentrated in vacuo. Flash chromatography afforded 1-tert-butyl 4-ethyl 3-aminopyrazole-1,4-dicarboxylate as a white solid (122 mg, 30% yield).

[MH]$^+$=256.2

U. Ethyl 3-acetamido-1H-pyrazole-4-carboxylate

A mixture of 1-tert-butyl 4-ethyl 3-aminopyrazole-1,4-dicarboxylate and acetyl chloride was stirred at 0° C. then heated at reflux for 2 hrs. The excess acetyl chloride was removed in vacuo. Water was added and the resulting mixture stirred for 18 hrs at rt. The precipitate was collected by vaccum filtration and dried to afford ethyl 3-acetamido-1H-pyrazole-4-carboxylate as a white solid (46 mg). The aqueous filtrate was extracted with DCM (4×15 mL) and the combined organic layers were dried (MgSO$_4$), filtered and concentrated in vacuo to afford a further crop of ethyl 3-acetamido-1H-pyrazole-4-carboxylate (48 mg) (overall yield 94 mg, 99%).

[MH]$^+$=197.8

V. 5-Dimethylamino-1H-pyrazole-4-carboxylic Acid Ester

5-Amino-1H-pyrazole-4-carboxylic acid ester (1.0 g, 6.45 mmol) was dissolved in methanol (200 mL) and the solution purged with nitrogen. Formaldehyde (37% by weight, 4.5 mL, 21.18 mmol) was added followed by 10% Pd/C (1.0 g). The reaction mixture was shaked on a Parr hydrogenator at 10 psi for 18 hrs. The reaction mixture was filtered through celite to remove the catalyst and the residue washed with methanol (200 mL) and water (20 mL). The combined filtrates were evaporated in vacuo. The crude residue was triturated with methanol/diethyl ether and the filtrate concentrated to afford a colourless oil identified as the title compound (1.1 g, 6.00 mmol, 93% yield).

[MH]$^+$=183.7

Example 1

N-(3,5-Dimethoxybenzyl)-3-(methoxymethyl)-1-(4-((2-oxopyridin-1(2H)-yl)methyl)benzyl)-1H-pyrazole-4-carboxamide

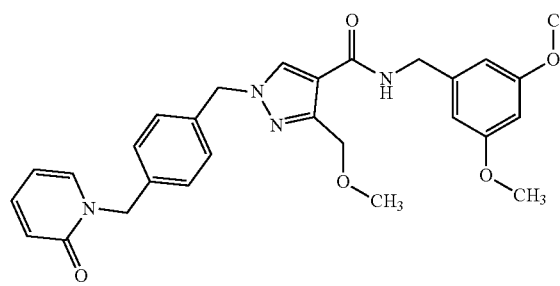

To a mixture of 3-(methoxymethyl)-1-(4-((2-oxopyridin-1(2H)-yl)methyl)benzyl)-1H-pyrazole-4-carboxylic acid (80 mg, 0.226 mmol), (3,5-dimethoxyphenyl)methanamine (45.4 mg, 0.272 mmol) and HATU (95 mg, 0.249 mmol) in anhydrous DCM (1.5 mL) and anhydrous DMF (0.3 mL) was added N,N-diisopropylethylamine (99 μl, 0.566 mmol) and the mixture allowed to stir at rt overnight. The reaction was concentrated in vacuo and the residue purified by flash chromatography loading in DCM, eluting with a gradient of 1 to 10% MeOH (containing 0.3% NH$_3$)/DCM to afford a gum. This was dissolved in acetonitrile (0.5 mL) and water (3 mL) added, forming a precipitate. This was sonicated, then filtered and dried under vacuum to afford N-(3,5-dimethoxybenzyl)-3-(methoxymethyl)-1-(4-((2-oxopyridin-1(2H)-yl)methyl)benzyl)-1H-pyrazole-4-carboxamide (76 mg, 0.150 mmol, 66.1% yield) as a sticky pale yellow solid.

NMR (d6-DMSO) δ: 3.20 (3H, s), 3.71 (6H, s), 4.32 (2H, d, J=5.8 Hz), 4.53 (2H, s), 5.07 (2H, s), 5.28 (2H, s), 6.22 (1H, td, J=6.7, 1.4 Hz), 6.37 (1H, t, J=2.3 Hz), 6.40 (1H, dd, J=9.2, 1.4 Hz), 6.44 (2H, d, J=2.3 Hz), 7.20-7.29 (4H, m), 7.41 (1H, ddd, J=9.1, 6.6, 2.1 Hz), 7.76 (1H, dd, J=6.8, 2.1 Hz), 8.24 (1H, s), 8.32 (1H, t, J=5.9 Hz).

[MH]$^+$=503.3

Example 2

3-Amino-1-[4-(2-oxo-2H-pyridin-1-ylmethyl)-benzyl]-1H-pyrazole-4-carboxylic acid 2-fluoro-3-methoxy-benzylamide

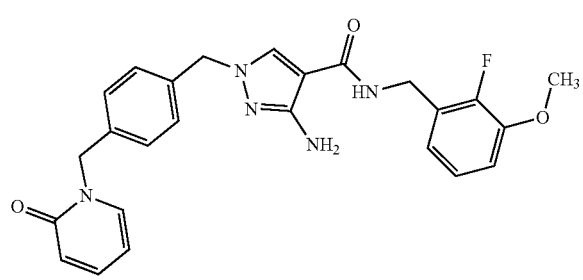 [SMILES: COc1cccc(CNC(=O)c2cn(Cc3ccc(Cn4ccccc4=O)cc3)nc2N)c1F]

3-Amino-1-[4-(2-oxo-2H-pyridin-1-ylmethyl)-benzyl]-1H-pyrazole-4-carboxylic acid (75 mg, 0.23 mmol) was dissolved in DCM (20 mL) and DMF (1 ml). This solution was cooled to 0° C. 2-Fluoro-3-methoxy-benzylamine hydrochloride (53 mg, 0.28 mmol) was added followed by HOBt (34 mg, 0.25 mmol) and triethylamine (70 mg, 0.69 mmol). Water soluble carbodiimide (53 mg, 0.28 mmol) was then added. The reaction mixture was stirred, allowed to warm to rt and stirred for 3 days. The mixture was diluted with chloroform (200 mL) and washed with NaHCO$_3$ (aq) (50 mL), water (50 mL) and brine (50 mL), dried (Na$_2$SO$_4$) and evaporated in vacuo. The residue was purified by flash chromatography (silica), eluent 4% MeOH/96% CHCl$_3$, to give a white solid identified as 3-amino-1-[4-(2-oxo-2H-pyridin-1-ylmethyl)-benzyl]-1H-pyrazole-4-carboxylic acid 2-fluoro-3-methoxy-benzylamide (92 mg, 0.20 mmol, 86% yield).

[MH]$^+$=462.2

$^1$H NMR: (d6-DMSO) δ: 3.82 (3H, s), 4.36 (2H, d, J=5.7 Hz), 5.04 (2H, s), 5.07 (2H, s), 5.38 (2H, s), 6.21-6.24 (1H, m), 6.39 (1H, t, J=0.7 Hz), 6.86-6.87 (1H, m), 7.04-7.07 (2H, m), 7.20 (2H, d, J=8.1 Hz), 7.26 (2H, d, J=8.1 Hz), 7.39-7.43 (1H, m), 7.76 (1H, dd, J=6.6, 1.6 Hz), 8.00 (1H, s), 8.27 (1H, t, J=5.9 Hz).

Example 3

1-(7-Chloro-quinolin-3-ylmethyl)-3-methoxymethyl-1H-pyrazole-4-carboxylic acid 2-fluoro-3-methoxy-benzylamide

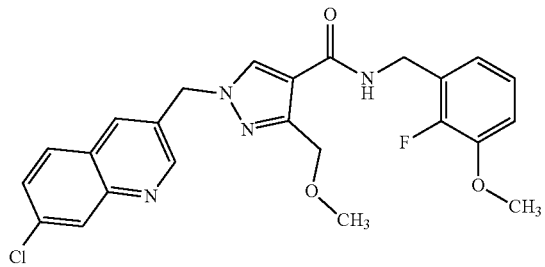 [SMILES: COCc1nn(Cc2cnc3cc(Cl)ccc3c2)cc1C(=O)NCc1cccc(OC)c1F]

(7-Chloro-quinolin-3-yl)-methanol

7-Chloroquinoline-3-carboxylic acid (500 mg, 2.4 mmol) was dissolved in anhydrous THF (20 mL) and cooled to −20° C. To this solution was added triethylamine (1.0 mL, 7.23 mmol) and isobutyl chloroformate (0.38 mL, 2.9 mmol). The reaction mixture was stirred at −20° C. for 20 min and then poured into a solution of sodium borohydride (731 mg, 19 mmol) in water (2 mL) at 0° C. The reaction mixture was allowed to warm to rt and stirred for 18 hours. The mixture was diluted with EtOAc (50 mL) and the layers separated. The organic layer was washed with water (20 mL), brine (20 mL), dried ($Na_2SO_4$), filtered and evaporated in vacuo to give a yellow solid. The solid was purified by chromatography on silica, eluting with EtOAc/Pet Ether to afford (7-chloro-quinolin-3-yl)-methanol as an off white solid, 134 mg, 29% yield.
$[MH]^+$=194.1

3-Bromomethyl-7-chloro-quinoline (7-Chloro-quinolin-3-yl)-methanol (134 mg, 0.692 mmol) was dissolved in DCM (5 mL). $PBr_3$ (65 µL, 0.692 mmol) was added and the reaction stirred for 3 hrs at rt. Upon completion, the reaction mixture was quenched with dilute $NaHCO_3$ (aq) (10 mL). The layers were separated and the organic washed with water (10 mL) and brine (10 mL). The organic layer was dried ($MgSO_4$), filtered and concentrated in vacuo to afford a yellow solid identified as 3-bromomethyl-7-chloro-quinoline (78 mg, 44% yield).
$[MH]^+$=257.6

1-(7-Chloro-quinolin-3-ylmethyl)-3-methoxymethyl-1H-pyrazole-4-carboxylic Acid Methyl Ester Methyl 3-(methoxymethyl)-1H-pyrazole-4-carboxylate (51 mg, 0.304 mmol; CAS no. 318496-66-1 (synthesised according to the method described in WO 2012/009009)) was taken up in DMF (2 mL) and treated with potassium carbonate (84 mg, 0.608 mmol) and 3-bromomethyl-7-chloro-quinoline (78 mg, 0.304 mmol). The reaction was stirred overnight at rt. EtOAc (60 mL) and water (20 mL) were added and the layers separated. The organic layer was washed with water (3×10 mL), brine (10 mL), dried ($MgSO_4$), filtered and evaporated in vacuo. The residue was purified by chromatography, eluting with EtOAc/Pet.Ether to afford two isomeric products. The faster running product was identified as the undesired regioisomer. The slower running product afforded a yellow oil and was identified as 1-(7-chloro-quinolin-3-ylmethyl)-3-methoxymethyl-1H-pyrazole-4-carboxylic acid methyl ester (53 mg, 50% yield).
$[MH]^+$=345.8

1-(7-Chloro-quinolin-3-ylmethyl)-3-methoxymethyl-1H-pyrazole-4-carboxylic Acid To 1-(7-chloro-quinolin-3-ylmethyl)-3-methoxymethyl-1H-pyrazole-4-carboxylic acid methyl ester (53 mg, 0.153 mmol) in ethanol (10 mL) was added sodium hydroxide (61 mg, 1.53 mmol) and the reaction was heated at vigorous reflux for 4.5 hrs. The mixture was cooled and concentrated in vacuo. The residue was diluted with water (5 mL), adjusted to pH 3.6 with 2M HCl and extracted with 90% chlorofrom/10% iso-propyl alcohol (6×15 mL). The combined organic layers were dried ($Na_2SO_4$), filtered and concentrated in vacuo to give 1-(7-chloro-quinolin-3-ylmethyl)-3-methoxymethyl-1H-pyrazole-4-carboxylic acid as a pale yellow solid (50 mg, 98% yield).
$[MH]^+$=332

1-(7-Chloro-quinolin-3-ylmethyl)-3-methoxymethyl-1H-pyrazole-4-carboxylic acid 2-fluoro-3-methoxy-benzylamide 1-(7-Chloro-quinolin-3-ylmethyl)-3-methoxymethyl-1H-pyrazole-4-carboxylic acid (25 mg, 0.075 mmol) was taken up in DCM (5 mL) at 0° C. To the solution was added triethylamine (52 µL, 0.377 mmol), HOBt (12 mg, 0.09 mmol) and water soluble carbodiimide (20 mg, 0.106 mmol). After 15 min, 2-fluoro-3-methoxy-benzylamine hydrochloride (14 mg, 0.075 mmol) was added and the reaction allowed to warm to rt and stirred for over the weekend. The reaction was diluted with $CHCl_3$ (50 ml) and washed with sat. aq. $NaHCO_3$ (20 ml) followed by water (20 mL) and brine (20 mL). The organic layer was dried ($MgSO_4$), filtered and concentrated in vacuo. The crude product was purified by chromatography eluting with 6% Methanol/94% DCM to give a white solid (16 mg, 45% yield) identified as 1-(7-chloro-quinolin-3-ylmethyl)-3-methoxymethyl-1H-pyrazole-4-carboxylic acid 2-fluoro-3-methoxy-benzylamide.
$[MH]^+$=469
1H NMR (DMSO): 3.20 (3H, s), 3.82 (3H, s), 4.41 (2H, d, J=5.8 Hz), 4.54 (2H, s), 5.57 (2H, s), 6.87-6.91 (1H, m), 7.03-7.09 (2H, m), 7.67 (1H, dd, J=8.8, 2.1 Hz), 8.07 (1H, d, J=8.8 Hz), 8.10 (1H, d, J=1.9 Hz), 8.30 (1H, d, J=1.7 Hz), 8.37 (1H, s), 8.39 (1H, t, J=5.8 Hz), 8.92 (1H, d, J=2.2 Hz)

Example 41

3-Fluoro-4-methoxy-pyridine-2-carbonitrile

To a large microwave vial, cyanocopper (1.304 g, 14.56 mmol) was added to a solution of 2-bromo-3-fluoro-4-methoxypyridine (1 g, 4.85 mmol) in DMF (5 mL). The reaction vial was sealed and heated to 100° C. for 16 hrs. The reaction mixture was diluted with water (20 mL) and EtOAc (20 mL). The thick suspension was sonicated and required additional water (40 mL) and EtOAc (2×50 mL) with sonication to break-up the solid precipitated. The combined layers were filtered through a plug of celite and the organic layer isolated, washed with brine (50 mL), dried over magnesium sulfate, filtered and the solvent removed under reduced pressure to give a pale green solid identified as the desired compound 3-fluoro-4-methoxy-pyridine-2-carbonitrile (100 mg, 0.578 mmol, 12% yield)

(3-Fluoro-4-methoxy-pyridin-2-ylmethyl)-carbamic Acid Tert-Butyl Ester

3-Fluoro-4-methoxy-pyridine-2-carbonitrile (100 mg, 0.578 mmol) was dissolved in anhydrous methanol (10 mL, 247 mmol) and nickel chloride hexahydrate (14 mg, 0.058 mmol) was added followed by di-tert-butyl dicarbonate (255 mg, 1.157 mmol). The resulting pale green solution was cooled in an ice-salt bath to −5° C. and then sodium borohydride (153 mg, 4.05 mmol) was added portionwise maintaining the reaction temperature 0° C. The deep brown solution was left to stir at 0° C. and slowly allowed to warm to rt and then left to stir at rt for 3 hrs. The reaction mixture was evaporated to dryness at 40° C. to afford a black residue which was diluted with DCM (10 mL) and washed with sodium hydrogen carbonate (10 mL). An emulsion formed so the organics were separated via a phase separating cartridge and concentrated. The crude liquid was purified by chromatography eluting with EtOAc/iso-Hexane to afford the title compound, (3-fluoro-4-methoxy-pyridin-2-ylmethyl)-carbamic acid tert-butyl ester as a clear yellow oil (108 mg, 62% yield)
$[MH]^+=257$

C-(3-Fluoro-4-methoxy-pyridin-2-yl)-methylamine Hydrochloride Salt (3-Fluoro-4-methoxy-pyridin-2-ylmethyl)-carbamic acid tert-butyl ester (108 mg, 0.358 mmol) was taken up in iso-propyl alcohol (1 mL) and then HCl (6N in iso-propyl alcohol) (1 mL, 0.578 mmol) was added at rt and left to stir at 40° C. for 2 hours. The reaction mixture was concentrated under reduced pressure and then triturated with ether, sonicated and then decanted to give a cream coloured solid (75 mg, 55% yield) identified as C-(3-fluoro-4-methoxy-pyridin-2-yl)-methylamine hydrochloride salt.
$[MH]^+=157$

3-Methoxymethyl-1-[4-(2-oxo-2H-pyridin-1-ylmethyl)-benzyl]-1H-pyrazole-4-carboxylic acid (3-fluoro-4-methoxy-pyridin-2-ylmethyl)-amide 3-(Methoxymethyl)-1-(4-((2-oxopyridin-1(2H)-yl)methyl)benzyl)-1H-pyrazole-4-carboxylic acid (75 mg, 0.212 mmol), C-(3-Fluoro-4-methoxy-pyridin-2-yl)-methylamine hydrochloride salt (49 mg, 0.212 mmol) and HATU (89 mg, 0.233 mmol) were suspended in anhydrous DCM (3 mL) to which triethylamine (177 µL, 1.270 mmol) was added, sonicated and then left to stir at rt for 4 hours. The solvent was removed under reduced pressure and the resulting residue was quenched with ammonium chloride solution (5 mL). An off white solid resulted which was sonicated, filtered under reduced pressure washed with water and then placed in the vac oven at 40° C. overnight. The crude material was purified by chromatography eluting with (1% ammonia-methanol)/DCM to afford the 3-methoxymethyl-1-[4-(2-oxo-2H-pyridin-1-ylmethyl)-benzyl]-1H-pyrazole-4-carboxylic acid (3-fluoro-4-methoxy-pyridin-2-ylmethyl)-amide as a white solid (67 mg, 64% yield)
$[MH]^+=492$
NMR (d$^6$-DMSO) δ: 3.25 (3H, s), 3.92 (3H, s), 4.46-4.57 (4H, m), 5.07 (2H, s), 5.28 (2H, s), 6.22 (1H, td, J=1.4, 6.7 Hz), 6.39 (1H, ddd, J=0.7, 1.4, 9.2 Hz), 7.17-7.28 (5H, m), 7.41 (1H, ddd, J=2.1, 6.6, 8.9 Hz), 7.75 (1H, ddd, J=0.7, 2.1, 6.8 Hz), 8.21-8.29 (2H, m), 8.42 (1H, t, J=5.4 Hz)

Example 77

6-Bromo-2-fluoro-3-methoxy-benzoic acid

To a suspension of 2-fluoro-3-methoxybenzoic acid (10 g, 58.8 mmol) in acetic acid (50 mL) and water (50 mL) at rt was added bromine (6.06 mL, 118 mmol) dropwise. The reaction was then heated to 60° C. for 1 hr. The reaction was cooled to room temperature and the white precipitate was filtered. The solid was washed with water (200 mL) and iso-Hexane (50 mL) to give 6-bromo-2-fluoro-3-methoxy-benzoic acid as white solid, 12.098 g, 82% yield.
$[MH]^+=249/251$

(6-Bromo-2-fluoro-3-methoxy-phenyl)-methanol

To a stirred solution of 6-bromo-2-fluoro-3-methoxy-benzoic acid (4.13 g, 16.58 mmol) in THF (20 mL) was added 4-methylmorpholine (1.914 mL, 17.41 mmol) and then isobutyl chloroformate (2.15 mL, 16.58 mmol). After 1 hour the reaction mixture was filtered to remove any salts generated, the solid was washed with additional THF (10 mL). The filtrate and washings were combined and cooled to 0° C. in an ice bath and then NaBH$_4$ (0.659 g, 17.41 mmol) in cold water (10 mL) was added in one portion (gas evolved), then allowed to warm to room temperature and stirred for 2 hours. The reaction mixture was quenched by careful addition of 1M HCl (30 mL) until acidic pH was obtained. The product was extracted into diethyl ether (150 mL). The organic layer was then washed with 2M NaOH (2×100 mL) to removed starting carboxylic acid, then acidified by washing with 1M HCl (100 mL), followed by brine (100 mL), dried over magnesium sulfate, filtered and solvent removed in vacuo. The crude product was purified by chromatography eluting with 0-50% EtOAc/iso-Hexane to afford (6-bromo-2-fluoro-3-methoxy-phenyl)-methanol as a colourless oil, 1.37 g, 50% yield.
$[MH]^+=217/219$

1-Bromo-2-chloromethyl-3-fluoro-4-methoxy-benzene

A solution of (6-bromo-2-fluoro-3-methoxy-phenyl)-methanol (500 mg, 2.127 mmol) in anhydrous DCM (4 mL) was treated with triethylamine (415 µL, 2.98 mmol), followed by methanesulfonyl chloride (214 µL, 2.77 mmol). The mixture was allowed to stir at ambient temperature overnight. The reaction mixture was partitioned between DCM (50 mL) and sat. aq. NH$_4$Cl (40 mL). The organic layer was collected and the aqueous layer extracted with further DCM (40 mL). The combined organics were washed with water (40 mL), brine (40 mL), dried (Na$_2$SO$_4$), filtered and concentrated. The crude material was purified by chromatography eluting with a gradient of 0 to 30% EtOAc/iso-Hexane to afford 1-bromo-2-chloromethyl-3-fluoro-4-methoxy-benzene (468 mg, 86% yield) as a white solid.

2-(6-Bromo-2-fluoro-3-methoxy-benzyl)-isoindole-1,3-dione

To a solution of 1-bromo-2-chloromethyl-3-fluoro-4-methoxy-benzene (460 mg, 1.815 mmol) in anhydrous DMF (5 mL) was added potassium phthalimide (403 mg, 2.178 mmol) and the mixture heated at 90° C. overnight. The mixture was diluted with EtOAc (75 mL) and washed with water (3×35 mL), brine (35 mL), dried (Na$_2$SO$_4$), filtered and concentrated to a yellow solid. The crude material was purified by flash chromatography, eluting with a gradient of 0 to 50% EtOAc/iso-Hexane. The desired product 2-(6-bromo-2-fluoro-3-methoxy-benzyl)-isoindole-1,3-dione was isolated as white needles, 372 mg, 56% yield.
[MH]$^+$=364.0/366.0

6-Bromo-2-fluoro-3-methoxy-benzylamine

A suspension of 2-(6-bromo-2-fluoro-3-methoxy-benzyl)-isoindole-1,3-dione (0.368 g, 1.011 mmol) in methanol (7.5 mL) was treated with hydrazine hydrate (0.064 mL, 1.314 mmol) and the reaction mixture heated at reflux for 5 hrs. The crude mixture was loaded directly onto an SCX column (8 g), washed with MeOH and eluted with 1% NH$_3$/MeOH to afford 6-bromo-2-fluoro-3-methoxy-benzylamine (204 mg, 85% yield) as a yellow oil
[MH]$^+$=233.9/235.9

3-Methoxymethyl-1-[4-(2-oxo-2H-pyridin-1-ylmethyl)-benzyl]-1H-pyrazole-4-carboxylic acid 6-bromo-2-fluoro-3-methoxy-benzylamide A 25 mL flask was charged with 3-(methoxymethyl)-1-(4-((2-oxopyridin-1(2H)-yl)methyl)benzyl)-1H-pyrazole-4-carboxylic acid (130 mg, 0.368 mmol), (6-bromo-2-fluoro-3-methoxy-benzylamine (86 mg, 0.368 mmol), HATU (154 mg, 0.405 mmol), anhydrous DCM (3 mL) and anhydrous DMF (0.5 mL). N,N-Disopropylethylamine (160 μL, 0.920 mmol) was added and the mixture allowed to stir at ambient temperature overnight. The reaction was concentrated under vacuum and redissolved in MeOH (4 mL) then purified by SCX, washing with MeOH, eluting with 1% NH$_3$/MeOH. The residue was further purified chromatography eluting with a gradient of 0 to 10% MeOH (containing 0.3% NH$_3$)/DCM to afford 3-methoxymethyl-1-[4-(2-oxo-2H-pyridin-1-ylmethyl)-benzyl]-1H-pyrazole-4-carboxylic acid 6-bromo-2-fluoro-3-methoxy-benzylamide (191 mg, 89% yield) as a white foam.
[MH]$^+$=569.2/571.2

3-Methoxymethyl-1-[4-(2-oxo-2H-pyridin-1-ylmethyl)-benzyl]-1H-pyrazole-4-carboxylic acid 6-cyano-2-fluoro-3-methoxy-benzylamide To a degassed solution of dicyanozinc (24.13 mg, 0.205 mmol) and 3-methoxymethyl-1-[4-(2-oxo-2H-pyridin-1-ylmethyl)-benzyl]-1H-pyrazole-4-carboxylic acid 6-bromo-2-fluoro-3-methoxy-benzylamide (90 mg, 0.158 mmol) in dimethylacetamide (1.2 mL) was added tetrakis(triphenylphosphine)palladium(0) (18.26 mg, 0.016 mmol) and the mixture heated to 110° C. overnight. The mixture was purified by chromatography eluting with a gradient of 0 to 10% (0.3% NH$_3$/MeOH)/DCM to give 3-methoxymethyl-1-[4-(2-oxo-2H-pyridin-1-ylmethyl)-benzyl]-1H-pyrazole-4-carboxylic acid 6-cyano-2-fluoro-3-methoxy-benzylamide as a pale yellow foam, 21 mg, 25% yield.
[MH]$^+$=516.3
$^1$H NMR (d$^6$-DMSO) δ: 3.21 (3H, s), 3.92 (3H, s), 4.47-4.55 (4H, m), 5.06 (2H, s), 5.27 (2H, s), 6.21 (1H, td, J=6.7, 1.4 Hz), 6.39 (1H, d, J=9.1 Hz), 7.17-7.31 (5H, m), 7.40 (1H, ddd, J=8.9, 6.6, 2.1 Hz), 7.67 (1H, dd, J=8.6, 1.5 Hz), 7.75 (1H, dd, J=6.8, 2.1 Hz), 8.20 (1H, s), 8.40 (1H, t, J=5.2 Hz)

Example 83

2-Chloro-3-fluoro-6-methoxy-benzaldehyde

To an ice-salt cooled flask containing methanol (8 mL, 198 mmol) was slowly added sodium hydride (1.318 g, 33.0 mmol). Once the addition was complete the cooling bath was removed and then allowed to warm to rt. In a second vessel (250 mL flask), 2-chloro-3,6-difluorobenzaldehyde (5 g, 27.5 mmol) was dissolved in a mixture of anhydrous methanol (60 mL, 1483 mmol) and THF (25 mL, 305 mmol) and warmed to 60° C. Whilst at 60° C. the sodium methoxide solution was slowly added to the reaction mixture. Once the addition was complete the reaction mixture was left to heat at 60° C. overnight. The solvent was removed under reduced pressure to give a bright yellow solid which was quenched with water (100 mL), sonicated and then left to stir for 30 min. The resulting yellow solid was filtered, washed with water and then left to dry under reduced pressure before transferring to a vacuum oven at 40° C. overnight. The crude was purified by chromatography eluting with EtOAc/iso-Hexane to afford the desired compound 2-chloro-3-fluoro-6-methoxy-benzaldehyde as an off white solid, 3.19 g, 61% yield.
[MH]$^+$=189/191

2-Chloro-3-difluoromethyl-1-fluoro-4-methoxy-benzene

2-Chloro-3-fluoro-6-methoxy-benzaldehyde (2 g, 10.61 mmol) was dissolved in anhydrous DCM (30 mL, 466 mmol) under a nitrogen filled balloon and cooled in a salt-ice bath. To the solution diethylaminosulfur trifluoride (4.20 mL, 31.8 mmol) was added dropwise to form a yellow solution. The reaction was stirred at 0° C. for 5 min and then the cooling bath was removed and the reaction allowed to warm to rt overnight. The reaction mixture was slowly quenched into saturated sodium hydrogen carbonate (100 mL), the organic layer was separated, washed with brine (100 mL) and dried using a phase separating cartridge. The solvent was removed under reduced pressure to give an orange oil, which was purified by chromatography eluting with EtOAc/iso-Hexane. 2-Chloro-3-difluoromethyl-1-fluoro-4-methoxy-benzene (1.0 g, 43% yield) was isolated as a pale yellow oil which solidified on standing.

2-Difluoromethyl-6-fluoro-3-methoxy-benzonitrile

2-Chloro-3-difluoromethyl-1-fluoro-4-methoxy-benzene (1 g, 4.75 mmol) was dissolved in anhydrous dimethylacetamide (7 mL, 74.7 mmol) to which dicyanozinc (0.558 g, 4.75 mmol) was added. Nitrogen was bubbled into the reaction mixture for 20 min then, tris(dibenzylideneacetone)dipalladium(0) (0.087 g, 0.095 mmol) and [1,1'bis(diphenylphosphino)ferrocene]dichloropalladium(II) complex with dichloromethane (0.139 g, 0.190 mmol) were added. The reaction mixture was heated at 150° C. overnight under an atmosphere of nitrogen. The reaction mixture was quenched into water (100 mL) and then extracted with EtOAc (3×200 mL). The combined organics were washed with brine (3×200 mL), dried over magnesium sulphate, filtered and evaporated under reduced pressure to give a dark brown oil. The crude product was purified by chromatography eluting with EtOAc/iso-Hexane to afford 2-difluoromethyl-6-fluoro-3-methoxy-benzonitrile (182 mg, 17% yield) as a brown solid.
[MH]$^+$=202.1

(2-Difluoromethyl-6-fluoro-3-methoxy-benzyl)-carbamic Acid Tert-Butyl Ester 2-(Difluoromethyl)-6-fluoro-3-methoxy-benzonitrile (182 mg, 0.778 mmol) was dissolved in anhydrous methanol (5 mL, 124 mmol) to which Nickel Chloride hexahydrate (19 mg, 0.078 mmol) was added followed by di-tert-butyl dicarbonate (343 mg, 1.556 mmol). The resulting pale green solution was cooled in an ice-salt bath to −5° C. and then sodium borohydride (206 mg, 5.45 mmol) was added portionwise, maintaining the reaction temperature 0° C. The deep brown solution was left to stir at 0° C. and slowly allowed to warm to rt overnight. The solvent was removed under reduced pressure and then partitioned between DCM (10 mL) and water (10 mL). The aqueous was re-extracted with DCM (2×10 mL). The combined organics were washed brine (10 mL), dried using a phase separating cartridge and concentrated in vacuo. The crude product was purified by chromatography eluting with EtOAc/iso-Hexane to give (2-difluoromethyl-6-fluoro-3-methoxy-benzyl)-carbamic acid tert-butyl ester as a white waxy solid (158 mg, 63% yield).

[MNa]$^+$=328

2-Difluoromethyl-6-fluoro-3-methoxy-benzylamine hydrochloride (2-Difluoromethyl-6-fluoro-3-methoxy-benzyl)-carbamic acid tert-butyl ester (158 mg, 0.492 mmol) was taken up in iso-propyl alcohol (1 mL) and then HCl (6N in iso-propyl alcohol) (1 mL, 0.778 mmol) was added and stirred at 40° C. for 1 hour. An off white precipitate formed and was collected via vacuum filtration and washed with iso-propyl alcohol (1 mL) to give the desired product 2-difluoromethyl-6-fluoro-3-methoxy-benzylamine hydrochloride as an off white solid (43 mg, 22% yield).

[MH]$^+$=206

3-Methoxymethyl-1-[4-(2-oxo-2H-pyridin-1-ylmethyl)-benzyl]-1H-pyrazole-4-carboxylic acid 2-difluoromethyl-6-fluoro-3-methoxy-benzylamide 3-(Methoxymethyl)-1-(4-((2-oxopyridin-1(2H)-yl) methyl)benzyl)-1H-pyrazole-4-carboxylic acid (58 mg, 0.162 mmol), 2-difluoromethyl-6-fluoro-3-methoxy-benzylamine hydrochloride salt (40.2 mg, 0.163 mmol) and HATU (68.3 mg, 0.180 mmol) were suspended in anhydrous DCM (3 mL) to which triethylamine (91 μL, 0.653 mmol) was added, sonicated and then left to stir at rt for 3 hrs. The solvent was removed under reduced pressure and the residue quenched with ammonium chloride solution (5 mL), resulting in a pale brown solid which was left to stir rt over the weekend. The solid was filtered under reduced pressure washed with water, dried under reduced pressure and then placed in the desiccator at 50° C. for 3 hours. The desired product, 3-, ethoxymethyl-1-[4-(2-oxo-2H-pyridin-1-ylmethyl)-benzyl]-1H-pyrazole-4-carboxylic acid 2-difluoromethyl-6-fluoro-3-methoxy-benzylamide (74 mg, 83% yield) was isolated as a free flowing cream solid.

[MH]$^+$=541.2

NMR (d$^6$-DMSO) δ 3.12 (3H, s), 3.83 (3H, s), 4.43 (2H, s), 4.52-4.59 (2H, m), 5.05 (2H, s), 5.25 (2H, s), 6.21 (1H, td, J=1.4, 6.7 Hz), 6.39 (1H, dt, J=1.0, 9.2 Hz), 7.15-7.44 (8H, m), 7.75 (1H, ddd, J=0.7, 2.1, 6.8 Hz), 8.08 (1H, t, J=4.9 Hz), 8.22 (1H, s)

Example 126

5-Bromomethyl-2-fluoro-pyridine

2-Fluoro-5-methylpyridine (5.0 g, 45 mmol) was dissolved in 1,2-dichloroethane (120 mL). To this solution was added N-bromosuccinimide (9.61 g, 54 mmol) and azobisisobutyronitrile (739 mg, 4.5 mmol). The reaction was stirred at reflux (95° C.) for 5 hours then the reaction was cooled to rt. The reaction mixture was diluted with CHCl$_3$ (50 mL) and was washed with sat. NaHCO$_3$ (1×20 mL), water (1×20 mL), followed by brine (1×20 mL), dried (Na$_2$SO$_4$) and filtered through PS paper and evaporated in vacuo. The residue was purified by chromatography (silica), eluting with 10% EtOAc, 90% Pet. Ether, to give a colourless oil identified as 5-bromomethyl-2-fluoro-pyridine, 5.9 g, 69% yield.

[MH]$^+$=191.76

NMR (CDCl3): 4.46 (2H, s), 6.93 (1H, dd, J=8.4, 3.0 Hz), 7.84 (1H, td, J=7.8, 2.6 Hz), 8.23 (1H, d, J=2.2 Hz)

1-(6-Fluoro-pyridin-3-ylmethyl)-3-trifluoromethyl-1H-pyrazole-4-carboxylic Acid Ethyl Ester Ethyl 3-trifluoromethyl-1H-pyrazole-4-carboxylate (1.57 g, 7.53 mmol) was dissolved in DMF (20 mL), 5-Bromomethyl-2-fluoro-pyridine (1.3 g, 6.84 mmol) and cesium carbonate (6.69 g, 20.53 mmol) were added. The reaction mixture was stirred at 50° C. for 18 hours after which time the reaction mixture was diluted with EtOAc (100 mL), this solution was washed with water (1×30 mL), brine (1×30 mL), dried (Na$_2$SO$_4$) and filtered through PS paper and evaporated in vacuo. The residue was purified by chromatography (silica), eluting with 85% Pet. Ether, 15% EtOAc to give a white foamy solid (1.26 g, 58% yield) identified as 1-(6-fluoro-pyridin-3-ylmethyl)-3-trifluoromethyl-1H-pyrazole-4-carboxylic acid ethyl ester.

[MMeCN]$^+$=358.75

1-(6-Fluoro-pyridin-3-ylmethyl)-3-trifluoromethyl-1H-pyrazole-4-carboxylic Acid 1-(6-Fluoro-pyridin-3-ylmethyl)-3-trifluoromethyl-1H-pyrazole-4-carboxylic acid ethyl ester (1.26 g, 3.97 mmol) was dissolved in THF (50 mL) and water (5 mL) then lithium hydroxide (476 mg, 19.86 mmol) were added. The reaction mixture was stirred at 50° C. for 18 hrs after which time the solvent was concentrated in vacuo and the residue taken up in EtOAc (50 mL). The aqueous layer was extracted and acidified with 1M HCl to pH2 and extracted with CHCl$_3$ (3×50 mL). The combined extracts were washed with water (1×30 mL) followed by brine (1×30 mL), dried (Na$_2$SO$_4$) and filtered through PS paper and evaporated in vacuo. The residue was purified by chromatography (silica), eluting with 3% MeOH, 97% CHCl$_3$, to give a colourless oil identified as 1-(6-fluoro-pyridin-3-ylmethyl)-3-trifluoromethyl-1H-pyrazole-4-carboxylic acid, 946 mg, 82% yield.

[MH]$^+$=289.82

1-(6-Pyrrolidin-1-yl-pyridin-3-ylmethyl)-3-trifluoromethyl-1H-pyrazole-4-carboxylic Acid 1-(6-Fluoro-pyridin-3-ylmethyl)-3-trifluoromethyl-1H-pyrazole-4-carboxylic acid (300 mg, 1.04 mmol) was dissolved in dioxane (25 mL) and pyrrolidine (2 mL) and the reaction mixture was stirred at 80° C. for 18 hrs. Upon completion the reaction mixture was diluted with EtOAc (100 mL), this solution was washed with water (1×30 mL), brine (1×30 mL), dried (Na$_2$SO$_4$) and filtered through PS paper and evaporated in vacuo. The residue was purified by chromatography eluting with 1% AcOH, 9% MeOH, 90% CHCl$_3$ to give a white foamy solid (267 mg, 76% yield) identified as 1-(6-pyrrolidin-1-yl-pyridin-3-ylmethyl)-3-trifluoromethyl-1H-pyrazole-4-carboxylic acid.

[MH]$^+$=340.72

1-(6-Pyrrolidin-1-yl-pyridin-3-ylmethyl)-3-trifluoromethyl-1H-pyrazole-4-carboxylic acid 2-fluoro-3-methoxy-benzylamide 2-Fluoro-3-methoxy-benzylamine hydrochloride (56 mg, 0.294 mmol) and 1-(6-pyrrolidin-1-yl-pyridin-3-ylmethyl)-3-trifluoromethyl-1H-pyrazole-4-carboxylic acid (100 mg, 0.294 mmol) were combined and taken up in DCM (10 mL) at 0° C. To the solution was added HOBt (48 mg, 0.353 mmol), triethylamine (205 μL, 1.469 mmol) and water soluble carbodiimide (79 mg, 0.411 mmol). The reaction was allowed to warm to rt and stirred for 3 days. The reaction was diluted with CHCl$_3$ (50 mL) and sat. aq. NaHCO$_3$ (20 mL) was added. The organic layer was separated, dried (MgSO$_4$), filtered and concentrated. The crude product was purified by chromatography eluting with MeOH/DCM to afford the desired product 1-(6-pyrrolidin-1-yl-pyridin-3-ylmethyl)-3-trifluoromethyl-1H-pyrazole-4-carboxylic acid 2-fluoro-3-methoxy-benzylamide as a white solid, 95 mg, 68% yield.

[MH]$^+$=478.0

$^1$H NMR (DMSO) δ: 1.90-1.94 (4H, m), 3.31-3.37 (4H, m), 3.82 (3H, s), 4.39 (2H, d, J=5.6 Hz), 5.26 (2H, s), 6.44 (1H, d, J=8.6 Hz), 6.85-6.90 (1H, m), 7.03-7.10 (2H, m), 7.50 (1H, dd, J=8.8, 2.4 Hz), 8.14 (1H, d, J=2.3 Hz), 8.36 (1H, d, J=0.6 Hz), 8.74 (1H, t, J=5.8 Hz)

TABLE 1

| Example number | R14 | R15 | R16 | R17 | R18 | Free Base MW | [M + H]$^+$ |
|---|---|---|---|---|---|---|---|
| 4  | F   | OMe | H   | H  | H    | 501.5 | 501.8 |
| 5  | H   | OMe | H   | H  | H    | 483.5 | 484.1 |
| 6  | H   | OEt | H   | H  | H    | 497.5 | 497.6 |
| 7  | H   | OCF$_3$ | H | H | H    | 537.5 | 537.8 |
| 8  | H   | H   | Me  | H  | H    | 467.5 | 468.1 |
| 9  | H   | OMe | H   | H  | F    | 501.5 | 501.9 |
| 10 | OMe | H   | OMe | H  | H    | 513.5 | 513.8 |
| 11 | F   | H   | OMe | H  | F    | 519.5 | 520.0 |
| 12 | CF$_3$ | H | OMe | H  | H    | 551.5 | 551.8 |
| 13 | F   | H   | H   | H  | F    | 489.4 | 490.0 |
| 14 | F   | H   | H   | H  | Cl   | 505.9 | 506.0 |
| 15 | F   | H   | H   | H  | CF$_3$ | 539.4 | 540.0 |
| 16 | F   | H   | Cl  | H  | F    | 523.9 | 523.9 |
| 17 | F   | H   | Cl  | H  | H    | 505.9 | 506.0 |
| 18 | F   | Cl  | H   | H  | F    | 523.9 | 523.9 |
| 19 | F   | Cl  | H   | H  | H    | 505.9 | 505.9 |
| 20 | F   | H   | H   | Cl | H    | 505.9 | 505.8 |
| 21 | F   | Cl  | H   | H  | CF$_3$ | 573.9 | 573.8 |
| 22 | Cl  | H   | H   | H  | Cl   | 522.4 | 593.9 |
| 23 | H   | H   | Cl  | H  | CF$_3$ | 555.9 | 555.8 |
| 24 | Me  | H   | Me  | H  | H    | 481.5 | 481.9 |
| 25 | Me  | H   | H   | H  | Me   | 481.5 | 481.9 |
| 26 | Me  | H   | Me  | H  | Me   | 495.5 | 496.1 |
| 27 | Me  | F   | H   | H  | H    | 485.5 | 485.9 |
| 28 | F   | H   | Me  | H  | H    | 485.5 | 486.1 |

TABLE 2

| Example number | R14 | R15 | Free Base MW | [M + H]$^+$ |
|---|---|---|---|---|
| 29 | F | H  | 472.4 | 472.9 |
| 30 | H | Cl | 488.9 | 488.9 |

TABLE 3
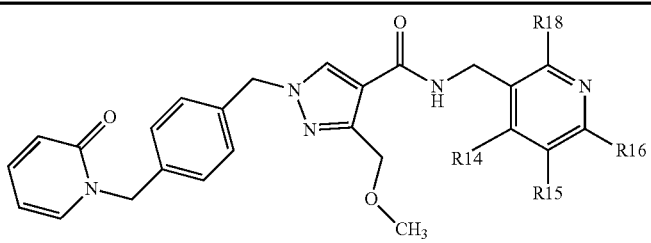
| Example number | R14 | R15 | R16 | R18 | Free Base MW | [M + H]+ |
|---|---|---|---|---|---|---|
| 31 | CF3 | H | H | H | 511.5 | 512.0 |
| 32 | H | H | Me | H | 457.5 | 458.3 |
| 33 | F | OMe | H | H | 491.5 | |
| 34 | NHCOMe | H | H | H | 500.5 | |
| 35 | F | H | H | CF3 | 529.5 | |
| 36 | H | H | H | CF3 | 511.5 | 512.3 |
| 37 | CF3 | H | H | H | 511.5 | 512.0 |
| 38 | F | H | H | H | 461.5 | |
| 39 | H | H | Me | H | 457.5 | 458.3 |
TABLE 4
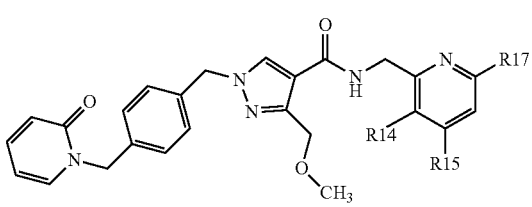
| Example number | R14 | R15 | R17 | Free Base MW | [M + H]+ |
|---|---|---|---|---|---|
| 40 | H | H | OMe | 473.5 | 474.0 |
| 41 | F | OMe | H | 491.5 | 492.0 |
| 42 | F | H | OMe | 491.5 | 492.3 |
TABLE 5
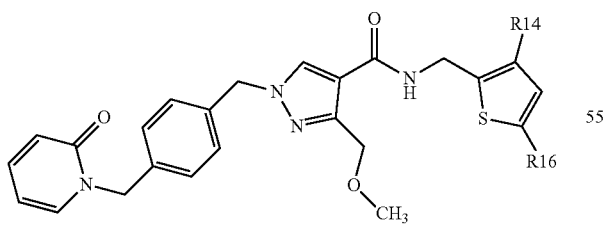
| Example number | R14 | R16 | Free Base MW |
|---|---|---|---|
| 43 | Cl | H | 483.0 |
| 44 | Cl | Me | 497.0 |
TABLE 6
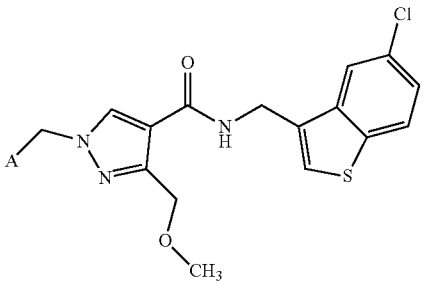
| Example number | A | Free Base MW | [M + H]+ |
|---|---|---|---|
| 45 | | 533.0 | 533.0 |
| 46 | | 496.0 | 495.9 |
| 47 | | 520.0 | 520.0 |
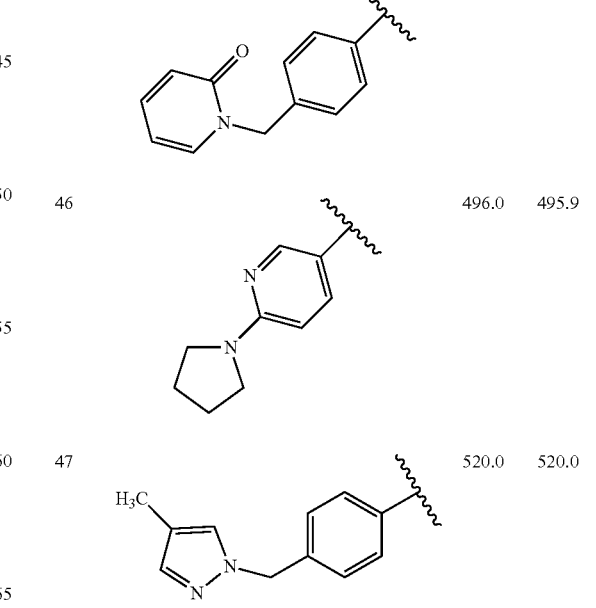

TABLE 7

| Example number | R5 | R14 | R15 | R16 | R17 | R18 | Free Base MW | [M + H]+ |
|---|---|---|---|---|---|---|---|---|
| 48 | 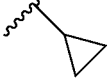 | CONH$_2$ | H | H | H | H | 481.5 | 482.0 |
| 49 |  | H | CONH$_2$ | H | H | H | 481.5 | 481.6 |
| 50 |  | H | H | CONH$_2$ | H | H | 481.5 | 481.7 |
| 51 | CF3 | F | H | H | H | CF3 | 552.4 | 552.9 |
| 52 | (cyclopropyl) | F | OMe | H | H | H | 486.5 | 486.8 |
| 53 | CH$_2$OMe | F | OMe | H | H | H | 490.5 | 491.0 |
| 54 | CH$_2$OMe | F | OMe | H | H | OMe | 520.6 | 521.2 |
| 55 | NHMe | F | OMe | H | H | H | 475.5 | |
| 56 | NHCH$_2$CH$_3$ | F | OMe | H | H | H | 489.5 | |
| 57 | NHCH(Me)$_2$ | F | OMe | H | H | H | 503.6 | |
| 58 | NH$_2$ | H | H | OCF$_3$ | H | H | 497.5 | 497.6 |
| 59 | NMe$_2$ | F | OMe | H | H | H | 489.5 | 490.2 |
| 60 | NH$_2$ | F | OMe | H | H | F | 479.5 | |
| 61 | NHMe | F | OMe | H | H | F | 493.5 | |
| 62 | CH$_2$OMe | F | H | H | H | H | 460.5 | 461.2 |
| 63 | CH$_2$OMe | CF$_3$ | H | H | H | H | 510.5 | 511.3 |
| 64 | CH$_2$OMe | F | H | H | OMe | H | 490.5 | 491.3 |
| 65 | CH$_2$OMe | F | H | Me | H | H | 474.5 | 475.3 |
| 66 | CH$_2$OMe | F | OMe | H | H | F | 508.5 | 509.0 |
| 67 | CH$_2$OMe | H | Cl | H | OMe | H | 507.0 | 507.0 |
| 68 | CH$_2$OMe | CHF$_2$ | H | H | H | H | 492.5 | 493.0 |
| 69 | CH$_2$OMe | CHF$_2$ | OMe | H | H | H | 522.5 | 523.0 |
| 70 | NH$_2$ | F | H | H | H | CF$_3$ | 499.5 | 500.0 |
| 71 | NHCOMe | F | OMe | H | H | H | 503.5 | 504.0 |
| 72 | NMeCOMe | F | OMe | H | H | H | 517.6 | 518.0 |
| 73 | CH$_2$OMe | F | Cl | H | H | F | 512.9 | 513.2 |
| 74 | CH$_2$OMe | F | OMe | Me | H | H | 504.6 | |
| 75 | CH$_2$OMe | CN | H | H | OMe | H | 497.5 | |
| 76 | CH$_2$OMe | CN | H | H | Cl | H | 502.0 | 502.2 |
| 77 | CH$_2$OMe | F | OMe | H | H | CN | 515.5 | 516.3 |
| 78 | CH$_2$OMe | CF$_3$ | OMe | H | H | H | 540.5 | 541.1 |
| 79 | CH$_2$OMe | CF$_3$ | H | H | OMe | H | 540.5 | 541.1 |
| 80 | CH$_2$OMe | CHF$_2$ | H | H | H | F | 510.5 | 511.2 |
| 81 | CH$_2$OMe | CHF$_2$ | H | H | OMe | H | 522.5 | 523.1 |
| 82 | CH$_2$OMe | CHF$_2$ | H | H | OMe | F | 540.5 | |
| 83 | CH$_2$OMe | CHF$_2$ | OMe | H | H | F | 540.5 | 541.2 |
| 84 | CH$_2$OMe | Cl | H | H | OMe | H | 507.0 | |
| 85 | CH$_2$OMe | CONH$_2$ | H | H | H | F | 503.5 | 504.3 |
| 86 | CH$_2$OMe | CONH$_2$ | H | H | OMe | H | 515.6 | 516.3 |
| 87 | CH$_2$OMe | COOH | H | H | H | H | 486.5 | 487.1 |

TABLE 7-continued

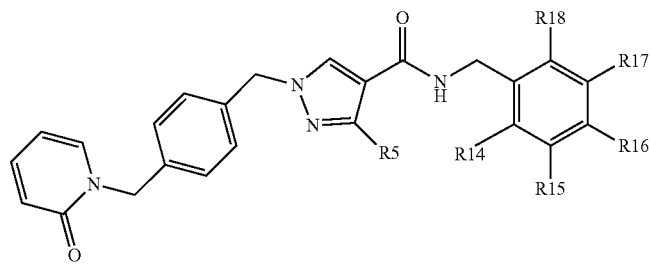

| Example number | R5 | R14 | R15 | R16 | R17 | R18 | Free Base MW | [M + H]+ |
|---|---|---|---|---|---|---|---|---|
| 88 | CH$_2$OMe | 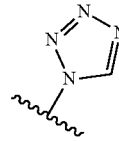 | H | H | H | F | 528.5 | |
| 89 | CH$_2$OMe | H | 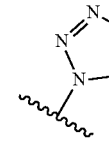 | H | H | F | 528.5 | |
| 90 | CH$_2$OMe | F | OCHF$_2$ | H | H | H | 526.5 | 527.2 |
| 91 | CH$_2$OMe | H | OCHF$_2$ | H | H | H | 508.5 | 509.2 |
| 92 | CH$_2$OMe | F | H | H | H | OCHF$_2$ | 526.5 | 527.3 |
| 93 | CH$_2$OMe | F | H | Me | H | CHF$_2$ | 524.5 | |
| 94 | CH$_2$OMe | F | H | H | F | H | 478.5 | 479.0 |
| 95 | CH$_2$OMe | H | OMe | H | F | H | 490.5 | 491.3 |
| 96 | CH$_2$OMe | F | OMe | H | F | H | 508.5 | 509.0 |
| 97 | CH$_2$OMe | F | H | H | H | Me | 474.5 | 475.0 |
| 98 | CH$_2$OMe | F | OMe | H | Cl | H | 525.0 | |
| 99 | CH$_2$OMe | F | OMe | H | H | Cl | 525.0 | 525.0 |
| 100 | CH$_2$OMe | F | OMe | H | H | CF3 | 558.5 | |
| 101 | CH$_2$OMe | F | H | Me | H | CF3 | 542.5 | |
| 102 | CH$_2$OMe | F | H | Cl | H | CF3 | 562.9 | |
| 103 | CN | F | OMe | H | H | H | 471.5 | |
| 129 | CH$_2$OMe | F | OH | H | H | H | 476.5 | 477.0 |
| 130 | NH$_2$ | F | OH | H | H | H | 447.5 | 447.9 |
| 131 | CH$_2$OMe | COOMe | H | H | H | H | 500.6 | 501.1 |
| 132 | CH$_2$OMe | F | CH$_2$Me | H | H | H | 488.6 | 489.3 |
| 133 | CH$_2$OMe | H | OMe | H | H | H | 472.5 | 473.1 |

TABLE 8

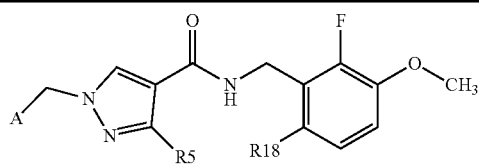

| Example number | A | R5 | R18 | Free Base MW | [M + H]+ |
|---|---|---|---|---|---|
| 104 | 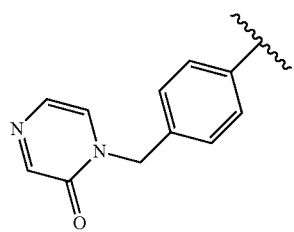 [SMILES: *c1ccc(Cn2ccncc2=O)cc1] | CH$_2$OMe | H | 491.5 | 492.0 |

TABLE 8-continued

| Example number | A | R5 | R18 | Free Base MW | [M + H]+ |
|---|---|---|---|---|---|
| 105 | 4-fluoro-2-oxo-1(2H)-pyridinyl-methyl-phenyl | CH₂OMe | F | 526.5 | |
| 106 | 4-methyl-2-oxo-1(2H)-pyridinyl-methyl-phenyl | CH₂OMe | F | 522.5 | 523.0 |
| 107 | 5-fluoro-2-oxo-1(2H)-pyridinyl-methyl-phenyl | CH₂OMe | H | 508.5 | |
| 108 | 5-fluoro-2-oxo-1(2H)-pyridinyl-methyl-phenyl | CH₂OMe | F | 526.5 | 527.0 |
| 109 | 4-ethoxy-2-oxo-1(2H)-pyridinyl-methyl-phenyl | CH₂OMe | F | 552.6 | 553.0 |
| 110 | 5-methoxy-4-methyl-pyrazolyl-methyl-phenyl | CH₂OMe | H | 507.6 | |

TABLE 8-continued

| Example number | A | R5 | R18 | Free Base MW | [M + H]+ |
|---|---|---|---|---|---|
| 111 | | CH2OMe | H | 482.5 | |
| 112 | | CH2OMe | H | 496.6 | |
| 113 | | NH2 | H | 448.5 | |
| 134 | | CH2OMe | CN | 502.5 | |
| 135 | | CH2OMe | CN | 479.5 | |
| 136 | | CF3 | CN | 503.5 | |
| 114 | | CH2OMe | H | 508.5 | |

TABLE 8-continued

Structure: pyrazole-4-carboxamide with N-CH2-A substituent, R5 at 3-position, linked via amide to benzyl group bearing R18, F, and OCH3 (2-F, 3-OMe pattern on phenyl).

| Example number | A | R5 | R18 | Free Base MW | [M + H]+ |
|---|---|---|---|---|---|
| 115 | 4-[(6-chloro-2-oxopyridin-1(2H)-yl)methyl]phenyl | CH2OMe | H | 525.0 | |
| 116 | 2-[(methylamino)methyl]phenyl | CH2OMe | F | 444.5 | |
| 117 | 2-[(methylamino)methyl]pyridin-4-yl | CH2OMe | H | 431.4 | |
| 118 | 2-(2,2,2-trifluoroethyl)phenyl | CH2OMe | H | 465.4 | |
| 119 | 2-(trifluoromethoxy)phenyl | CH2OMe | H | 467.4 | |

TABLE 9

Structure: imidazole-4-carboxamide with N1-substituted 4-[(2-oxopyridin-1(2H)-yl)methyl]benzyl, R5 at 2-position, amide linked to 2-fluoro-3-methoxybenzyl.

| Example number | R5 | Free Base MW | [M + H]+ |
|---|---|---|---|
| 121 | Me | 460.5 | 461.0 |
| 122 | NH2 | 461.5 | |
| 123 | cyclopropyl | 486.5 | |

TABLE 9-continued

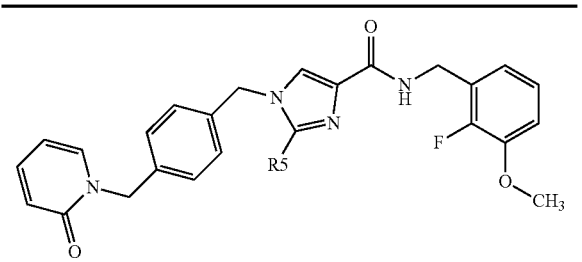

| Example number | R5 | Free Base MW | [M + H]+ |
|---|---|---|---|
| 124 | CF₃ | 514.5 | 515.0 |
| 125 | CH₂OMe | 490.5 | |

TABLE 10

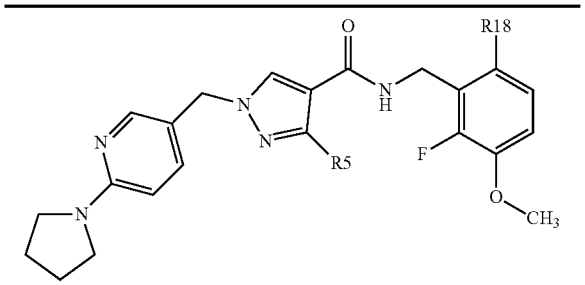

| Example number | R5 | R18 | Free Base MW | [M + H]+ |
|---|---|---|---|---|
| 126 | CF₃ | H | 477.5 | 478.0 |
| 127 | NH₂ | H | 424.5 | |
| 128 | CH₂OMe | H | 453.5 | |

TABLE 10-continued

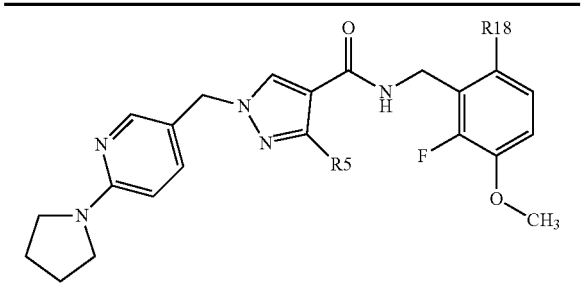

| Example number | R5 | R18 | Free Base MW | [M + H]+ |
|---|---|---|---|---|
| 137 | CH₂OMe | CN | 478.5 | |
| 138 | CF₃ | CN | 502.5 | |

TABLE 11

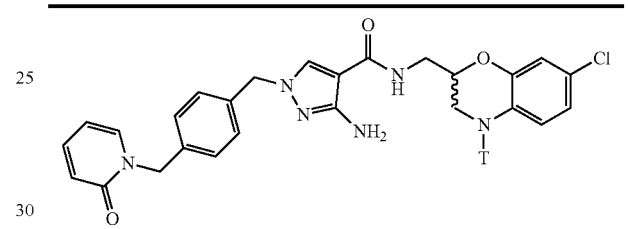

| Example number | T | Free Base MW | [M + H]+ |
|---|---|---|---|
| 139 | Me | 519.0 | 519.1 |
| 140 | H | 505.0 | 505.1 |

TABLE 12

Compound names

| Example Number | Name |
|---|---|
| 4 | N-[(2-fluoro-3-methoxyphenyl)methyl]-1-({4-[(4-methylpyrazol-1-yl)methyl]phenyl}methyl)-3-(trifluoromethyl)pyrazole-4-carboxamide |
| 5 | N-[(3-methoxyphenyl)methyl]-1-({4-[(4-methylpyrazol-1-yl)methyl]phenyl}methyl)-3-(trifluoromethyl)pyrazole-4-carboxamide |
| 6 | N-[(3-ethoxyphenyl)methyl]-1-({4-[(4-methylpyrazol-1-yl)methyl]phenyl}methyl)-3-(trifluoromethyl)pyrazole-4-carboxamide |
| 7 | 1-({4-[(4-methylpyrazol-1-yl)methyl]phenyl}methyl)-N-{[3-(trifluoromethoxy)phenyl]methyl}-3-(trifluoromethyl)pyrazole-4-carboxamide |
| 8 | N-[(4-methylphenyl)methyl]-1-({4-[(4-methylpyrazol-1-yl)methyl]phenyl}methyl)-3-(trifluoromethyl)pyrazole-4-carboxamide |
| 9 | N-[(2-fluoro-5-methoxyphenyl)methyl]-1-({4-[(4-methylpyrazol-1-yl)methyl]phenyl}methyl)-3-(trifluoromethyl)pyrazole-4-carboxamide |
| 10 | N-[(2,4-dimethoxyphenyl)methyl]-1-({4-[(4-methylpyrazol-1-yl)methyl]phenyl}methyl)-3-(trifluoromethyl)pyrazole-4-carboxamide |
| 11 | N-[(2,6-difluoro-4-methoxyphenyl)methyl]-1-({4-[(4-methylpyrazol-1-yl)methyl]phenyl}methyl)-3-(trifluoromethyl)pyrazole-4-carboxamide |
| 12 | N-{[4-methoxy-2-(trifluoromethyl)phenyl]methyl}-1-({4-[(4-methylpyrazol-1-yl)methyl]phenyl}methyl)-3-(trifluoromethyl)pyrazole-4-carboxamide |
| 13 | N-[(2,6-difluorophenyl)methyl]-1-({4-[(4-methylpyrazol-1-yl)methyl]phenyl}methyl)-3-(trifluoromethyl)pyrazole-4-carboxamide |
| 14 | N-[(2-chloro-6-fluorophenyl)methyl]-1-({4-[(4-methylpyrazol-1-yl)methyl]phenyl}methyl)-3-(trifluoromethyl)pyrazole-4-carboxamide |
| 15 | N-{[2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide |
| 16 | N-[(4-chloro-2,6-difluorophenyl)methyl]-1-({4-[(4-methylpyrazol-1-yl)methyl]phenyl}methyl)-3-(trifluoromethyl)pyrazole-4-carboxamide |
| 17 | N-[(4-chloro-2-fluorophenyl)methyl]-1-({4-[(4-methylpyrazol-1-yl)methyl]phenyl}methyl)-3-(trifluoromethyl)pyrazole-4-carboxamide |

TABLE 12-continued

Compound names

| Example Number | Name |
|---|---|
| 18 | N-[(3-chloro-2,6-difluorophenyl)methyl]-1-({4-[(4-methylpyrazol-1-yl)methyl]phenyl}methyl)-3-(trifluoromethyl)pyrazole-4-carboxamide |
| 19 | N-[(3-chloro-2-fluorophenyl)methyl]-1-({4-[(4-methylpyrazol-1-yl)methyl]phenyl}methyl)-3-(trifluoromethyl)pyrazole-4-carboxamide |
| 20 | N-[(5-chloro-2-fluorophenyl)methyl]-1-({4-[(4-methylpyrazol-1-yl)methyl]phenyl}methyl)-3-(trifluoromethyl)pyrazole-4-carboxamide |
| 21 | N-{[3-chloro-2-fluoro-6-(trifluoromethyl)phenyl]methyl}-1-({4-[(4-methylpyrazol-1-yl)methyl]phenyl}methyl)-3-(trifluoromethyl)pyrazole-4-carboxamide |
| 22 | N-[(2,6-dichlorophenyl)methyl]-1-({4-[(4-methylpyrazol-1-yl)methyl]phenyl}methyl)-3-(trifluoromethyl)pyrazole-4-carboxamide |
| 23 | N-{[5-chloro-2-(trifluoromethyl)phenyl]methyl}-1-({4-[(4-methylpyrazol-1-yl)methyl]phenyl}methyl)-3-(trifluoromethyl)pyrazole-4-carboxamide |
| 24 | N-[(2,4-dimethylphenyl)methyl]-1-({4-[(4-methylpyrazol-1-yl)methyl]phenyl}methyl)-3-(trifluoromethyl)pyrazole-4-carboxamide |
| 25 | N-[(2,6-dimethylphenyl)methyl]-1-({4-[(4-methylpyrazol-1-yl)methyl]phenyl}methyl)-3-(trifluoromethyl)pyrazole-4-carboxamide |
| 26 | 1-({4-[(4-methylpyrazol-1-yl)methyl]phenyl}methyl)-3-(trifluoromethyl)-N-[(2,4,6-trimethylphenyl)methyl]pyrazole-4-carboxamide |
| 27 | N-[(3-fluoro-2-methylphenyl)methyl]-1-({4-[(4-methylpyrazol-1-yl)methyl]phenyl}methyl)-3-(trifluoromethyl)pyrazole-4-carboxamide |
| 28 | N-[(2-fluoro-4-methylphenyl)methyl]-1-({4-[(4-methylpyrazol-1-yl)methyl]phenyl}methyl)-3-(trifluoromethyl)pyrazole-4-carboxamide |
| 29 | N-[(3-fluoropyridin-2-yl)methyl]-1-({4-[(4-methylpyrazol-1-yl)methyl]phenyl}methyl)-3-(trifluoromethyl)pyrazole-4-carboxamide |
| 30 | N-[(4-chloropyridin-2-yl)methyl]-1-({4-[(4-methylpyrazol-1-yl)methyl]phenyl}methyl)-3-(trifluoromethyl)pyrazole-4-carboxamide |
| 31 | 3-(methoxymethyl)-1-({4-[(2-oxopyridin-1-yl)methyl]phenyl}methyl)-N-{[4-(trifluoromethyl)pyridin-3-yl]methyl}pyrazole-4-carboxamide |
| 32 | 3-(methoxymethyl)-N-[(6-methylpyridin-3-yl)methyl]-1-({4-[(2-oxopyridin-1-yl)methyl]phenyl}methyl)pyrazole-4-carboxamide |
| 33 | N-[(4-fluoro-5-methoxypyridin-3-yl)methyl]-3-(methoxymethyl)-1-({4-[(2-oxopyridin-1-yl)methyl]phenyl}methyl)pyrazole-4-carboxamide |
| 34 | N-[(4-acetamidopyridin-3-yl)methyl]-3-(methoxymethyl)-1-({4-[(2-oxopyridin-1-yl)methyl]phenyl}methyl)pyrazole-4-carboxamide |
| 35 | N-{[4-fluoro-2-(trifluoromethyl)pyridin-3-yl]methyl}-3-(methoxymethyl)-1-({4-[(2-oxopyridin-1-yl)methyl]phenyl}methyl)pyrazole-4-carboxamide |
| 36 | 3-(methoxymethyl)-1-({4-[(2-oxopyridin-1-yl)methyl]phenyl}methyl)-N-{[2-(trifluoromethyl)pyridin-3-yl]methyl}pyrazole-4-carboxamide |
| 37 | 3-(methoxymethyl)-1-({4-[(2-oxopyridin-1-yl)methyl]phenyl}methyl)-N-{[4-(trifluoromethyl)pyridin-3-yl]methyl}pyrazole-4-carboxamide |
| 38 | N-[(4-fluoropyridin-3-yl)methyl]-3-(methoxymethyl)-1-({4-[(2-oxopyridin-1-yl)methyl]phenyl}methyl)pyrazole-4-carboxamide |
| 39 | 3-(methoxymethyl)-N-[(6-methylpyridin-3-yl)methyl]-1-({4-[(2-oxopyridin-1-yl)methyl]phenyl}methyl)pyrazole-4-carboxamide |
| 40 | 3-(methoxymethyl)-N-[(6-methoxypyridin-2-yl)methyl]-1-({4-[(2-oxopyridin-1-yl)methyl]phenyl}methyl)pyrazole-4-carboxamide |
| 41 | N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide |
| 42 | N-[(3-fluoro-6-methoxypyridin-2-yl)methyl]-3-(methoxymethyl)-1-({4-[(2-oxopyridin-1-yl)methyl]phenyl}methyl)pyrazole-4-carboxamide |
| 43 | N-[(3-chlorothiophen-2-yl)methyl]-3-(methoxymethyl)-1-({4-[(2-oxopyridin-1-yl)methyl]phenyl}methyl)pyrazole-4-carboxamide |
| 44 | N-[(3-chloro-5-methylthiophen-2-yl)methyl]-3-(methoxymethyl)-1-({4-[(2-oxopyridin-1-yl)methyl]phenyl}methyl)pyrazole-4-carboxamide |
| 45 | N-[(5-chloro-1-benzothiophen-3-yl)methyl]-3-(methoxymethyl)-1-({4-[(2-oxopyridin-1-yl)methyl]phenyl}methyl)pyrazole-4-carboxamide |
| 46 | N-[(5-chloro-1-benzothiophen-3-yl)methyl]-3-(methoxymethyl)-1-{[6-(pyrrolidin-1-yl)pyridin-3-yl]methyl}pyrazole-4-carboxamide |
| 47 | N-[(5-chloro-1-benzothiophen-3-yl)methyl]-3-(methoxymethyl)-1-({4-[(4-methylpyrazol-1-yl)methyl]phenyl}methyl)pyrazole-4-carboxamide |
| 48 | N-[(2-carbamoylphenyl)methyl]-3-cyclopropyl-1-({4-[(2-oxopyridin-1-yl)methyl]phenyl}methyl)pyrazole-4-carboxamide |
| 49 | N-[(3-carbamoylphenyl)methyl]-3-cyclopropyl-1-({4-[(2-oxopyridin-1-yl)methyl]phenyl}methyl)pyrazole-4-carboxamide |
| 50 | N-[(4-carbamoylphenyl)methyl]-3-cyclopropyl-1-({4-[(2-oxopyridin-1-yl)methyl]phenyl}methyl)pyrazole-4-carboxamide |
| 51 | N-{[2-fluoro-6-(trifluoromethyl)phenyl]methyl}-1-({4-[(2-oxopyridin-1-yl)methyl]phenyl}methyl)-3-(trifluoromethyl)pyrazole-4-carboxamide |
| 52 | 3-cyclopropyl-N-[(2-fluoro-3-methoxyphenyl)methyl]-1-({4-[(2-oxopyridin-1-yl)methyl]phenyl}methyl)pyrazole-4-carboxamide |
| 53 | N-[(2-fluoro-3-methoxyphenyl)methyl]-3-(methoxymethyl)-1-({4-[(2-oxopyridin-1-yl)methyl]phenyl}methyl)pyrazole-4-carboxamide |
| 54 | N-[(2-fluoro-3,6-dimethoxyphenyl)methyl]-3-(methoxymethyl)-1-({4-[(2-oxopyridin-1-yl)methyl]phenyl}methyl)pyrazole-4-carboxamide |

TABLE 12-continued

Compound names

| Example Number | Name |
|---|---|
| 55 | N-[(2-fluoro-3-methoxyphenyl)methyl]-3-(methylamino)-1-({4-[(2-oxopyridin-1-yl)methyl]phenyl}methyl)pyrazole-4-carboxamide |
| 56 | 3-(ethylamino)-N-[(2-fluoro-3-methoxyphenyl)methyl]-1-({4-[(2-oxopyridin-1-yl)methyl]phenyl}methyl)pyrazole-4-carboxamide |
| 57 | N-[(2-fluoro-3-methoxyphenyl)methyl]-3-(isopropylamino)-1-({4-[(2-oxopyridin-1-yl)methyl]phenyl}methyl)pyrazole-4-carboxamide |
| 58 | 3-amino-1-({4-[(2-oxopyridin-1-yl)methyl]phenyl}methyl)-N-{4-(trifluoromethoxy)phenyl]methyl}pyrazole-4-carboxamide |
| 59 | 3-(dimethylamino)-N-[(2-fluoro-3-methoxyphenyl)methyl]-1-({4-[(2-oxopyridin-1-yl)methyl]phenyl}methyl)pyrazole-4-carboxamide |
| 60 | 3-amino-N-[(2,6-difluoro-3-methoxyphenyl)methyl]-1-({4-[(2-oxopyridin-1-yl)methyl]phenyl}methyl)pyrazole-4-carboxamide |
| 61 | N-[(2,6-difluoro-3-methoxyphenyl)methyl]-3-(methylamino)-1-({4-[(2-oxopyridin-1-yl)methyl]phenyl}methyl)pyrazole-4-carboxamide |
| 62 | N-[(2-fluorophenyl)methyl]-3-(methoxymethyl)-1-({4-[(2-oxopyridin-1-yl)methyl]phenyl}methyl)pyrazole-4-carboxamide |
| 63 | 3-(methoxymethyl)-1-({4-[(2-oxopyridin-1-yl)methyl]phenyl}methyl)-N-{[2-(trifluoromethyl)phenyl]methyl}pyrazole-4-carboxamide |
| 64 | N-[(2-fluoro-5-methoxyphenyl)methyl]-3-(methoxymethyl)-1-({4-[(2-oxopyridin-1-yl)methyl]phenyl}methyl)pyrazole-4-carboxamide |
| 65 | N-[(2-fluoro-4-methylphenyl)methyl]-3-(methoxymethyl)-1-({4-[(2-oxopyridin-1-yl)methyl]phenyl}methyl)pyrazole-4-carboxamide |
| 66 | N-[(2,6-difluoro-3-methoxyphenyl)methyl]-3-(methoxymethyl)-1-({4-[(2-oxopyridin-1-yl)methyl]phenyl}methyl)pyrazole-4-carboxamide |
| 67 | N-[(3-chloro-5-methoxyphenyl)methyl]-3-(methoxymethyl)-1-({4-[(2-oxopyridin-1-yl)methyl]phenyl}methyl)pyrazole-4-carboxamide |
| 68 | N-{[2-(difluoromethyl)phenyl]methyl}-3-(methoxymethyl)-1-({4-[(2-oxopyridin-1-yl)methyl]phenyl}methyl)pyrazole-4-carboxamide |
| 69 | N-{[2-(difluoromethyl)-3-methoxyphenyl]methyl}-3-(methoxymethyl)-1-({4-[(2-oxopyridin-1-yl)methyl]phenyl}methyl)pyrazole-4-carboxamide |
| 70 | 3-amino-N-{[2-fluoro-6-(trifluoromethyl)phenyl]methyl}-1-({4-[(2-oxopyridin-1-yl)methyl]phenyl}methyl)pyrazole-4-carboxamide |
| 71 | 3-acetamido-N-[(2-fluoro-3-methoxyphenyl)methyl]-1-({4-[(2-oxopyridin-1-yl)methyl]phenyl}methyl)pyrazole-4-carboxamide |
| 72 | N-[(2-fluoro-3-methoxyphenyl)methyl]-3-(N-methylacetamido)-1-({4-[(2-oxopyridin-1-yl)methyl]phenyl}methyl)pyrazole-4-carboxamide |
| 73 | N-[(3-chloro-2,6-difluorophenyl)methyl]-3-(methoxymethyl)-1-({4-[(2-oxopyridin-1-yl)methyl]phenyl}methyl)pyrazole-4-carboxamide |
| 74 | N-[(2-fluoro-3-methoxy-4-methylphenyl)methyl]-3-(methoxymethyl)-1-({4-[(2-oxopyridin-1-yl)methyl]phenyl}methyl)pyrazole-4-carboxamide |
| 75 | N-[(2-cyano-5-methoxyphenyl)methyl]-3-(methoxymethyl)-1-({4-[(2-oxopyridin-1-yl)methyl]phenyl}methyl)pyrazole-4-carboxamide |
| 76 | N-[(5-chloro-2-cyanophenyl)methyl]-3-(methoxymethyl)-1-({4-[(2-oxopyridin-1-yl)methyl]phenyl}methyl)pyrazole-4-carboxamide |
| 77 | N-[(6-cyano-2-fluoro-3-methoxyphenyl)methyl]-3-(methoxymethyl)-1-({4-[(2-oxopyridin-1-yl)methyl]phenyl}methyl)pyrazole-4-carboxamide |
| 78 | N-{[3-methoxy-2-(trifluoromethyl)phenyl]methyl}-3-(methoxymethyl)-1-({4-[(2-oxopyridin-1-yl)methyl]phenyl}methyl)pyrazole-4-carboxamide |
| 79 | N-{[5-methoxy-2-(trifluoromethyl)phenyl]methyl}-3-(methoxymethyl)-1-({4-[(2-oxopyridin-1-yl)methyl]phenyl}methyl)pyrazole-4-carboxamide |
| 80 | N-{[2-(difluoromethyl)-6-fluorophenyl]methyl}-3-(methoxymethyl)-1-({4-[(2-oxopyridin-1-yl)methyl]phenyl}methyl)pyrazole-4-carboxamide |
| 81 | N-{[2-(difluoromethyl)-5-methoxyphenyl]methyl}-3-(methoxymethyl)-1-({4-[(2-oxopyridin-1-yl)methyl]phenyl}methyl)pyrazole-4-carboxamide |
| 82 | N-{[6-(difluoromethyl)-2-fluoro-3-methoxyphenyl]methyl}-3-(methoxymethyl)-1-({4-[(2-oxopyridin-1-yl)methyl]phenyl}methyl)pyrazole-4-carboxamide |
| 83 | N-{[2-(difluoromethyl)-6-fluoro-3-methoxyphenyl]methyl}-3-(methoxymethyl)-1-({4-[(2-oxopyridin-1-yl)methyl]phenyl}methyl)pyrazole-4-carboxamide |
| 84 | N-[(2-chloro-5-methoxyphenyl)methyl]-3-(methoxymethyl)-1-({4-[(2-oxopyridin-1-yl)methyl]phenyl}methyl)pyrazole-4-carboxamide |
| 85 | N-[(2-carbamoyl-6-fluorophenyl)methyl]-3-(methoxymethyl)-1-({4-[(2-oxopyridin-1-yl)methyl]phenyl}methyl)pyrazole-4-carboxamide |
| 86 | N-[(2-carbamoyl-5-methoxyphenyl)methyl]-3-(methoxymethyl)-1-({4-[(2-oxopyridin-1-yl)methyl]phenyl}methyl)pyrazole-4-carboxamide |
| 87 | 2-({[3-(methoxymethyl)-1-({4-[(2-oxopyridin-1-yl)methyl]phenyl}methyl)pyrazol-4-yl]formamido}methyl)benzoic acid |
| 88 | N-{[2-fluoro-6-(1,2,3,4-tetrazol-1-yl)phenyl]methyl}-3-(methoxymethyl)-1-({4-[(2-oxopyridin-1-yl)methyl]phenyl}methyl)pyrazole-4-carboxamide |
| 89 | N-{[2-fluoro-5-(1,2,3,4-tetrazol-1-yl)phenyl]methyl}-3-(methoxymethyl)-1-({4-[(2-oxopyridin-1-yl)methyl]phenyl}methyl)pyrazole-4-carboxamide |
| 90 | N-{[3-(difluoromethoxy)-2-fluorophenyl]methyl}-3-(methoxymethyl)-1-({4-[(2-oxopyridin-1-yl)methyl]phenyl}methyl)pyrazole-4-carboxamide |
| 91 | N-{[3-(difluoromethoxy)phenyl]methyl}-3-(methoxymethyl)-1-({4-[(2-oxopyridin-1-yl)methyl]phenyl}methyl)pyrazole-4-carboxamide |

TABLE 12-continued

Compound names

| Example Number | Name |
|---|---|
| 92 | N-{[2-(difluoromethoxy)-6-fluorophenyl]methyl}-3-(methoxymethyl)-1-({4-[(2-oxopyridin-1-yl)methyl]phenyl}methyl)pyrazole-4-carboxamide |
| 93 | N-{[2-(difluoromethyl)-6-fluoro-4-methylphenyl]methyl}-3-(methoxymethyl)-1-({4-[(2-oxopyridin-1-yl)methyl]phenyl}methyl)pyrazole-4-carboxamide |
| 94 | N-[(2,5-difluorophenyl)methyl]-3-(methoxymethyl)-1-({4-[(2-oxopyridin-1-yl)methyl]phenyl}methyl)pyrazole-4-carboxamide |
| 95 | N-[(3-fluoro-5-methoxyphenyl)methyl]-3-(methoxymethyl)-1-({4-[(2-oxopyridin-1-yl)methyl]phenyl}methyl)pyrazole-4-carboxamide |
| 96 | N-[(2,5-difluoro-3-methoxyphenyl)methyl]-3-(methoxymethyl)-1-({4-[(2-oxopyridin-1-yl)methyl]phenyl}methyl)pyrazole-4-carboxamide |
| 97 | N-[(2-fluoro-6-methylphenyl)methyl]-3-(methoxymethyl)-1-({4-[(2-oxopyridin-1-yl)methyl]phenyl}methyl)pyrazole-4-carboxamide |
| 98 | N-[(5-chloro-2-fluoro-3-methoxyphenyl)methyl]-3-(methoxymethyl)-1-({4-[(2-oxopyridin-1-yl)methyl]phenyl}methyl)pyrazole-4-carboxamide |
| 99 | N-[(6-chloro-2-fluoro-3-methoxyphenyl)methyl]-3-(methoxymethyl)-1-({4-[(2-oxopyridin-1-yl)methyl]phenyl}methyl)pyrazole-4-carboxamide |
| 100 | N-{[2-fluoro-3-methoxy-6-(trifluoromethyl)phenyl]methyl}-3-(methoxymethyl)-1-({4-[(2-oxopyridin-1-yl)methyl]phenyl}methyl)pyrazole-4-carboxamide |
| 101 | N-{[2-fluoro-4-methyl-6-(trifluoromethyl)phenyl]methyl}-3-(methoxymethyl)-1-({4-[(2-oxopyridin-1-yl)methyl]phenyl}methyl)pyrazole-4-carboxamide |
| 102 | N-{[4-chloro-2-fluoro-6-(trifluoromethyl)phenyl]methyl}-3-(methoxymethyl)-1-({4-[(2-oxopyridin-1-yl)methyl]phenyl}methyl)pyrazole-4-carboxamide |
| 103 | 3-cyano-N-[(2-fluoro-3-methoxyphenyl)methyl]-1-({4-[(2-oxopyridin-1-yl)methyl]phenyl}methyl)pyrazole-4-carboxamide |
| 129 | N-[(2-fluoro-3-hydroxyphenyl)methyl]-3-(methoxymethyl)-1-({4-[(2-oxopyridin-1-yl)methyl]phenyl}methyl)pyrazole-4-carboxamide |
| 130 | 3-amino-N-[(2-fluoro-3-hydroxyphenyl)methyl]-1-({4-[(2-oxopyridin-1-yl)methyl]phenyl}methyl)pyrazole-4-carboxamide |
| 131 | methyl 2-({[3-(methoxymethyl)-1-({4-[(2-oxopyridin-1-yl)methyl]phenyl}methyl)pyrazol-4-yl]formamido}methyl)benzoate |
| 132 | N-[(3-ethyl-2-fluorophenyl)methyl]-3-(methoxymethyl)-1-({4-[(2-oxopyridin-1-yl)methyl]phenyl}methyl)pyrazole-4-carboxamide |
| 133 | 3-(methoxymethyl)-N-[(3-methoxyphenyl)methyl]-1-({4-[(2-oxopyridin-1-yl)methyl]phenyl}methyl)pyrazole-4-carboxamide |
| 104 | N-[(2-fluoro-3-methoxyphenyl)methyl]-3-(methoxymethyl)-1-({4-[(2-oxopyrazin-1-yl)methyl]phenyl}methyl)pyrazole-4-carboxamide |
| 105 | N-[(2,6-difluoro-3-methoxyphenyl)methyl]-1-({4-[(4-fluoro-2-oxopyridin-1-yl)methyl]phenyl}methyl)-3-(methoxymethyl)pyrazole-4-carboxamide |
| 106 | N-[(2,6-difluoro-3-methoxyphenyl)methyl]-3-(methoxymethyl)-1-({4-[(4-methyl-2-oxopyridin-1-yl)methyl]phenyl}methyl)pyrazole-4-carboxamide |
| 107 | 1-({4-[(5-fluoro-2-oxopyridin-1-yl)methyl]phenyl}methyl)-N-[(2-fluoro-3-methoxyphenyl)methyl]-3-(methoxymethyl)pyrazole-4-carboxamide |
| 108 | N-[(2,6-difluoro-3-methoxyphenyl)methyl]-1-({4-[(5-fluoro-2-oxopyridin-1-yl)methyl]phenyl}methyl)-3-(methoxymethyl)pyrazole-4-carboxamide |
| 109 | N-[(2,6-difluoro-3-methoxyphenyl)methyl]-1-({4-[(4-ethoxy-2-oxopyridin-1-yl)methyl]phenyl}methyl)-3-(methoxymethyl)pyrazole-4-carboxamide |
| 110 | N-[(2-fluoro-3-methoxyphenyl)methyl]-1-({4-[(5-methoxy-4-methylpyrazol-1-yl)methyl]phenyl}methyl)-3-(methoxymethyl)pyrazole-4-carboxamide |
| 111 | N-[(2-fluoro-3-methoxyphenyl)methyl]-3-(methoxymethyl)-1-{[5-(2-oxopyridin-1-yl)thiophen-3-yl]methyl}pyrazole-4-carboxamide |
| 112 | N-[(2-fluoro-3-methoxyphenyl)methyl]-3-(methoxymethyl)-1-({5-[(2-oxopyridin-1-yl)methyl]thiophen-3-yl}methyl)pyrazole-4-carboxamide |
| 113 | 3-amino-N-[(2-fluoro-3-methoxyphenyl)methyl]-1-({4-[(4-methylpyrazol-1-yl)methyl]phenyl}methyl)pyrazole-4-carboxamide |
| 134 | 3-methoxymethyl-1-[4-(4-methyl-pyrazol-1-ylmethyl)-benzyl]-1H-pyrazole-4-carboxylic acid 6-cyano-2-fluoro-3-methoxy-benzylamide |
| 135 | 3-methoxymethyl-1-(2-pyrrolidin-1-yl-pyrimidin-5-ylmethyl)-1H-pyrazole-4-carboxylic acid 6-cyano-2-fluoro-3-methoxy-benzylamide |
| 136 | 1-(2-pyrrolidin-1-yl-pyrimidin-5-ylmethyl)-3-trifluoromethyl-1H-pyrazole-4-carboxylic acid 6-cyano-2-fluoro-3-methoxy-benzylamide |
| 114 | N-[(2-fluoro-3-methoxyphenyl)methyl]-1-({4-[(2-fluoro-6-oxopyridin-1-yl)methyl]phenyl}methyl)-3-(methoxymethyl)pyrazole-4-carboxamide |
| 115 | 1-({4-[(2-chloro-6-oxopyridin-1-yl)methyl]phenyl}methyl)-N-[(2-fluoro-3-methoxyphenyl)methyl]-3-(methoxymethyl)pyrazole-4-carboxamide |
| 116 | N-[(2,6-difluoro-3-methoxyphenyl)methyl]-3-(methoxymethyl)-1-({2-[(methylamino)methyl]phenyl}methyl)pyrazole-4-carboxamide |
| 117 | N-[(2,6-difluoro-3-methoxyphenyl)methyl]-3-(methoxymethyl)-1-{[2-(methylamino)pyridin-4-yl]methyl}pyrazole-4-carboxamide |
| 118 | N-[(2-fluoro-3-methoxyphenyl)methyl]-3-(methoxymethyl)-1-{[2-(2,2,2-trifluoroethyl)phenyl]methyl}pyrazole-4-carboxamide |
| 119 | N-[(2-fluoro-3-methoxyphenyl)methyl]-3-(methoxymethyl)-1-{[2-(trifluoromethoxy)phenyl]methyl}pyrazole-4-carboxamide |
| 121 | N-[(2-fluoro-3-methoxyphenyl)methyl]-2-methyl-1-({4-[(2-oxopyridin-1-yl)methyl]phenyl}methyl)imidazole-4-carboxamide |

TABLE 12-continued

Compound names

| Example Number | Name |
|---|---|
| 122 | 2-amino-N-[(2-fluoro-3-methoxyphenyl)methyl]-1-({4-[(2-oxopyridin-1-yl)methyl]phenyl}methyl)imidazole-4-carboxamide |
| 123 | 2-cyclopropyl-N-[(2-fluoro-3-methoxyphenyl)methyl]-1-({4-[(2-oxopyridin-1-yl)methyl]phenyl}methyl)imidazole-4-carboxamide |
| 124 | N-[(2-fluoro-3-methoxyphenyl)methyl]-1-({4-[(2-oxopyridin-1-yl)methyl]phenyl}methyl)-2-(trifluoromethyl)imidazole-4-carboxamide |
| 125 | N-[(2-fluoro-3-methoxyphenyl)methyl]-2-(methoxymethyl)-1-({4-[(2-oxopyridin-1-yl)methyl]phenyl}methyl)imidazole-4-carboxamide |
| 126 | N-[(2-fluoro-3-methoxyphenyl)methyl]-1-{[6-(pyrrolidin-1-yl)pyridin-3-yl]methyl}-3-(trifluoromethyl)pyrazole-4-carboxamide |
| 127 | 3-amino-N-[(2-fluoro-3-methoxyphenyl)methyl]-1-{[6-(pyrrolidin-1-yl)pyridin-3-yl]methyl}pyrazole-4-carboxamide |
| 128 | N-[(2-fluoro-3-methoxyphenyl)methyl]-3-(methoxymethyl)-1-{[6-(pyrrolidin-1-yl)pyridin-3-yl]methyl}pyrazole-4-carboxamide |
| 137 | 3-methoxymethyl-1-(6-pyrrolidin-1-yl-pyridin-3-ylmethyl)-1H-pyrazole-4-carboxylic acid 6-cyano-2-fluoro-3-methoxy-benzylamide |
| 138 | 1-(6-pyrrolidin-1-yl-pyridin-3-ylmethyl)-3-trifluoromethyl-1H-pyrazole-4-carboxylic acid 6-cyano-2-fluoro-3-methoxy-benzylamide |
| 139 | 3-amino-N-[(7-chloro-4-methyl-2,3-dihydro-1,4-benzoxazin-2-yl)methyl]-1-({4-[(2-oxopyridin-1-yl)methyl]phenyl}methyl)pyrazole-4-carboxamide |
| 140 | 3-amino-N-[(7-chloro-3,4-dihydro-2H-1,4-benzoxazin-2-yl)methyl]-1-({4-[(2-oxopyridin-1-yl)methyl]phenyl}methyl)pyrazole-4-carboxamide |

TABLE 13

NMR data of examples (solvent d6 DMSO)

| Example Number | Chemical shift |
|---|---|
| 4 | 1.98 (3H, s), 3.82 (3H, s), 4.39 (2H, d, J = 5.7 Hz), 5.22 (2H, s), 5.40 (2H, s), 6.86-6.90 (1H, m), 7.04-7.10 (2H, m), 7.19-7.29 (5H, m), 7.53 (1H, s), 8.43 (1H, s), 8.74 (1H, t, J = 5.7 Hz) |
| 5 | 1.87 (3H, s), 3.72 (3H, s), 4.35 (2H, d, J = 5.9 Hz), 5.22 (2H, s), 5.41 (2H, s), 6.80-6.86 (3H, m), 7.20 (2H, d, J = 8.2 Hz), 7.23-7.29 (4H, m), 7.53 (1H, s), 8.42 (1H, s), 8.75 (1H, br. s) |
| 6 | 1.30 (3H, t, J = 6.9 Hz), 1.98 (3H, s), 3.99 (2H, q, J = 7.0 Hz), 4.34 (2H, d, J = 5.9 Hz), 5.22 (2H, s), 5.41 (2H, s), 6.78-6.84 (3H, m), 7.19-7.27 (6H, m), 7.53 (1H, s), 8.43 (1H, s), 8.75 (1H, t, J = 5.8 Hz) |
| 7 | 1.98 (3H, s), 4.42 (2H, d, J = 6.0 Hz), 5.22 (2H, s), 5.41(2H, s), 7.19-7.33 (8H, m), 7.46 (1H, t, J = 7.7 Hz), 7.53 (1H, s), 8.43 (1H, s), 8.86 (1H, t, J = 5.9 Hz) |
| 8 | 1.98 (3H, s), 2.27 (3H, s), 4.32 (2H, d, J = 5.8 Hz), 5.22 (2H, s), 5.40 (2H, s), 7.11-7.23 (9H, m), 7.54 (1H, s), 8.42 (1H, s), 8.75 (1H, t, J = 5.9 Hz) |
| 9 | 1.98 (3H, s), 3.70 (3H, s), 4.37 (2H, d, J = 5.7 Hz), 5.23 (2H, s), 5.41 (2H, s), 6.84-6.87 (2H, m), 7.09-7.13 (1H, m), 7.21-7.29 (5H, m), 7.54 (1H, s), 8.44 (1H, s), 8.77 (1H, t, J = 5.7 Hz) |
| 10 | 1.98 (3H, s), 3.74 (3H, s), 3.78 (3H, s), 4.25 (2H, d, J = 5.6 Hz), 5.23 (2H, s), 5.40 (2H, s), 6.47 (1H, dd, J = 8.4, 2.4 Hz), 6.54 (1H, d, J = 2.3 Hz), 7.09 (1H, d, J = 8.3 Hz), 7.20 (2H, d, J = 8.2 Hz), 7.24 (1H, s), 7.28 (2H, d, J = 8.1 Hz), 7.54 (1H, s), 8.44 (1H, d, J = 0.6), 8.51 (1H, t, J = 5.6 Hz) |
| 11 | 1.98 (3H, s), 3.77 (3H, s), 4.33 (2H, d, J = 5.0 Hz), 5.22 (2H, s), 5.38 (2H, s), 6.74 (2H, d, J = 9.7 Hz), 7.19 (2H, d, J = 8.1 Hz), 7.24 (2H, d, J = 3.7 Hz), 7.26 (1H, s), 7.54 (1H, s), 8.37 (1H, s), 8.55 (1H, t, J = 5.0 Hz) |
| 12 | 1.98 (3H, s), 3.81 (3H, s), 4.47 (2H, d, J = 5.2 Hz), 5.23 (2H, s), 5.42 (2H, s), 7.20-7.24 (5H, m), 7.29 (2H, d, J = 8.0 Hz), 7.44 (1H, d, J = 8.2 Hz), 7.54 (1H, s), 8.46 (1H, s), 8.78 (1H, t, J = 4.8 Hz) |
| 13 | 1.98 (3H, s), 4.42 (2H, d, J = 5.1 Hz), 5.22 (2H, s), 5.38 (2H, s), 7.06-7.09 (2H, m), 7.10-7.13 (2H, m), 7.18-7.26 (3H, m), 7.37-7.44 (1H, m), 7.54 (1H, s), 8.38 (1H, s), 8.65 (1H, t, J = 5.1 Hz) |
| 14 | 1.98 (3H, s), 4.49-4.50 (2H, m), 5.21 (2H, s), 5.38 (2H, s), 7.18 (2H, d, J = 8.2 Hz), 7.23-7.27 (4H, m), 7.34-7.43 (2H, m), 7.54 (1H, s), 8.38 (1H, s), 8.55 (1H, t, J = 4.8 Hz) |
| 15 | 1.98 (3H, s), 4.52 (2H, d, J = 3.9 Hz), 5.21 (2H, s), 5.38 (2H, s), 7.18 (2H, d, J = 8.1 Hz), 7.23-7.25 (3H, m), 7.53 (1H, s), 7.58-7.63 (3H, m), 8.35 (1H, s), 8.51 (1H, t, J = 4.3 Hz) |
| 16 | 1.98 (3H, s), 4.38 (2H, d, J = 5.1 Hz), 5.22 (2H, s), 5.39 (2H, s), 7.18 (1H, s), 7.20 (1H, s), 7.24 (2H, d, J = 4.5 Hz), 7.27 (1H, s), 7.38 (2H, d, J = 7.4 Hz), 7.54 (1H, s), 8.36 (1H, s), 8.67 (1H, t, J = 5.1 Hz) |
| 17 | 1.98 (3H, s), 4.38 (2H, d, J = 5.6 Hz), 5.23 (2H, s), 5.41 (2H, s), 7.19 (1H, s), 7.21 (1H, s), 7.24 (1H, s), 7.26-7.29 (3H, m), 7.37 (1H, t, J = 8.2 Hz), 7.43 (1H, dd, J = 10.0, 2.0 Hz), 7.55 (1H, s), 8.44 (1H, s), 8.82 (1H, t, J = 5.8 Hz) |
| 18 | 1.98 (3H, s), 4.44 (2H, d, J = 5.2 Hz), 5.22 (2H, s), 5.39 (2H, s), 7.18-7.27 (6H, m), 7.53 (1H, s), 7.58-7.62 (1H, m), 8.46 (1H, s), 8.71 (1H, t, J = 5.2 Hz) |
| 19 | 1.98 (3H, s), 4.44 (2H, d, J = 5.6 Hz), 5.23 (2H, s), 5.41 (2H, s), 7.19-7.23 (4H, m), 7.27-7.32 (3H, m), 7.47-7.51 (1H, m), 7.53 (1H, s), 8.44 (1H, s), 8.82 (1H, t, J = 5.6 Hz) |

TABLE 13-continued

NMR data of examples (solvent d6 DMSO)

| Example Number | Chemical shift |
|---|---|
| 20 | 1.98 (3H, s), 4.39 (2H, d, J = 5.7 Hz), 5.23 (2H, s), 5.41 (2H, s), 7.19-7.30 (6H, m), 7.36-7.40 (2H, m), 7.54 (1H, s), 8.45 (1H, s), 8.80 (1H, t, J = 5.7 Hz) |
| 21 | 1.98 (3H, s), 4.56 (2H, d, J = 3.7 Hz), 5.21 (2H, s), 5.39 (2H, s), 7.19 (2H, d, J = 8.1 Hz), 7.24 (2H, d, J = 2.8 Hz), 7.26 (1H, s), 7.53 (1H, s), 7.65 (1H, d, J = 8.6 Hz), 7.82 (1H, t, J = 7.8 Hz), 8.35 (1H, s), 8.54 (1H, t, J = 4.2 Hz) |
| 22 | 1.98 (3H, s), 4.61 (2H, d, J = 4.4 Hz), 5.21 (2H, s), 5.38 (2H, s), 7.18 (2H, d, J = 8.2 Hz), 7.22-7.26 (3H, m), 7.38-7.40 (1H, m), 7.49-7.53 (3H, m), 8.38 (1H, s), 8.45 (1H, t, J = 4.3 Hz) |
| 23 | 1.98 (3H, s), 4.54 (2H, d, J = 5.6 Hz), 5.23 (2H, s), 5.44 (2H, s), 7.20-7.24 (3H, m), 7.30 (2H, d, J = 8.1 Hz), 7.53 (2H, d, J = 5.5 Hz), 7.57 (1H, d, J = 8.5 Hz), 7.77 (1H, d, J = 8.4 Hz), 8.49 (1H, s), 8.90 (1H, t, J = 5.8 Hz) |
| 24 | 1.98 (3H, s), 2.24 (6H, s), 4.31 (2H, d, J = 5.6 Hz), 5.22 (2H, s), 5.40 (2H, s), 6.95 (1H, d, J = 7.7 Hz), 6.98 (1H, s), 7.10 (1H, d, J = 7.6 Hz), 7.18-7.29 (5H, m), 7.54 (1H, s), 8.44 (1H, s), 8.60 (1H, t, J = 5.6 Hz) |
| 25 | 1.97 (3H, s), 2.31 (6H, s), 4.38 (2H, d, J = 4.7 Hz), 5.21 (2H, s), 5.36 (2H, s), 7.01 (1H, s), 7.03 (1H, s), 7.07-7.11 (1H, m), 7.16 (1H, s), 7.18 (1H, s), 7.23 (2H, d, J = 3.5 Hz), 7.25 (1H, s), 7.53 (1H, s), 8.26 (1H, t, J = 5.0 Hz), 8.38 (1H, s) |
| 26 | 1.97 (3H, s), 2.20 (3H, s), 2.26 (6H, s), 4.34 (2H, d, J = 4.8 Hz), 5.21 (2H, s), 5.36 (2H, s), 6.84 (2H, s), 7.17 (2H, d, J = 8.1 Hz), 7.23-7.25 (3H, m), 7.53 (1H, s), 8.20 (1H, t, J = 4.7 Hz), 8.38 (1H, s) |
| 27 | 1.98 (3H, s), 2.19 (3H, d, J = 1.7 Hz), 4.38 (2H, d, J = 5.6 Hz), 5.22 (2H, s), 5.40 (2H, s), 7.04-7.09 (2H, m), 7.16-7.29 (6H, m), 7.53 (1H, s), 8.44 (1H, s), 8.68 (1H, t, J = 5.2 Hz) |
| 28 | 1.98 (3H, s), 2.29 (3H, s), 4.35 (2H, d, J = 5.7 Hz), 5.23 (2H, s), 5.40 (2H, s), 6.98 (1H, d, J = 8.1 Hz), 7.01 (1H, d, J = 11.6 Hz), 7.19-7.22 (3H, m), 7.24 (1H, s), 7.27 (1H, s), 7.29 (1H, s), 7.55 (1H, s), 8.44 (1H, s), 8.75 (1H, t, J = 5.7 Hz) |
| 29 | 1.99 (3H, s), 4.55 (2H, dd, J = 5.5, 1.4 Hz), 5.23 (2H, s), 5.41 (2H, s), 7.19-7.24 (3H, m), 7.28 (2H, d, J = 8.2 Hz), 7.38-7.43 (1H, m), 7.54 (1H, s), 7.67-7.72 (1H, m), 8.36-8.38 (1H, m), 8.44 (1H, s), 8.76 (1H, t, J = 4.2 Hz) |
| 30 | 1.99 (3H, s), 4.49 (2H, d, J = 5.9 Hz), 5.24 (2H, s), 5.43 (2H, s), 7.20-7.25 (3H, m), 7.30-7.31 (2H, m), 7.49-7.50 (2H, m), 7.55 (1H, s), 8.52 (2H, d, J = 5.8 Hz), 8.97 (1H, d, J = 5.9 Hz) |
| 31 | 3.20 (3H, m), 4.53 (2H, d, J = 2.9 Hz), 4.59 (2H, d, J = 5.2 Hz), 5.06 (2H, s), 5.30 (2H, s), 6.19-6.27 (1H, m), 6.40 (1H, d, J = 9.2 Hz), 7.18-7.34 (4H, m), 7.36-7.47 (1H, m), 7.76 (2H, t, J = 6.4 Hz), 8.24-8.37 (1H, s), 8.54 (1H, s), 8.74-8.86 (2H, m) |
| 32 | 2.73 (3H, s), 3.22 (3H, s), 4.46-4.58 (4H, m), 5.08 (2H, s), 5.30 (2H, s), 6.20-6.27 (1H, m), 6.40 (1H, d, J = 9.1 Hz), 7.20-7.32 (4H, m), 7.42 (1H, ddd, J = 2.1, 6.6, 8.8 Hz), 7.78 (1H, dd, J = 1.5, 6.8 Hz), 7.88 (1H, d, J = 8.3 Hz), 8.30 (1H, s), 8.39 (1H, dd, J = 2.0, 8.3 Hz), 8.64-8.76 (2H, m) |
| 36 | 3.21 (3H, s), 4.54 (2H, s), 4.58 (2H, d, J = 5.7 Hz), 5.07 (2H, s), 5.30 (2H, s), 6.22 (1H, td, J = 6.7, 1.4 Hz), 6.39 (1H, d, J = 9.2 Hz), 7.20-7.31 (4H, m), 7.41 (1H, ddd, J = 8.9, 6.6, 2.1 Hz), 7.70 (1H, dd, J = 7.9, 4.7 Hz), 7.76 (1H, dd, J = 6.8, 2.1 Hz), 7.97 (1H, d, J = 7.8 Hz), 8.28 (1H, s), 8.50 (1H, t, J = 5.8 Hz), 8.62 (1H, d, J = 4.9 Hz) |
| 37 | 3.20 (3H, m), 4.53 (2H, d, J = 2.9 Hz), 4.59 (2H, d, J = 5.2 Hz), 5.06 (2H, s), 5.30 (2H, s), 6.19-6.27 (1H, m), 6.40 (1H, d, J = 9.2 Hz), 7.18-7.34 (4H, m), 7.36-7.47 (1H, m), 7.76 (2H, t, J = 6.4 Hz), 8.24-8.37 (1H, s), 8.54 (1H, s), 8.74-8.86 (2H, m) |
| 39 | 2.73 (3H, s), 3.22 (3H, s), 4.46-4.58 (4H, m), 5.08 (2H, s), 5.30 (2H, s), 6.20-6.27 (1H, m), 6.40 (1H, d, J = 9.1 Hz), 7.20-7.32 (4H, m), 7.42 (1H, ddd, J = 2.1, 6.6, 8.8 Hz), 7.78 (1H, dd, J = 1.5, 6.8 Hz), 7.88 (1H, d, J = 8.3 Hz), 8.30 (1H, s), 8.39 (1H, dd, J = 2.0, 8.3 Hz), 8.64-8.76 (2H, m) |
| 40 | 3.21 (3H, s), 3.83 (3H, s), 4.40 (2H, d, J = 5.8 Hz), 4.55 (2H, s), 5.07 (2H, s), 5.30 (2H, s), 6.22 (1H, dt, J = 1.4, 6.6 Hz), 6.40 (1H, ddd, J = 0.7, 1.4, 9.1 Hz), 6.67 (1H, dd, J = 0.8, 8.2 Hz), 6.88 (1H, dd, J = 0.8, 7.3 Hz), 7.22-7.29 (4H, m), 7.41 (1H, ddd, J = 2.1, 6.6, 9.2 Hz), 7.65 (1H, dd, J = 7.3, 8.2 Hz), 7.76 (1H, ddd, J = 0.8, 2.1, 6.8 Hz), 8.28 (1H, s), 8.42 (1H, t, J = 5.8 Hz) |
| 41 | 3.25 (3H, s), 3.92 (3H, s), 4.46-4.57 (4H, m), 5.07 (2H, s), 5.28 (2H, s), 6.22 (1H, td, J = 1.4, 6.7 Hz), 6.39 (1H, ddd, J = 0.7, 1.4, 9.2 Hz), 7.17-7.28 (5H, m), 7.41 (1H, ddd, J = 2.1, 6.6, 8.9 Hz), 7.75 (1H, ddd, J = 0.7, 2.1, 6.8 Hz), 8.21-8.29 (2H, m), 8.42 (1H, t, J = 5.4 Hz) |
| 42 | 3.21 (3H, s), 3.79 (3H, s), 4.49 (2H, dd, J = 2.0, 5.5 Hz), 4.54 (2H, s), 5.07 (2H, s), 5.29 (2H, s), 6.23 (1H, td, J = 1.4, 6.7 Hz), 6.38-6.43 (1H, m), 6.77 (1H, dd, J = 3.0, 8.9 Hz), 7.20-7.25 (2H, m), 7.25-7.30 (2H, m), 7.41 (1H, ddd, J = 2.1, 6.6, 8.9 Hz), 7.65 (1H, t, J = 8.9 Hz), 7.76 (1H, dd, J = 1.5, 6.8 Hz), 8.26 (1H, s), 8.31 (1H, t, J = 5.5 Hz) |
| 45 | 3.17 (3H, s), 4.53 (2H, s), 4.61 (2H, d, J = 5.7 Hz), 5.06 (2H, s), 5.27 (2H, s), 6.21 (1H, dt, J = 6.8, 1.3 Hz), 6.39 (1H, d, J = 9.3 Hz), 7.22 (2H, d, J = 8.2 Hz), 7.26 (2H, d, J = 8.3 Hz), 7.38-7.42 (2H, m), 7.69 (1H, s), 7.75 (1H, dd, J = 6.8, 1.8 Hz), 7.99 (1H, d, J = 2.0 Hz), 8.02 (1H, d, J = 8.6 Hz), 8.22 (1H, s), 8.36-8.43 (1H, m) |
| 46 | 1.91-1.93 (4H, m), 3.19 (3H, s), 3.31-3.36 (4H, m), 4.54 (2H, s), 4.61 (2H, d, J = 5.7 Hz), 5.12 (2H, s), 6.40 (1H, d, J = 8.7 Hz), 7.40 (1H, dd, J = 8.6, 2.0 Hz), 7.43 (1H, dd, J = 8.7, 2.4 Hz), 7.68 (1H, d, J = 2.0 Hz), 7.98 (1H, d, J = 2.0 Hz), 8.01 (1H, s), 8.03 (1H, s), 8.08 (1H, d, J = 2.2 Hz), 8.14 (1H, s), 8.38 (1H, t, J = 5.2 Hz) |
| 47 | 1.98 (3H, s), 3.17 (3H, s), 4.53 (2H, s), 4.61 (2H, d, J = 5.6 Hz), 5.20 (2H, s), 5.27 (2H, s), 7.17 (2H, d, J = 8.2 Hz), 7.21 (2H, d, J = 8.2 Hz), 7.22 (1H, s), 7.41 (1H, dd, J = 8.6, 2.0 Hz), 7.52 (1H, s), 7.69 (1H, s), 7.99 (1H, d, J = 2.0 Hz), 8.03 (1H, d, J = 8.6 Hz), 8.22 (1H, s), 8.40 (1H, t, J = 5.7 Hz) |

TABLE 13-continued

NMR data of examples (solvent d6 DMSO)

| Example Number | Chemical shift |
|---|---|
| 48 | 0.72-0.75 (2H, m), 0.80-0.84 (2H, m), 2.50-2.55 (1H, m), 4.52 (2H, d, J = 5.9 Hz), 5.06 (2H, s), 5.19 (2H, s), 6.21-6.25 (1H, m), 6.39 (1H, d, J = 9.0 Hz), 7.18 (2H, d, J = 8.2 Hz), 7.25 (2H, d, J = 8.2 Hz), 7.27-7.30 (1H, m), 7.35-7.49 (4H, m), 7.77 (1H, dd, J = 1.9, 6.8 Hz), 7.80 (1H, s), 7.98 (1H, s), 8.14 (1H, s), 8.31 (1H, t, J = 6.0 Hz) |
| 49 | 0.72-0.76 (2H, m), 0.79-0.84 (2H, m), 2.52-2.64 (1H, m), 4.40 (2H, d, J = 5.9 Hz), 5.06 (2H, s), 5.19 (2H, s), 6.20-6.24 (1H, m), 6.39 (1H, d, J = 8.8 Hz), 7.18 (2H, d, J = 8.2 Hz), 7.25 (2H, d, J = 8.1 Hz), 7.38-7.44 (4H, m), 7.72-7.77 (2H, m), 7.80 (1H, s), 7.95 (1H, s), 8.11 (1H, s), 8.40 (1H, t, J = 5.9 Hz) |
| 50 | 0.73-0.76 (2H, m), 0.79-0.84 (2H, m), 2.57-2.62 (1H, m), 4.41 (2H, d, J = 5.9 Hz), 5.07 (2H, s), 5.19 (2H, s), 6.21-6.24 (1H, m), 6.39 (1H, d, J = 8.8 Hz), 7.18 (2H, d, J = 8.2 Hz), 7.25 (2H, d, J = 8.1 Hz), 7.27-7.35 (4H, m), 7.39-7.43 (1H, m), 7.76 (1H, dd, J = 1.9, 6.5 Hz), 7.81 (1H, d, J = 8.2 Hz), 7.91 (1H, s), 8.11 (1H, s), 8.20 (1H, t, J = 6.0 Hz) |
| 51 | 4.52 (2H, d, J = 3.9 Hz), 5.06 (2H, s), 5.31 (2H, s), 6.20-6.24 (1H, m), 6.38 (1H, t, J = 9.0 Hz), 7.26 (4H, s), 7.39-7.45 (1H, m), 7.63 (3H, t, J = 2.0 Hz), 7.76 (1H, dd J = 4.8, 1.9 Hz), 8.35 (1H, s), 8.51 (1H, t, J = 4.5 Hz) |
| 52 | 0.72-0.75 (2H, m), 0.79-0.82 (2H, m), 2.56-2.62 (1H, m), 3.82 (3H, s), 4.39 (2H, d, J = 5.7 Hz), 5.06 (2H, s), 5.18 (2H, s), 6.21-6.24 (1H, m), 6.39 (1H, d, J = 8.9 Hz), 6.86-6.90 (1H, m), 7.04-7.07 (2H, m), 7.18 (2H, d, J = 8.1 Hz), 7.25 (2H, d, J = 8.1 Hz), 7.39-7.43 (1H, m), 7.76 (1H, q, J = 5.1 Hz), 8.12 (1H, s), 8.35 (1H, t, J = 5.9 Hz) |
| 53 | 3.2 (3H, s), 3.82 (3H, s), 4.41 (2H, d, J = 5.6 Hz), 4.52 (2H, s), 5.07 (2H, s), 5.28 (2H, s), 6.22 (1H, td, J = 6.7, 1.4 Hz), 6.39 (1H, d, J = 9.8 Hz), 6.86-6.90 (1H, m), 7.05-7.10 (2H, m), 7.22-7.27 (4H, m), 7.39-7.43 (1H, m), 7.76 (1H, dd, J = 6.8, 1.9 Hz), 8.24 (1H, s), 8.34 (1H, t, J = 5.7 Hz) |
| 54 | 3.16 (3H, s), 3.77 (6H, d, J = 1.8 Hz), 4.39 (2H, dd, J = 1.6, 5.2 Hz), 4.45 (2H, s), 5.05 (2H, s), 5.25 (2H, s), 6.21 (1H, td, J = 1.4, 6.7 Hz), 6.36-6.40 (1H, m), 6.76 (1H, dd, J = 1.7, 9.1 Hz), 7.05 (1H, t, J = 9.4 Hz), 7.17-7.27 (4H, m); 7.40 (1H, ddd, J = 2.1, 6.6, 8.9 Hz), 7.74 (1H, dd, J = 2.1, 6.8 Hz), 7.95 (1H, t, J = 5.1 Hz), 8.21 (1H, s) |
| 58 | 4.36 (2H, d, J = 5.9 Hz), 5.04 (2H, s), 5.07 (2H, s), 5.37 (2H, s), 6.21-6.24 (1H, m), 6.39 (1H, d, J = 9.1 Hz), 7.20 (2H, d, J = 8.1 Hz), 7.26 (2H, d, J = 8.1 Hz), 7.27-7.31 (2H, m), 7.38-7.43 (3H, m), 7.76 (1H, dd, J = 2.0, 6.8 Hz), 7.97 (1H, s), 8.35 (1H, t, J = 5.9 Hz) |
| 59 | 2.72 (6H, s), 3.82 (3H, s), 4.41 (2H, d, J = 5.6 Hz), 5.07 (2H, s), 5.17 (2H, s), 6.21-6.25 (1H, m), 6.40 (1H, d, J = 8.8 Hz), 6.86-6.89 (1H, m), 7.04-7.07 (2H, m), 7.21-7.25 (4H, m), 7.39-7.41 (1H, m), 7.76 (1H, dd, J = 6.9, 1.6 Hz), 8.07 (1H, s), 8.35 (1H, t, J = 5.8 Hz) |
| 62 | 3.20 (3H, s), 4.42 (2H, J = 5.7 Hz), 4.53 (2H, s), 5.07 (2H, s), 5.28 (2H, s), 6.22 (1H, td, J = 6.7, 1.4 Hz), 6.39 (1H, d, J = 9.2 Hz), 7.13-7.38 (8H, m), 7.41 (1H, ddd, J = 8.9, 6.6, 2.1 Hz), 7.76 (1H, dd, J = 6.8, 2.1 Hz), 8.25 (1H, s), 8.35 (1H, t, J = 5.8 Hz) |
| 63 | 3.20 (3H, s), 4.53 (2H, s), 4.57 (2H, d, J = 5.7 Hz), 5.07 (2H, s), 5.30 (2H, s), 6.22 (1H, td, J = 6.7, 1.4 Hz), 6.40 (1H, d, J = 9.1 Hz), 7.22-7.31 (4H, m), 7.41 (1H, ddd, J = 8.9, 6.5, 2.1 Hz), 7.47 (1H, t, J = 7.6 Hz), 7.54 (1H, d, J = 7.7 Hz), 7.65 (1H, t, J = 7.6 Hz), 7.72 (1H, d, J = 7.7 Hz), 7.76 (1H, dd, J = 6.8, 2.1 Hz), 8.29 (1H, s), 8.43 (1H, t, J = 5.8 Hz) |
| 64 | 3.20 (3H, s), 3.70 (3H, s), 4.38 (2H, d, J = 5.7 Hz), 4.52 (2H, s), 5.07 (2H, s), 5.28 (2H, s), 6.22 (1H, td, J = 6.7, 1.4 Hz), 6.39 (1H, d, J = 9.1 Hz), 6.80-6.81 (2H, m), 7.10 (1H, dd, J = 9.6, 8.9 Hz), 7.20-7.30 (4H, m), 7.41 (1H, ddd, J = 9.2, 6.6, 2.1 Hz), 7.76 (1H, dd, J = 6.8, 2.1 Hz), 8.25 (1H, s), 8.33 (1H, t, J = 5.7 Hz) |
| 65 | 2.28 (3H, s), 3.20 (3H, s), 4.37 (2H, d, J = 5.7 Hz), 4.52 (2H, s), 5.06 (2H, s), 5.28 (2H, s), 6.22 (1H, td, J = 6.7, 1.4 Hz), 6.39 (1H, d, J = 9.1 Hz), 6.93-7.04 (2H, m), 7.18-7.30 (5H, m), 7.41 (1H, ddd, J = 9.2, 6.6, 2.1 Hz), 7.75 (1H, dd, J = 6.8, 2.1 Hz), 8.24 (1H, s), 8.30 (1H, t, J = 5.7 Hz), |
| 66 | 3.20 (3H, s), 3.81 (3H, s), 4.43 (2H, d, J = 5.3 Hz), 4.49 (2H, s), 5.06 (2H, s), 5.26 (2H, s), 6.21 (1H, dt, J = 1.4, 6.7 Hz), 6.39 (1H, ddd, J = 0.7, 1.4, 9.1 Hz), 7.02 (1H, dt, J = 1.9, 9.2 Hz), 7.12 (1H, dt, J = 5.3, 9.3 Hz), 7.18-7.27 (4H, m), 7.40 (1H, ddd, J = 2.1, 6.6, 9.2 Hz), 7.75 (1H, ddd, J = 0.7, 2.1, 6.8 Hz), 8.21 (1H, s), 8.24 (1H, t, J = 5.3 Hz) |
| 67 | 3.21 (3H, s), 3.75 (3H, s), 4.35 (2H, d, J = 5.9 Hz), 4.54 (2H, s), 5.07 (2H, s), 5.29 (2H, s), 6.22 (1H, dt, J = 1.4, 6.7 Hz), 6.40 (1H, ddd, J = 0.7, 1.4, 9.2 Hz), 6.82 (1H, dd, J = 1.4, 2.4 Hz), 6.87-6.93 (2H, m), 7.21-7.31 (4H, m), 7.41 (1H, ddd, J = 2.1, 6.6, 9.2 Hz), 7.76 (1H, ddd, J = 0.7, 2.1, 6.8 Hz), 8.24 (1H, s), 8.39 (1H, t, J = 5.9 Hz) |
| 68 | 3.18 (3H, d, J = 0.7 Hz), 4.53 (4H, d, J = 8.8 Hz), 5.07 (2H, s), 5.29 (2H, s), 6.22 (1H, tt, J = 1.0, 6.7 Hz), 6.39 (1H, d, J = 9.2 Hz), 7.13-7.45 (8H, m), 7.51 (1H, t, J = 7.5 Hz), 7.58 (1H, d, J = 7.7 Hz), 7.76 (1H, dd, J = 2.0, 6.8 Hz), 8.25 (1H, s), 8.39 (1H, t, J = 5.9 Hz) |
| 69 | 3.19 (3H, s), 3.83 (3H, s), 4.52 (2H, s), 4.59 (2H, d, J = 5.8 Hz), 5.07 (2H, s), 5.29 (2H, s), 6.22 (1H, td, J = 1.4, 6.7 Hz), 6.39 (1H, dt, J = 1.0, 9.1 Hz), 7.01 (1H, d, J = 7.8 Hz), 7.06 (1H, d, J = 8.4 Hz), 7.14-7.48 (7H, m), 7.76 (1H, ddd, J = 0.7, 2.1, 6.8 Hz), 8.27 (1H, s), 8.34 (1H, t, J = 5.9 Hz) |
| 70 | 4.14 (2H, d, J = 6.2 Hz), 4.55 (2H, br.s), 5.04 (2H, s), 6.20 (1H, td, J = 6.7, 1.3 Hz), 6.38 (1H, d, J = 9.2 Hz), 7.20-7.29 (4H, m), 7.37-7.42 (1H, m), 7.57 (1H, d, J = 3.8 Hz), 7.60 (3H, br.s), 7.74 (2H, dd, J = 6.7, 1.9 Hz), 8.40 (1H, br.s), 12.01-12.19 (1H, m) |
| 71 | 1.98 (3H, s), 3.83 (3H, s), 4.41 (2H, d, J = 5.8 Hz), 5.04 (2H, s), 5.59 (2H, s), 6.22 (1H, td, J = 6.7, 1.4 Hz), 6.39 (1H, dd, J = 9.1, 0.5 Hz), 6.79-6.83 (1H, m), 7.03-7.05 (2H, m), 7.08-7.10 (2H, m), 7.19 (1H, s), 7.21 (1H, s), 7.22 (1H, s), 7.39-7.43 (1H, m), 7.74 (1H, dd, J = 6.7, 1.9 Hz), 9.13 (1H, t, J = 5.9 Hz), 10.53 (1H, s) |
| 72 | 1.93 (3H, s), 3.10 (3H, s), 3.83 (3H, s), 4.42 (2H, d, J = 4.8 Hz), 5.05 (2H, s), 5.64 (2H, s), 6.22 (1H, td, J = 6.7, 1.3 Hz), 6.40 (1H, d, J = 9.5 Hz), 6.79-6.81 (1H, m), 6.87 (1H, br.s), 7.03-7.06 (2H, m), 7.07-7.11 (2H, m), 7.18-7.21 (2H, m), 7.39-7.44 (1H, m), 7.75 (1H, dd, J = 6.8, 1.9 Hz), 9.08 (1H, br.s) |

TABLE 13-continued

NMR data of examples (solvent d6 DMSO)

| Example Number | Chemical shift |
|---|---|
| 73 | 3.22 (3H, s), 4.46 (2H, d, J = 5.3 Hz), 4.51 (2H, s), 5.07 (2H, s), 5.27 (2H, s), 6.22 (1H, td, J = 1.4, 6.7 Hz), 6.40 (1H, d, J = 8.5 Hz), 7.15-7.29 (5H, m), 7.38-7.46 (1H, m), 7.54-7.64 (1H, m), 7.76 (1H, dd, J = 1.5, 6.8 Hz), 8.20 (1H, s), 8.34 (1H, t, J = 5.4 Hz) |
| 76 | 3.22 (3H, s), 4.54 (4H, m), 5.07 (2H, s), 5.30 (2H, s), 6.22 (1H, td, J = 1.4, 6.7 Hz), 6.40 (1H, ddd, J = 0.7, 1.4, 9.1 Hz), 7.20-7.30 (4H, m), 7.41 (1H, ddd, J = 2.1, 6.6, 9.2 Hz), 7.52-7.59 (2H, m), 7.76 (1H, ddd, J = 0.7, 2.1, 6.8 Hz), 7.84-7.91 (1H, m), 8.26 (1H, s), 8.58 (1H, t, J = 5.7 Hz) |
| 77 | 3.21 (3H, s), 3.92 (3H, s), 4.47-4.55 (4H, m), 5.06 (2H, s), 5.27 (2H, s), 6.21 (1H, td, J = 6.7, 1.4 Hz), 6.39 (1H, d, J = 9.1 Hz), 7.17-7.31 (5H, m), 7.40 (1H, ddd, J = 8.9, 6.6, 2.1 Hz), 7.67 (1H, dd, J = 8.6, 1.5 Hz), 7.75 (1H, dd, J = 6.8, 2.1 Hz), 8.20 (1H, s), 8.40 (1H, t, J = 5.2 Hz) |
| 78 | 3.20 (3H, s), 3.86 (3H, s), 4.49-4.56 (4H, m), 5.07 (2H, s), 5.29 (2H, s), 6.22 (1H, td, J = 1.4, 6.7 Hz), 6.39 (1H, ddd, J = 0.7, 1.4, 9.2 Hz), 7.07 (1H, d, J = 7.8 Hz), 7.18 (1H, d, J = 8.4 Hz), 7.22-7.29 (4H, m), 7.39-7.44 (1H, m), 7.55 (1H, t, J = 8.1 Hz), 7.76 (1H, ddd, J = 0.7, 2.1, 6.8 Hz), 8.27 (1H, s), 8.34 (1H, t, J = 5.8 Hz) |
| 79 | 3.20 (3H, s), 3.79 (3H, s), 4.53 (4H, m), 5.07 (2H, s), 5.30 (2H, s), 6.22 (1H, td, J = 1.4, 6.7 Hz), 6.40 (1H, dt, J = 1.0, 9.1 Hz), 6.96-7.05 (2H, m), 7.22-7.31 (4H, m), 7.41 (1H, ddd, J = 2.1, 6.6, 8.9 Hz), 7.66 (1H, d, J = 8.6 Hz), 7.76 (1H, ddd, J = 0.7, 2.1, 6.8 Hz), 8.29 (1H, s), 8.40 (1H, t, J = 5.8 Hz) |
| 80 | 3.16 (3H, s), 4.43-4.52 (4H, m), 5.05 (2H, s), 5.26 (2H, s), 6.21 (1H, td, J = 1.4, 6.7 Hz), 6.39 (1H, dt, J = 1.0, 9.2 Hz), 7.23 (4H, q, J = 8.3 Hz), 7.31-7.62 (5H, m), 7.75 (1H, ddd, J = 0.7, 2.1, 6.8 Hz), 8.22 (1H, s), 8.33 (1H, t, J = 5.4 Hz) |
| 81 | 3.18 (3H, s), 3.76 (3H, s), 4.51 (4H, m), 5.07 (2H, s), 5.29 (2H, s), 6.22 (1H, td, J = 1.4, 6.7 Hz), 6.40 (1H, dt, J = 1.2, 9.0 Hz), 6.88-6.98 (2H, m), 7.03-7.33 (5H, m), 7.41 (1H, ddd, J = 2.1, 6.6, 8.9 Hz), 7.51 (1H, d, J = 9.1 Hz), 7.76 (1H, ddd, J = 0.7, 2.1, 6.8 Hz), 8.26 (1H, s), 8.38 (1H, t, J = 5.8 Hz) |
| 83 | 3.12 (3H, s), 3.83 (3H, s), 4.43 (2H, s), 4.52-4.59 (2H, m), 5.05 (2H, s), 5.25 (2H, s), 6.21 (1H, td, J = 1.4, 6.7 Hz), 6.39 (1H, dt, J = 1.0, 9.2 Hz), 7.15-7.44 (8H, m), 7.75 (1H, ddd, J = 0.7, 2.1, 6.8 Hz), 8.08 (1H, t, J = 4.9 Hz), 8.22 (1H, s) |
| 85 | 3.17 (3H, s), 4.44 (2H, s), 4.54 (2H, d, J = 5.2 Hz), 5.05 (2H, s), 5.25 (2H, s), 6.21 (1H, td, J = 6.7, 1.4 Hz), 6.39 (1H, d, J = 9. 2 Hz), 7.14-7.32 (6H, m), 7.34-7.44 (2H, m), 7.60 (1H, s), 7.75 (1H, dd, J = 6.8, 2.1 Hz), 8.07-8.18 (2H, m), 8.21 (1H, s) |
| 86 | 3.21 (3H, s), 3.74 (3H, s), 4.50 (2H, s), 4.55 (2H, d, J = 5.9 Hz), 5.06 (2H, s), 5.28 (2H, s), 6.22 (1H, td, J = 6.7, 1.4 Hz), 6.39 (1H, d, J = 9.1 Hz), 6.82-6.91 (2H, m), 7.18-7.33 (5H, m), 7.41 (1H, ddd, J = 8.9, 6.6, 2.1 Hz), 7.49 (1H, d, J = 8.4 Hz), 7.76 (1H, d, J = 6.8, 2.1 Hz), 7.81 (1H, br. s), 8.25 (1H, s), 8.30 (1H, t, J = 6.0 Hz) |
| 87 | 3.21 (3H, s), 4.50 (2H, s), 4.70 (2H, d, J = 5.9 Hz), 5.06 (2H, s), 5.28 (2H, s), 6.22 (1H, td, J = 1.4, 6.7 Hz), 6.39 (1H, dd, J = 1.3, 9.1 Hz), 7.21-7.28 (4H, m), 7.32-7.44 (3H, m), 7.51 (1H, td, J = 1.5, 7.5 Hz), 7.76 (1H, dd, J = 2.1, 6.8 Hz), 7.86 (1H, dd, J = 1.4, 7.8 Hz), 8.26 (1H, s), 8.34 (1H, t, J = 5.9 Hz), 13.08 (1H, br. s) |
| 90 | 3.21 (3H, s), 4.45 (2H, d, J = 5.8 Hz), 4.53 (2H, s), 5.07 (2H, s), 5.29 (2H, s), 6.22 (1H, td, J = 6.7, 1.4 Hz), 6.39 (1H, d, J = 9.2 Hz), 7.16-7.31 (7H, m), 7.24 (1H, t, J = 72 Hz), 7.38-7.44 (1H, m), 7.77 (1H, dd, J = 6.8, 2.1 Hz), 8.26 (1H, s), 8.45 (1H, t, J = 5.8 Hz) |
| 91 | 3.20 (3H, s), 4.40 (2H, d, J = 5.9 Hz), 4.54 (2H, s), 5.07 (2H, s), 5.29 (2H, s), 6.22 (1H, td, J = 6.7, 1.4 Hz), 6.39 (1H, d, J = 9.1 Hz), 7.02-7.10 (2H, m), 7.16 (1H, d, J = 7.7 Hz), 7.20 (1H, t, J = 72 Hz), 7.21-7.29 (4H, m), 7.35-7.43 (2H, m), 7.76 (1H, dd, J = 6.8, 2.1 Hz), 8.24 (1H, s), 8.41 (1H, t, J = 5.9 Hz) |
| 92 | 3.18 (3H, s), 4.43 (2H, d, J = 5.3 Hz), 4.47 (2H, s), 5.05 (2H, s), 5.25 (2H, s), 6.21 (1H, td, J = 6.6, 1.4 Hz), 6.39 (1H, d, J = 9.2 Hz), 7.07 (1H, d, J = 8.3 Hz), 7.14 (1H, t, J = 8.5 Hz), 7.20 (2H, d, J = 8.2 Hz), 7.24 (1H, t, J = 72 Hz), 7.25 (2H, d, J = 8.3 Hz), 7.36-7.47 (2H, m), 7.75 (1H, dd, J = 6.8, 2.1 Hz), 8.11 (1H, t, J = 5.1 Hz), 8.20 (1H, s) |
| 94 | 3.21 (3H, s), 4.40 (2H, d, J = 5.8 Hz), 4.53 (2H, s), 5.07 (2H, s), 5.29 (2H, s), 6.22 (1H, td, J = 1.4, 6.7 Hz), 6.39 (1H, dt, J = 1.0, 9.1 Hz), 7.15 (2H, dd, J = 4.9, 8.4 Hz), 7.20-7.30 (5H, m), 7.41 (1H, ddd, J = 2.1, 6.6, 8.9 Hz), 7.76 (1H, ddd, J = 0.7, 2.1, 6.8 Hz), 8.25 (1H, s), 8.40 (1H, t, J = 5.8 Hz) |
| 95 | 3.21 (3H, s), 3.75 (3H, s), 4.36 (2H, d, J = 5.9 Hz), 4.55 (2H, s), 5.08 (2H, s), 5.30 (2H, s), 6.19-6.27 (1H, m), 6.40 (1H, dd, J = 0.6, 9.2 Hz), 6.65-6.75 (3H, m), 7.22-7.31 (4H, m), 7.41 (1H, ddd, J = 2.1, 6.6, 9.0 Hz), 7.73-7.81 (1H, m), 8.25 (1H, s), 8.39 (1H, t, J = 5.9 Hz) |
| 96 | 3.21 (3H, s), 3.84 (3H, s), 4.39 (2H, d, J = 5.7 Hz), 4.53 (2H, s), 5.07 (2H, s), 5.28 (2H, s), 6.22 (1H, td, J = 6.7, 1.4 Hz), 6.39 (1H, d, J = 9.1 Hz), 6.68 (1H, ddd, J = 9.0, 4.9, 3.1 Hz), 7.02 (1H, ddd, J = 10.1, 6.8, 3.1 Hz), 7.19-7.30 (4H, m), 7.41 (1H, ddd, J = 8.9, 6.6, 2.1 Hz), 7.76 (1H, dd, J = 6.8, 2.1 Hz), 8.25 (1H, s), 8.39 (1H, t, J = 5.8 Hz) |
| 97 | 2.37 (3H, s), 3.15 (3H, s), 4.42 (2H, dd, J = 1.7, 5.1 Hz), 4.48 (2H, s), 5.05 (2H, s), 5.25 (2H, s), 6.21 (1H, td, J = 1.4, 6.7 Hz), 6.39 (1H, dt, J = 0.9, 9.2 Hz), 7.02 (2H, dd, J = 8.0, 11.8 Hz), 7.16-7.29 (5H, m), 7.40 (1H, ddd, J = 2.1, 6.6, 8.9 Hz), 7.74 (1H, ddd, J = 0.7, 2.1, 6.8 Hz), 8.04 (1H, t, J = 5.2 Hz), 8.22 (1H, s) |
| 99 | 3.18 (3H, s), 3.84 (3H, s), 4.49 (4H, d, J = 4.9 Hz), 5.06 (2H, s), 5.26 (2H, s), 6.21 (1H, dt, J = 1.4, 6.7 Hz), 6.39 (1H, ddd, J = 0.7, 1.4, 9.1 Hz), 7.12-7.28 (6H, m), 7.40 (1H, ddd, J = 2.1, 6.6, 8.9 Hz), 7.75 (1H, ddd, J = 0.7, 2.1, 6.7 Hz), 8.14 (1H, t, J = 5.1 Hz), 8.21 (1H, s) |
| 129 | 3.20 (3H, s), 4.38 (2H, d, J = 5.6 Hz), 4.52 (2H, s), 5.07 (2H, s), 5.28 (2H, s), 6.21 (1H, dt, J = 6.6, 1.2 Hz), 6.39 (1H, d, J = 9.1 Hz), 6.73 (1H, dt, J = 6.4, 1.4 Hz), 6.83 (1H, dt, J = 8.2, 1.7 Hz), 6.91 (1H, t, J = 7.9 Hz), 7.23 (2H, d, J = 8.3 Hz), 7.26 (2H, d, J = 8.2 Hz), 7.38-7.43 (1H, m), 7.75 (1H, dd, J = 6.8, 1.7 Hz), 8.24 (1H, s), 8.28 (1H, t, J = 5.1 Hz), 9.73 (1H, br. s) |

TABLE 13-continued

NMR data of examples (solvent d6 DMSO)

| Example Number | Chemical shift |
|---|---|
| 130 | 4.35 (2H, d, J = 5.7 Hz), 5.03 (2H, s), 5.07 (2H, s), 5.36 (2H, br. s), 6.22 (1H, dt, J = 6.6, 1.2 Hz), 6.39 (1H, d, J = 8.8 Hz), 6.70 (1H, dt, J = 7.6, 1.4 Hz), 6.82 (1H, dt, J = 8.3, 1.6 Hz), 6.90 (1H, t, J = 7.8 Hz), 7.20 (2H, d, J = 8.1 Hz), 7.26 (2H, d, J = 8.1 Hz), 7.38-7.43 (1H, m), 7.75 (1H, dd, J = 7.0, 1.8 Hz), 7.99 (1H, s), 8.20 (1H, t, J = 5.6 Hz), 9.70 (1H, br. s) |
| 131 | 3.20 (3H, s), 3.84 (3H, s), 4.50 (2H, s), 4.68 (2H, d, J = 5.8 Hz), 5.06 (2H, s), 5.28 (2H, s), 6.22 (1H, dt, J = 1.4, 6.7 Hz), 6.39 (1H, ddd, J = 0.6, 1.3, 9.1 Hz), 7.22-7.28 (4H, m), 7.36-7.43 (2H, m), 7.45 (1H, dd, J = 1.2, 7.9 Hz), 7.56 (1H, dt, J = 1.5, 7.5 Hz), 7.77 (1H, ddd, J = 0.7, 2.1, 6.8 Hz), 7.86 (1H, dd, J = 1.4, 7.8 Hz), 8.26 (1H, s), 8.32 (1H, t, J = 5.9 Hz) |
| 132 | 1.16 (3H, t, J = 7.5 Hz), 2.62 (2H, q, J = 7.6 Hz), 3.20 (3H, s), 4.41 (2H, d, J = 5.7 Hz), 4.52 (2H, s), 5.06 (2H, s), 5.28 (2H, s), 6.22 (1H, td, J = 6.7, 1.4 Hz), 6.39 (1H, d, J = 9.2 Hz), 7.07 (1H, t, J = 7.5 Hz), 7.13-7.30 (6H, m), 7.41 (1H, ddd, J = 8.9, 6.6, 2.1 Hz), 7.77 (1H, dd, J = 6.8, 2.1 Hz), 8.26 (1H, s), 8.35 (1H, t, J = 5.8 Hz) |
| 133 | 3.19 (3H, s), 3.72 (3H, s), 4.35 (2H, d, J = 5.8 Hz), 4.53 (2H, s), 5.06 (2H, s), 5.28 (2H, s), 6.22 (1H, dt, J = 1.4, 6.7 Hz), 6.39 (1H, dt, J = 1.0, 9.1 Hz), 6.78-6.83 (1H, m), 6.83-6.88 (2H, m), 7.18-7.30 (5H, m), 7.41 (1H, ddd, J = 2.1, 6.6, 8.9 Hz), 7.77 (1H, ddd, J = 0.7, 2.1, 6.7 Hz), 8.25 (1H, s), 8.36 (1H, t, J = 5.9 Hz) |
| 104 | 3.20 (3H, s), 3.82 (3H, s), 4.41(2H, d, J = 5.7 Hz), 4.52 (2H, s), 5.05 (2H, s), 5.29 (2H, s), 6.87-6.90 (1H, m), 7.04-7.10 (2H, m), 7.25(2H, d, J = 8.1 Hz), 7.30-7.35 (3H, m), 7.76 (1H, dd, J = 4.3, 1.0 Hz), 8.02 (1H, d, J = 1.2 Hz), 8.26 (1H, s), 8.36 (1H, t, J = 5.7 Hz) |
| 106 | 2.10 (3H, d, J = 0.6 Hz), 3.20 (3H, s), 3.81 (3H, s), 4.43 (2H, d, J = 5.3 Hz), 4.49 (2H, s), 5.01 (2H, s), 5.25 (2H, s), 6.07 (1H, dd, J = 6.9, 1.9 Hz), 6.20 (1H, s), 7.01 (1H, td, J = 9.2, 1.7 Hz), 7.09-7.15 (1H, m), 7.18-7.24 (4H, m), 7.61 (1H, d, J = 6.9 Hz), 8.20 (1H, s), 8.23 (1H, t, J = 5.0 Hz) |
| 108 | 3.20 (3H, s), 3.81 (3H, s), 2.50 (2H, d, J = 3.6 Hz), 4.49 (2H, s), 5.00 (2H, s), 5.26 (2H, s), 6.43 (1H, dd, J = 10.0, 5.4 Hz), 7.01 (1H, td, J = 9.2, 1.7 Hz), 7.09-7.15 (1H, m), 7.21 (2H, d, J = 8.2 Hz), 7.27 (2H, d, J = 8.2 Hz), 7.53-7.58 (1H, m), 8.01 (1H, dd, J = 4.6, 3.4 Hz), 8.21 (1H, s), 8.23 (1H, t, J = 5.2 Hz) |
| 109 | 2.50 (3H, t, J = 1.8 Hz), 3.20 (3H, s), 3.81 (3H, s), 3.98 (2H, q, J = 7.0 Hz), 4.43 (2H, d, J = 5.1 Hz), 4.49 (2H, s), 4.98 (2H, s), 5.25 (2H, s), 5.77 (1H, d, J = 2.7 Hz), 5.92 (1H, dd, J = 7.6, 2.9 Hz), 7.01 (1H, td, J = 9.2, 1.7 Hz), 7.09-7.15 (1H, m), 7.18-7.23 (4H, m), 7.61 (1H, d, J = 7.6 Hz), 8.20 (1H, s), 8.23 (1H, t, J = 5.1 Hz) |
| 121 | 2.26 (3H, s), 3.81 (3H, s), 4.41 (2H, d, J = 6.3 Hz), 5.07 (2H, s), 5.16 (2H, s), 6.22 (1H, ddd, J = 6.6, 6.6, 1.4 Hz), 6.40 (1H, d, J = 8.8 Hz), 6.81-6.85 (1H, m), 7.00-7.07 (2H, m), 7.17 (2H, d, J = 8.2 Hz), 7.27 (2H, d, J = 8.1 Hz), 7.41 (1H, ddd, J = 8.9, 6.5, 2.0 Hz), 7.64 (1H, s), 7.76 (1H, dd, J = 6.7, 2.0 Hz), 8.31 (1H, t, J = 6.0 Hz) |
| 124 | 3.82 (3H, s), 4.44 (2H, d, J = 6.2 Hz), 5.08 (2H, s), 5.40 (2H, s), 6.22 (1H, dt, J = 6.6, 1.4 Hz), 6.40 (1H, d, J = 8.9 Hz), 6.85 (1H, dt, J = 6.6, 1.8 Hz), 7.01-7.08 (2H, s), 7.19 (2H, d, J = 8.1 Hz), 7.28 (2H, d, J = 8.1 Hz), 7.41 (1H, ddd, J = 8.8. 6.6, 2.1 Hz), 7.75 (1H, dd, J = 6.6, 1.7 Hz), 8.09 (1H, s), 8.68 (1H, br. s) |
| 126 | 1.90-1.94 (4H, m), 3.31-3.37 (4H, m), 3.82 (3H, s), 4.39 (2H, d, J = 5.6 Hz), 5.26(2H, s), 6.44 (1H, d, J = 8.6 Hz), 6.85-6.90 (1H, m), 7.03-7.10 (2H, m), 7.50 (1H, dd, J = 8.8, 2.4 Hz), 8.14 (1H, d, J = 2.3 Hz), 8.36 (1H, d, J = 0.6 Hz), 8.74 (1H, t, J = 5.8 Hz) |
| 139 | 2.81 (3H, s), 2.98 (1H, dd, J = 12.0, 7.3 Hz), 3.26 (1H, dd, J = 12.0, 2.6 Hz), 3.35-3.45 (2H, m), 4.26-4.28 (1H, m), 5.04 (2H, s), 5.07 (2H, s), 5.37 (2H, br. s), 6.22 (1H, td, J = 6.6, 1.3 Hz), 6.40 (1H, d, J = 8.8 Hz), 6.68 (1H, d, J = 8.7 Hz), 6.73 (1H, d, J = 2.4 Hz), 6.80 (1H, dd, J = 8.6, 2.4 Hz), 7.21 (2H, d, J = 8.2 Hz), 7.27 (2H, d, J = 8.1 Hz), 7.39-7.43 (lH, m), 7.76 (1H, dd, J = 7.0, 1.9 Hz), 7.99 (1H, s), 8.00 (1H, t, J = 5.7 Hz) |
| 140 | 2.96-3.02 (1H, m), 3.29-3.34 (1H, m), 3.34-3.43 (2H, m), 4.07-4.12 (1H, m), 5.04 (2H, s), 5.07 (2H, s), 5.36 (2H, br. s), 5.93 (1H, br. s), 6.22 (1H, td, J = 6.7, 1.4 Hz), 6.40 (1H, d, J = 9.9 Hz), 6.55-6.58 (1H, m), 6.68-6.71 (2H, m), 7.21 (2H, d, J = 8.1 Hz), 7.27 (2H, d, J = 8.2 Hz), 7.39-7.43 (1H, m), 7.76 (1H, dd, J = 7.0, 2.0 Hz), 7.98 (1H, t, J = 5.8 Hz), 7.99 (1H, s) |

Biological Methods

The ability of the compounds of formula (I) to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data Acquired from these Assays are Shown in Table 14.

Selected compounds were further screened for inhibitory activity against the related enzyme KLK1. The ability of the compounds of formula (I) to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data Acquired from this Assay are Shown in Table 14.

Selected compounds were further screened for inhibitory activity against the related enzyme FXIa. The ability of the compounds of formula (I) to inhibit FXIa may be determined using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 µM of the test compound. Residual enzyme activity (initial rate of reaction) was determined by measuring the change in optical absorbance at 410 nm.

Data Acquired from this Assay are Shown in Table 14

TABLE 14

| Example Number | $IC_{50}$ (human PKal) nM | $IC_{50}$ (human KLK1) nM | % Inhibition @ 40 µM (human FXIa) |
|---|---|---|---|
| 1 | 698 | >10000 | 0 |
| 2 | 8.7 | >10000 | 8 |
| 3 | 2580 | >10000 | 3 |
| 4 | 136 | >10000 | |
| 5 | 364 | >10000 | |
| 6 | 2360 | >10000 | 0 |
| 7 | >10000 | >10000 | |
| 8 | 539 | >10000 | |
| 9 | 239 | >10000 | |
| 10 | 1270 | >10000 | |
| 11 | 456 | >10000 | |
| 12 | 746 | >10000 | |
| 13 | 439 | >10000 | |
| 14 | 514 | >10000 | |
| 15 | 219 | >10000 | |
| 16 | 263 | >10000 | |
| 17 | 865 | >10000 | |
| 18 | 373 | >10000 | |
| 19 | 1130 | >10000 | |
| 20 | 740 | >10000 | |
| 21 | 257 | >10000 | |
| 22 | 1350 | >10000 | |
| 23 | 1060 | >10000 | |
| 24 | 717 | >10000 | |
| 25 | 1840 | >10000 | |
| 26 | 1340 | >10000 | |
| 27 | >10000 | >10000 | |
| 28 | 280 | >10000 | |
| 29 | 2190 | >10000 | |
| 30 | 915 | >10000 | |
| 31 | 392 | >10000 | |
| 32 | 7870 | >10000 | |
| 36 | 4170 | >10000 | 0 |
| 37 | 392 | >10000 | 0 |
| 39 | 7870 | >10000 | 0 |
| 40 | 3700 | >10000 | 1 |
| 41 | 3.3 | >40000 | 0 |
| 42 | 831 | >10000 | 1 |
| 45 | 144 | >10000 | |
| 46 | 2400 | >10000 | |
| 47 | 753 | >10000 | |
| 48 | 647 | >10000 | 2 |
| 49 | 5450 | >10000 | 0 |
| 50 | 1800 | >10000 | |
| 51 | 48.9 | >40000 | |
| 52 | 23.3 | >40000 | 1 |
| 53 | 20.2 | >10000 | |
| 54 | 2.1 | >40000 | 17 |
| 58 | 5780 | >10000 | 0 |
| 59 | 73.4 | >10000 | 0 |
| 62 | 572 | >10000 | 0 |
| 63 | 342 | >10000 | 0 |
| 64 | 35.2 | >10000 | 0 |

TABLE 14-continued

| Example Number | $IC_{50}$ (human PKal) nM | $IC_{50}$ (human KLK1) nM | % Inhibition @ 40 µM (human FXIa) |
|---|---|---|---|
| 65 | 43.3 | >10000 | 0 |
| 66 | 4.6 | >10000 | 4 |
| 67 | 393 | >10000 | 0 |
| 68 | 81.1 | >10000 | 6 |
| 69 | 16.8 | >40000 | 0 |
| 70 | 26.7 | >10000 | 6 |
| 71 | 300 | >10000 | 0 |
| 72 | 6610 | >10000 | 1 |
| 73 | 120 | >10000 | 8 |
| 76 | 28.3 | >40000 | 5 |
| 77 | 0.6 | >40000 | 28 |
| 78 | 612 | >10000 | 0 |
| 79 | 14.7 | >40000 | 2 |
| 80 | 20.4 | >40000 | |
| 81 | 2.3 | >40000 | 1 |
| 83 | 6.8 | >40000 | 14 |
| 85 | 79.2 | >40000 | 46 |
| 86 | 8.7 | >40000 | |
| 87 | >10000 | >10000 | 2 |
| 90 | 154 | >40000 | 2 |
| 91 | 523 | >10000 | 0 |
| 92 | 16.0 | >10000 | 4 |
| 94 | 780 | >10000 | 0 |
| 95 | 308 | >40000 | 1 |
| 96 | 75.0 | >40000 | 0 |
| 97 | 153 | >10000 | 0 |
| 99 | 6.4 | >10000 | 4 |
| 129 | 437 | >40000 | 0 |
| 130 | 174 | >40000 | 0 |
| 131 | 1510 | >10000 | 0 |
| 132 | 135 | >40000 | 0 |
| 133 | 90.2 | >10000 | 1 |
| 104 | 691 | >10000 | 0 |
| 106 | 140 | >10000 | 2 |
| 108 | 5.5 | >10000 | |
| 109 | 2980 | >10000 | 2 |
| 121 | 43.9 | >10000 | 0 |
| 124 | 191 | >10000 | 0 |
| 126 | 742 | >10000 | 10 |
| 139 | 64.7 | >40000 | 33 |
| 140 | 10.6 | >40000 | 9 |

Pharmacokinetics

Pharmacokinetic studies of the compounds in Table 15 were performed to assess the pharmacokinetics following a single oral dose in male Sprague-Dawley rats. Two rats were given a single po dose of 5 mL/kg of a nominal 2 mg/mL (10 mg/kg) composition of test compound in vehicle. Following dosing, blood samples were collected over a period of 24 hours. Sample times were 5, 15 and 30 minutes then 1, 2, 4, 6, 8 and 12 hours. Following collection, blood samples were centrifuged and the plasma fraction analysed for concentration of test compound by LCMS. Oral exposure data acquired from these studies are shown below:

TABLE 15

Oral exposure data

| Example Number | Vehicle | Dose po (mg/kg) | Cmax (ng/mL) | Tmax (min) |
|---|---|---|---|---|
| 2 | 10% DMSO/10% cremophor/80% SWFI | 9.5 | 351 | 60 |
| 41 | 10% DMSO/10% cremophor/80% SWFI | 10.5 | 1534 | 180 |
| 51 | 5% cremophor/5% ethanol/90% phosphate buffered saline | 13.7 | 101 | 15 |
| 52 | 10% DMSO/10% cremophor/80% SWFI | 17.9 | 1472 | 45 |

TABLE 15-continued

Oral exposure data

| Example Number | Vehicle | Dose po (mg/kg) | Cmax (ng/mL) | Tmax (min) |
|---|---|---|---|---|
| 53 | 10% DMSO/10% cremophor/80% SWFI | 8.6 | 1031 | 15 |
| 66 | 10% DMSO/10% cremophor/80% SWFI | 11.3 | 2892 | 60 |
| 77 | 10% DMSO/10% cremophor/80% SWFI | 5.5 | 397 | 30 |

What is claimed is:

1. A method of treating a disease or condition in which plasma kallikrein activity is implicated, comprising administration to a subject in need thereof a therapeutically effective amount of a compound of formula (I), or a pharmaceutically acceptable salt or solvate thereof, wherein the disease or condition in which plasma kallikrein activity is implicated is hereditary angioedema, and wherein the compound of Formula (I) is:

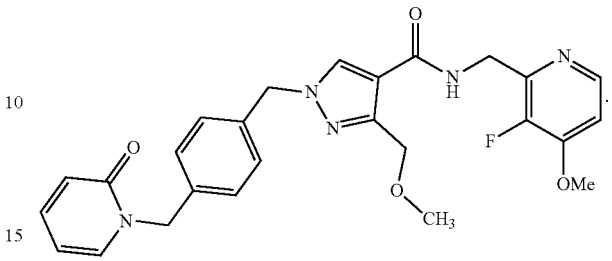

* * * * *